(12) United States Patent  
Mikamiyama

(10) Patent No.: US 8,518,934 B2  
(45) Date of Patent: Aug. 27, 2013

(54) OXYCARBAMOYL COMPOUNDS AND THE USE THEREOF

(75) Inventor: Hidenori Mikamiyama, Osaka (JP)

(73) Assignee: Shonogi & Co., Ltd., Osaka (JP)

( * ) Notice: Subject to any disclaimer, the term of this patent is extended or adjusted under 35 U.S.C. 154(b) by 235 days.

(21) Appl. No.: 12/997,544

(22) PCT Filed: Jun. 11, 2009

(86) PCT No.: PCT/JP2009/061140  
§ 371 (c)(1),  
(2), (4) Date: Dec. 10, 2010

(87) PCT Pub. No.: WO2009/151152  
PCT Pub. Date: Dec. 17, 2009

(65) Prior Publication Data  
US 2011/0098276 A1 Apr. 28, 2011

Related U.S. Application Data

(60) Provisional application No. 61/060,723, filed on Jun. 11, 2008.

(51) Int. Cl.  
*C07D 207/02* (2006.01)  
*C07D 211/04* (2006.01)  
*C07D 211/96* (2006.01)

(52) U.S. Cl.  
USPC ...... 514/211.15; 514/176; 514/188; 546/216; 546/184

(58) Field of Classification Search  
USPC .................. 544/129; 546/184, 216; 548/518  
See application file for complete search history.

(56) References Cited

U.S. PATENT DOCUMENTS

| | | | |
|---|---|---|---|
| 3,577,441 A | 5/1971 | Kaminsky et al. |
| 4,585,785 A | 4/1986 | Walsh et al. |
| 5,880,138 A | 3/1999 | Heinz et al. |
| 6,011,035 A | 1/2000 | Snutch et al. |
| 6,136,839 A | 10/2000 | Isakson et al. |
| 6,310,059 B1 | 10/2001 | Snutch |
| 6,340,678 B1 | 1/2002 | Matsuhisa et al. |
| 6,492,375 B2 | 12/2002 | Snutch |
| 2001/0029258 A1 | 10/2001 | Snutch |
| 2003/0199541 A1 | 10/2003 | Lampilas et al. |
| 2004/0204404 A1 | 10/2004 | Zelle et al. |
| 2005/0020572 A1 | 1/2005 | Aszodi et al. |
| 2009/0298878 A1 | 12/2009 | Matsumura et al. |
| 2009/0306136 A1 | 12/2009 | Matsumura et al. |
| 2010/0240703 A1 | 9/2010 | Masui et al. |

FOREIGN PATENT DOCUMENTS

| | | |
|---|---|---|
| CN | 1850823 A | 10/2006 |
| EP | 0 987 264 A1 | 3/2000 |
| EP | 1 307 457 B1 | 4/2004 |
| EP | 1 741 702 A1 | 10/2007 |
| GB | 1 446 980 A | 8/1976 |
| GB | 2 040 933 A | 9/1980 |
| GB | 2 231 048 A | 11/1990 |
| JP | 50-84523 A | 7/1975 |
| WO | WO 98/39325 A | 9/1998 |
| WO | WO 99/24399 A | 5/1999 |
| WO | WO 99/26926 A | 6/1999 |
| WO | WO 00/35886 A2 | 6/2000 |
| WO | WO 02/10172 A1 | 2/2002 |
| WO | WO 02/074741 A1 | 9/2002 |
| WO | WO 2004/022535 A1 | 3/2004 |
| WO | WO 2004/083167 A1 | 9/2004 |
| WO | WO 2004/105750 A1 | 12/2004 |
| WO | WO 2005/048933 A2 | 6/2005 |
| WO | WO 2005/097129 A2 | 10/2005 |
| WO | WO 2005/105743 A1 | 11/2005 |
| WO | WO 2006/040181 A2 | 4/2006 |
| WO | WO 2006/122014 A2 | 11/2006 |
| WO | WO 2007/007886 A1 | 1/2007 |
| WO | WO 2007/028638 A1 | 3/2007 |
| WO | WO 2007/085357 A1 | 8/2007 |
| WO | WO 2007/110449 A1 | 10/2007 |

(Continued)

OTHER PUBLICATIONS

Vippagunta et al. "Crystalline Solids," Advanced Drug Delivery Reviews, 2001, 48, 3-26.*  
Testa, Biochemical Pharmacology 2004; 68, 2097-2106.*  
Liu et al, ChemBioChem, 2008, 9, 2000-2004.*  
Stella et al "Prodrugs: Challenges and Rewards", Part 1, 2007.*  
Braga et al. "Crystal Polymorphism and Multiple Crystal Forms", Struct. Bond, 2009, 132, 25-50.*  
Brower "New paths to pain relief," Nature Biotechnology, vol. 18, (2000), pp. 387-391.  
Castellano et al., "Cloning and Expression of a Neuronal Calcium Channel β Subunit," The Journal of Biological Chemistry, vol. 268, No. 17, (1993), pp. 12359-12366.

(Continued)

*Primary Examiner* — Blessing Fubara  
*Assistant Examiner* — Kauser M Akhoon  
(74) *Attorney, Agent, or Firm* — Finnegan, Henderson, Farabow, Garrett & Dunner, LLP

(57) ABSTRACT

The invention relates to oxycarbamoyl compounds of Formula I:

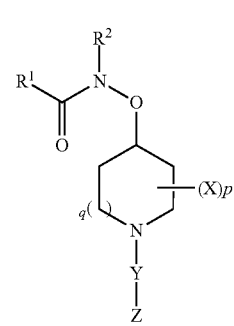

The invention is also directed to the use compounds of Formula I to treat, prevent or ameliorate a disorder responsive to the blockade of calcium channels, and particularly N-type calcium channels. Compounds of the present invention are especially useful for treating pain.

10 Claims, No Drawings

(56) References Cited

FOREIGN PATENT DOCUMENTS

| WO | WO 2007/118853 A1 | 10/2007 |
|---|---|---|
| WO | WO 2007/118854 A1 | 10/2007 |
| WO | WO 2007/147713 A1 | 12/2007 |
| WO | WO 2008/008398 A2 | 1/2008 |
| WO | WO 2008/124118 A1 | 10/2008 |
| WO | WO 2008/150447 A1 | 12/2008 |
| WO | WO 2008/150470 A1 | 12/2008 |
| WO | WO 2009/040659 A2 | 4/2009 |
| WO | WO 2009/151152 A1 | 12/2009 |
| WO | WO 2010/014257 A2 | 2/2010 |

OTHER PUBLICATIONS

Cattanach et al., "Preparation of 4a-Alkoxy-1,2,3,4,4a,9b-hexahydro- and -1,2,3,4-tetra-hyro-benzofuro [3,2-c] pyridines," J. Chem. Soc., Section C: Organic, pp. 53-60, (1971).
Davila, "Molecular and Functional Diversity of Voltage-Gated Calcium Channels," Annals of the New York Academy of Sciences, pp. 102-117, (1999).
Dubel et al., "Molecular cloning of the a-1 subunit of an w-conotoxin-sensitive calcium channel," Proc. National Academy of Science, USA, vol. 89, (1992), pp. 5058-5062.
Filer, "Isotopes in the Physical and Biomedical Sciences," Labeled Compounds (Part A), vol. 1, (1987), Chapter 6, pp. 156-192.
Frampton et al., "Approaches to a Scaleable Synthesis of CH8757: A Potent Inhibitor of Matrix Metalloproteinases," Organic Process Research & Development, vol. 8, No. 3, pp. 414-417, (2004).
Halazy et al., Database CAPLUS on STN (Columbus, OH, USA) No. 135:288686, "Synthesis of substituted N-acyl/sulfonyl pyrrolidine derivatives as bax inhibitors," abstract, 3 pages, (2001).
Halazy et al., Database CAPLUS on STN (Columbus, OH, USA) No. 135:303763, "Preparation of pyrrolidines as inhibitors of Bax function," abstract, 2 pages, (2001).
Hamil et al., "Improved Patch-Clamp Techniques for High-Resolution Current Recording from Cells and Cell-Free Membrane Patches," European Journal of Physiology, (1981), pp. 85-100.
Hanson, "Analgesic, Antipyretic and Anti-inflammatory Drugs," College of Pharmacy and School of Medicine, vol. II, pp. 1196-122 (1995).
Hu et al., "The Discovery of [1-(4-Dimethylamino-benzyl)-piperdin-4-yl]-[4-(3,3-dimethylbutyl)-phenyl]-(3-methyl-but-2-enyl)-Amine, an N-type $Ca^{+2}$ Channel Blocker with Oral Activity for Analgesia," Bioorganic & Medicinal Chemistry, vol. 8, pp. 1203-1212, (2000).
Hunskaar et al., "Formalin test in mice, a useful technique for evaluating mild analgesics," Journal of Neuroscience Methods, (1985), pp. 69-76.
Insel, "Analgesic-Antipretic and Antiinflammatory Agents and Drugs Employed in the Treatment of Gout," Chapter 27, (1996), pp. 617-657.
International Preliminary Report on Patentability issued Dec. 14, 2010, for PCT/JP2009/061140.
International Preliminary Report on Patentability issued Dec. 1, 2009 for International Application No. PCT/US2008/006855.
International Preliminary Report on Patentability issued Dec. 1, 2009, for PCT/US2008/006888.
International Preliminary Report on Patentability issued Jan. 14, 2009, for International Application No. PCT/US2007/015827.
International Search Report mailed Aug. 29, 2008, for International Application No. PCT/US2008/006888.
International Search Report mailed Aug. 29, 2008, for International Application No. PCT/US2008/006855.
International Search Report mailed Aug. 4, 2009, for International Application No. PCT/JP2009/061140.
International Search Report mailed Oct. 7, 2008, for International Application No. PCT/US2007/015827.
Itsuno et al., "Asymmetric Reduction of Chiral Acetophenone Oxime Ethers to Optically Active Primary Amines," Chemistry Letters, pp. 1133-1136 (1986).
Kim, "Rat brain expresses an alternatively spliced form of the dihydropyridine-sensitive L-type calcium channel α2 subunit," Proc. National Academy of Science, USA,vol. 89, (1992), pp. 3251-3255.
Kim et al., "An experimental model for peripheral neuropathy produced by segmental spinal nerve ligation in the rat," Pain 50, (1992), pp. 355-363.
Koch, "cDNA Cloning of a Dihydropyridine-sensitive Calcium Channel from Rat Aorta," The Journal of Biological Chemistry, vol. 265, No. 29, (1990), pp. 17786-17791.
Leeson et al., "Effects of Five-membered Ring Conformation on Bioreceptor Recognition: Identification of 3R-Amino-1-hydroxy-4R-methylpyrrolidin-2-one (L-687,414) as a Potent Glycine/N-Methyl-D-Aspartate Receptor Antagonist," J. Chem. Soc. Chem. Commun., pp. 1578-1580, (1990).
Levine, "Inflammatory pain," Textbook of Pain, $3^{rd}$ Edition, (1994) pp. 45-56.
Lin et al., "Identification of Functionally Distinct Isoforms of the N-Type $Ca^{2+}$ Channel in Rat Sympathetic Ganglia and Brain," Neuron, vol. 18, (1997), pp. 153-166.
McBriar et al., Database CAPLUS on STN (Columbus, OH, USA) No. 137:125084, "Preparation of substituted ureas as MCH antagonists useful in the treatment of obesity," abstract, 2 pages, (2002).
Mori et al., "Synthesis of Carbapenam Skeletons Using a Ruthenium-Catalyzed Cyclization," Organic Letters, vol. 2, No. 20, (2000), pp. 3245-3247.
Phuket et al., "Synthesis and Structure-Activity Studies of Some Antitumor Congeners of $_L$-Canaline," Drug Development Research 47, (1999), pp. 170-177.
Pragnell et al., "Cloning and tissue-specific expression of the brain calcium channel β-subunit," Federation of European Biochemical Societies, vol. 291, (1991), pp. 253-258.
Shibata et al., "Preparation of sulfamide derivatives as antitumor agents," Abstract of WO 2004/083167 identified as CAPLUS 2004: 799553 and as Registry No. RN 765958-60-9 (2 pages) entered Oct. 20, 2004.
Smith et al., Database CAPLUS on STN (Columbus, OH, USA) No. 109:38215, "Synthesis and pharmacological activity on angiotensin-converting enzyme inhibitors: N-mercaptoacyl-4-substituted-s-prolines," abstract, 2 pages, (1988).
Song et al., "(S)-4-Methyl-2-(methylamino)pentanoic Acid [4,4-Bis(4-fluorophenyl)butyl]amide Hydrochloride, a Novel Calcium Channel Antagonist, Is Efficacious in Several Animal Models of Pain," Journal of Medicinal Chemistry, vol. 43, No. 19, pp. 3473-3477, (2000).
Stein et al., "Unilateral Inflammation of the Hindpaw in Rats as a Model of Prolonged Noxious Stimulation: Alterations in Behavior and Nociceptive Thresholds," Pharmacology Biochemistry & Behavior, vol. 31, (1988), pp. 445-451.
Tallier et al., "Use of a sterically demanding Lewis acid to direct ring expansion of monoactivated methylenecyclopropanes," Tetrahedron, (2007), pp. 8469-8477.
Vanderesse et al., "α-Aminoxy Acids as Building Blocks for the Oxime and Hydroxylamine Pseudopeptide Links. Application to the Synthesis of Human Elastase Inhibitors," Journal of Peptide Science, vol. 9, pp. 282-299 (2003).
Vanegas et al., "Effects of antagonists to high-threshold calcium channels upon spinal mechanisms of pain, hyperalgesia and allodynia," PAIN, 85, pp. 9-18, (2000).
Wallace, "Calcium and Sodium Channel Antagonists for the Treatment of Pain," The Clinical Journal of Pain, vol. 16, No. 2, pp. S80-S85, (2000).
Werchan et al., "Verlauf und Produkte der Umsetzung von lsocyanaten mit 2,2,6,6-Tetramethylpiperidin-4-onoxim," Journal für Praktische Chemie(Leipzig) 1979, vol. 321(5), p. 865-869.
Yang et al., "A kind of compound quinolines and its preparation method and use comprising hydroxyimino," Machine translation of CN 1850823A, CNIPR, http://english.cnipr.com/enpat/index.htm, 78 pages, (Dec. 11, 2008).
Yang et al., "Preparation of 1, 8-naphthyridine derivatives as antibacterial agents," Abstract of CN 1850823, STN Tokyo, CAPLUS 2006: 1129102, entered Oct. 30, 2006.
Zámocká et al., "Synthese und carbamoylierung von 4-oximino-2,2,6,6,-tetramethylpiperidin-1-carbon säureestem," Zeitschrift für Chemie, 1980, vol. 20(2), p. 56-57.
European Supplementary Search Report and Search Opinion, mailed Jul. 8, 2011, for European Application No. 07810356.1.

Parthiban et al., "Synthesis and Microbiological Evaluation of Some N-methyl Piperidone Oxime Ethers," Medicinal Chemistry Research, 14(8-9):523-538 (2005).

Smith et al. "Synthesis and Pharmacological Activity of Angiotensin Converting Enzyme Inhibitors: N-(mercaptoacyl)-4-substituted-(s)-prolines," Journal of Medicinal Chemistry, American Chemical Society, 31(4):875-885 (Jan. 1, 1988).

Cossy et al., "A Short Synthesis of Cisapride: A Gastrointestinal Stimulant Derived from cis-4-amino-3-methoxypiperidine," Tetrahedron Letters, 42(33):5713-5715 (Aug. 13, 2001).

Database Registry, Chemical Abstracts Service, "1-methyl-O-[bis(4-fluorophenyl)methyl] oxime-4-piperidinone," Database Accession No. 445392-83-6 (Aug. 29, 2002).

Teodori et al., "Design, Synthesis, and Preliminary Pharmacological Evaluation of 4-Aminopiperidine Derivatives as N-Type Calcium Channel Blockers Active on Pain and Neuropathic Pain," Journal of Medicinal Chemistry, American Chemical Society, 47:6070-6081 (Jan. 1, 2004).

Schroeder et al., "N-Type Calcium Channel Blockers: Novel Therapeutics for the Treatment of Pain," Medicinal Chemistry, Bentham Science Publishers, Ltd., 2(5):535-543 (Sep. 1, 2006).

European Supplementary Search Report and Search Opinion, mailed Aug. 16, 2011, for European Application No. 08767992.4.

* cited by examiner

OXYCARBAMOYL COMPOUNDS AND THE USE THEREOF

This application is a national stage application of and claims priority to PCT International Application No. PCT/JP2009/061140 filed Jun. 11, 2009, which claims the benefit of U.S. Provisional Application No. 61/060,723, filed Jun. 11, 2008, each of which is incorporated herein by reference for all purposes.

TECHNICAL FIELD

This invention is in the field of medicinal chemistry. The invention relates to oxycarbamoyl compounds and the discovery that these compounds act as blockers of calcium ($Ca^{2+}$) channels.

BACKGROUND ART

Calcium ions play fundamental roles in the regulation of many cellular processes. It is therefore essential that their intracellular levels be maintained under strict, yet dynamic control (NPL 1). Voltage-gated calcium channels (VGCC) serve as one of the important mechanisms for fast calcium influx into the cell. Calcium channels are hetero-oligomeric proteins consisting of a pore-forming subunit ($\alpha 1$), which is able to form functional channels on its own in heterologous expression systems, and a set of auxiliary or regulatory subunits. Calcium channels have been classified based on their pharmacological and/or electrophysiological properties. The classification of voltage-gated calcium channels divides them into three groups: (i) high voltage-activated (HVA) channels, which include L-, N-, P-, and Q-types; (ii) intermediate (IVA) voltage-activated R-type channels; and (iii) low voltage-activated (LVA) T-type channels (NPL 1). Voltage-gated calcium channels (VGCC) are also known as voltage-dependent calcium channels (VDCC) or voltage-sensitive calcium channels (VSCC).

Voltage-sensitive calcium channels (VSCC) regulate intracellular calcium concentration, which affects various important neuronal functions such as cellular excitability, neurotransmitter release, hormone secretion, intracellular metabolism, neurosecretory activity and gene expression (NPL 2). N-type channels are found mainly in central and peripheral neurons, being primarily located on presynaptic nerve terminals. These channels regulate the calcium flux required for depolarization-evoked release of a transmitter from synaptic endings. The transmission of pain signals from the periphery to the central nervous system (CNS) is mediated by N-type calcium channels located in the spinal cord (NPL 3).

The six types of calcium channels (i.e., L, N, P, Q, R, and T) are expressed throughout the nervous system (NPL 4). Voltage-sensitive calcium channels of the N-type exist in the superficial laminae of the dorsal horn and are thought to modulate nociceptive processing by a central mechanism. Blockade of the N-type calcium channel in the superficial dorsal horn modulates membrane excitability and inhibits neurotransmitter release, resulting in pain relief. Wallace (NPL 4) suggests that based on animal models, N-type calcium channel antagonists have a greater analgesic potency than sodium channel antagonists. N-type calcium channel blockers have usefulness for neuroprotection and analgesia. Ziconotide, which is a selective N-type calcium channel blocker, has been found to have analgesic activity in animal models and neuroprotective activity in focal and global ischemia models (NPL 3). Examples of known calcium channel blockers include flunarizine, fluspirilene, cilnipide, PD 157767, SB-201823, SB-206284, NNC09-0026, and PD 151307 (NPL 2).

Blockade of N-type channels can prevent and/or attenuate subjective pain as well as primary and/or secondary hyperalgesia and allodynia in a variety of experimental and clinical conditions (NPL 5). N-type voltage-gated calcium channels (VGCC) play a major role in the release of synaptic mediators such as glutamate, acetylcholine, dopamine, norepinephrine, gamma-aminobutyric acid (GABA) and calcitonin gene-related peptide (CGRP).

Inhibition of voltage-gated L-type calcium channels has been shown to be beneficial for neuroprotection (NPL 3). However, inhibition of cardiac L-type calcium channels can lead to hypotension. It is believed that a rapid and profound lowering of arterial pressure tends to counteract the neuroprotective effects of L-type calcium channel blockers. A need exists for antagonists that are selective for N-type calcium channels over L-type calcium channels to avoid potential hypotensive effects.

Similar compounds to those of the present invention are described in PTL 1, PTL 2 and PTL 3, but the structures of these compounds are different from those of the present invention.

CITATION LIST

Patent Literature

{PTL 1} U.S. Pat. No. 4,585,785 A
{PTL 2} WO2002/010172 A1
{PTL 3} WO2000/035886 A1
{PTL 4} U.S. Pat. No. 6,136,839 A

Non Patent Literature

{NPL 1} Davila, H. M., Annals of the New York Academy of Sciences, pp. 102-117 (1999)
{NPL 2} Hu et al., Bioorganic & Medicinal Chemistry 8:1203-1212 (2000)
{NPL 3} Song et al., J. Med. Chem. 43:3474-3477 (2000)
{NPL 4} Wallace, M. S., The Clinical Journal of Pain 16:580-585 (2000)
{NPL 5} Vanegas, H. et al., Pain 85:9-18 (2000)
{NPL 6} Filer, Isotopes in the Physical and Biomedical Sciences, Vol. 1, Labeled Compounds (Part A), Chapter 6 (1987)
{NPL 7} Brower, Nature Biotechnology 2000; 18: 387-391
{NPL 8} Levine, Inflammatory Pain, In: Textbook of Pain, Wall and Melzack eds., 3$^{rd}$ ed., 1994
{NPL 9} Dubel et al. in Proc. Natl. Acad. Sci. U.S.A 89: 5058-5062 (1992)
{NPL 10} Pragnell et al. in FEBS Lett. 291: 253-258 (1991)
{NPL 11} Castellano et al. in J. Biol. Chem. 268: 12359-12366 (1993)
{NPL 12} Kim et al. in Proc. Natl. Acad. Sci. U.S.A. 89: 3251-3255 (1992)
{NPL 13} Koch et al. in J. Biol. Chem. 265: 17786-17791 (1990)
{NPL 14} Lin et al. Neuron 18: 153-166 (1997)
{NPL 15} Hamill et al., Pfluegers Arch. 391: 85-100 (1981)
{NPL 16} Hunskaar, S., O. B. Fasmer, and K. Hole, J. Neurosci. Methods 14: 69-76 (1985)
{NPL 17} Kim and Chung, Pain 50: 355-363 (1992)
{NPL 18} Biochemistry & Behavior 31: 451-455 (1988)
{NPL 19} Paul A. Insel, Analgesic Antipyretic and Antiinflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996)

{NPL 20} Glen R. Hanson, Analgesic, Antipyretic and Anti Inflammatory Drugs in Remington: The Science and Practice of Pharmacy Vol II 1196-1221 (A. R. Gennaro ed. 19th ed. 1995)

SUMMARY OF INVENTION

The present invention is related to the use of oxycarbamoyl compounds represented by Formula I below, and the pharmaceutically acceptable salts, prodrugs and solvates thereof, as blockers of calcium ($Ca^{2+}$) channels. Certain compounds of Formula I show selectivity as N-type calcium channel blockers.

The invention is also related to treating, preventing or ameliorating a disorder responsive to the blockade of calcium channels in a mammal suffering from excess activity of said channels by administering an effective amount of a compound of Formula I, or a pharmaceutically acceptable salt, prodrug or solvate thereof, as described herein. Specifically, the invention is related to treating, preventing or ameliorating a disorder responsive to the blockade of N-type calcium channels in a mammal suffering from excess activity of said channels by administering an effective amount of a compound of Formula I, or a pharmaceutically acceptable salt, prodrug or solvate thereof, as described herein.

One aspect of the present invention is directed to novel compounds of Formula I, or a pharmaceutically acceptable salt, prodrug or solvate thereof.

Another aspect of the present invention is directed to the use of the novel compounds of Formula I, or a pharmaceutically acceptable salt, prodrug or solvate thereof, as blockers of N-type calcium channels.

A further aspect of the present invention is to provide a method for treating, preventing or ameliorating stroke, neuronal damage resulting from head trauma, epilepsy, pain (e.g., acute pain, chronic pain, which includes but is not limited to, neuropathic pain and inflammatory pain, or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia, by administering an effective amount of a compound of Formula I, or a pharmaceutically acceptable salt, prodrug or solvate thereof, to a mammal in need of such treatment, prevention or amelioration.

A further aspect of the present invention is to provide a pharmaceutical composition useful for treating, preventing or ameliorating a disorder responsive to the blockade of calcium ion channels, especially N-type calcium ion channels, said pharmaceutical composition containing an effective amount of a compound of Formula I, or a pharmaceutically acceptable salt, prodrug or solvate thereof, in a mixture with one or more pharmaceutically acceptable carriers.

Also, an aspect of the invention is to provide a method of modulating calcium channels, especially N-type calcium channels, in a mammal, wherein said method comprises administering to the mammal an effective amount of at least one compound of Formula I, or a pharmaceutically acceptable salt, prodrug or solvate thereof.

A further aspect of the present invention is to provide radiolabeled compounds of Formula I and the use of such compounds, or their pharmaceutically acceptable salts, prodrugs or solvates, as radioligands for their binding site on the calcium channel.

A further aspect of the invention is to provide a method for screening a candidate compound for the ability to bind to a receptor using a $^{3}H$, $^{11}C$ or $^{14}C$ radiolabeled compound of Formula I, or a pharmaceutically acceptable salt, prodrug or solvate thereof. This method comprises a) introducing a fixed concentration of the radiolabeled compound to the receptor to form a mixture; b) titrating the mixture with a candidate compound; and c) determining the binding of the candidate compound to said receptor.

A further aspect of the invention is to provide the use of a compound of Formula I, or a pharmaceutically acceptable salt, prodrug or solvate thereof, in the manufacture of a medicament for treating, preventing or ameliorating stroke, neuronal damage resulting from head trauma, epilepsy, pain, migraine, a mood disorder, schizophrenia, a neurodegenerative disorder, depression, anxiety, a psychosis, hypertension, or cardiac arrhythmia in a mammal. In a preferred embodiment, the invention provides the use of a compound of Formula I, or a pharmaceutically acceptable salt, prodrug or solvate thereof, in the manufacture of a medicament for treating, preventing or ameliorating pain (e.g., acute pain, chronic pain, which includes but is not limited to, neuropathic pain and inflammatory pain or surgical pain).

Additional embodiments and advantages of the invention will be set forth in part in the description that follows, and will flow from the description, or may be learned by practice of the invention. The embodiments and advantages of the invention will be realized and attained by means of the elements and combinations particularly pointed out in the appended claims.

It is to be understood that both the foregoing summary and the following detailed description are exemplary and explanatory only and are not restrictive of the invention, as claimed.

DESCRIPTION OF EMBODIMENTS

One aspect of the present invention is based upon the use of compounds of Formula I, and the pharmaceutically acceptable salts, prodrugs and solvates thereof, as blockers of $Ca^{2+}$ channels. In view of this property, compounds of Formula I, and the pharmaceutically acceptable salts, prodrugs and solvates thereof, are useful for treating disorders responsive to the blockade of calcium ion channels. In one aspect, compounds of Formula I, and the pharmaceutically acceptable salts, prodrugs and solvates thereof, selectively block N-type calcium ion channels and, thus, are useful for treating disorders responsive to the selective blockade of N-type calcium ion channels.

The present invention provides
1) A compound having Formula I:

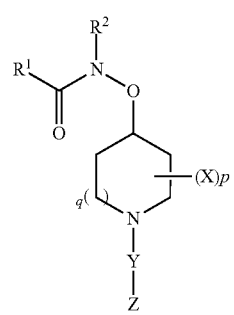

a prodrug, a pharmaceutically acceptable salt or a solvate thereof, wherein:

R$^1$ is optionally substituted alkyl, optionally substituted alkenyl, optionally substituted alkynyl, optionally substituted amino, optionally substituted carbamoyl, optionally substituted cycloalkyl, optionally substituted aryl or optionally substituted heterocyclyl, R$^2$ is hydrogen or optionally substituted alkyl, or R$^1$ and R$^2$ can be taken together with the adjacent atoms to form a ring;

Y is CR$^3$R$^4$, CO or SO$_m$;

R$^3$ and R$^4$ are each independently hydrogen, cyano, optionally substituted alkyl, optionally substituted alkenyl, optionally substituted alkynyl, optionally substituted cycloalkyl, optionally substituted aryl or optionally substituted heterocyclyl, or R$^3$ and R$^4$ can be taken together with the neighboring carbon atom to form a ring;

Z is optionally substituted alkyl, optionally substituted alkenyl, optionally substituted alkynyl, optionally substituted cycloalkyl, optionally substituted aryl, optionally substituted heterocyclyl, NR$^5$R$^6$, COR$^5$ or CONR$^5$R$^6$;

each X is independently =O, optionally substituted alkyl, optionally substituted alkenyl, optionally substituted alkynyl, halogen, cyano, nitro, NR$^5$R$^6$, OR$^5$, SR$^5$, COR$^5$, COOR$^5$, CONR$^5$R$^6$, NR$^5$COR$^6$, OCOR$^5$, SOR$^5$, SO$_2$R$^5$, SO$_3$R$^5$, SONR$^5$R$^6$, SO$_2$NR$^5$R$^6$, NR$^5$SOR$^6$, or NR$^5$SO$_2$R$^6$;

R$^5$ and R$^6$ are each independently hydrogen, optionally substituted alkyl, optionally substituted alkenyl, optionally substituted alkynyl, optionally substituted cycloalkyl, optionally substituted ary or optionally substituted heterocyclyl;

m is 1 or 2;

p is 0, 1 or 2; and q is 0 or 1;

and provided that when q is 0, X is not OH or COORS.

2) The compound of the above 1), wherein Y is CR$^3$R$^4$ or SO$_2$; and

R$^3$ and R$^4$ are each independently hydrogen, cyano, optionally substituted alkyl or optionally substituted aryl.

3) The compound of the above 1), wherein Z is optionally substituted aryl or optionally substituted heterocyclyl.

4) The compound of the above 1), wherein Z is optionally substituted phenyl.

5) The compound of the above 1), wherein R$^1$ is optionally substituted alkyl, optionally substituted alkenyl, optionally substituted amino, optionally substituted carbamoyl, optionally substituted cycloalkyl, optionally substituted aryl or optionally substituted heterocyclyl; or R$^1$ and R$^2$ can be taken together with the neighboring nitrogen atom to form a ring.

6) The compound of the above 1), wherein:

R$^1$ is optionally substituted alkyl, optionally substituted alkenyl, optionally substituted carbamoyl, optionally substituted cycloalkyl, optionally substituted aryl or optionally substituted heterocyclyl, R$^2$ is hydrogen, or R$^1$ and R$^2$ can be taken together with the neighboring nitrogen atom to form a ring, Y is SO$_2$; and Z is optionally substituted aryl.

7) A compound having Formula I:

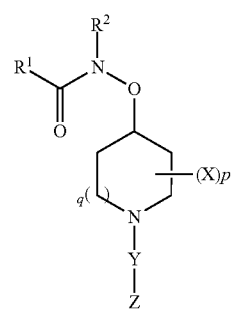

a prodrug, a pharmaceutically acceptable salt or a solvate thereof, wherein:

R$^1$ is optionally substituted amino,

R$^2$ is hydrogen or optionally substituted alkyl,

Y is CR$^3$R$^4$, CO or SO$_m$;

R$^3$ and R$^4$ are each independently hydrogen, cyano, optionally substituted alkyl, optionally substituted alkenyl, optionally substituted alkynyl, optionally substituted cycloalkyl, optionally substituted aryl or optionally substituted heterocyclyl, or R$^3$ and R$^4$ can be taken together with the neighboring carbon atom to form a ring;

Z is optionally substituted alkyl, optionally substituted alkenyl, optionally substituted alkynyl, optionally substituted cycloalkyl, optionally substituted aryl, optionally substituted heterocyclyl, NR$^5$R$^6$, COR$^5$ or CONR$^5$R$^6$;

each X is independently =O, optionally substituted alkyl, optionally substituted alkenyl, optionally substituted alkynyl, halogen, cyano, nitro, NR$^5$R$^6$, OR$^5$, SR$^5$, COR$^5$, COOR$^5$, CONR$^5$R$^6$, NR$^5$COR$^6$, OCOR$^5$, SOR$^5$, SO$_2$R$^5$, SO$_3$R$^5$, SONR$^5$R$^6$, SO$_2$NR$^5$R$^6$, NR$^5$SOR$^6$, or NR$^5$SO$_2$R$^6$;

R$^5$ and R$^6$ are each independently hydrogen, optionally substituted alkyl, optionally substituted alkenyl, optionally substituted alkynyl, optionally substituted cycloalkyl, optionally substituted aryl or optionally substituted heterocyclyl;

m is 1 or 2;

p is 0, 1 or 2; and q is 0 or 1.

8) A pharmaceutical composition, comprising the compound of any one of the above 1) to 7) and a pharmaceutically acceptable carrier.

9) A method of treating, preventing or ameliorating a disorder responsive to the blockade of calcium channels in a mammal suffering from said disorder, comprising administering to a mammal in need of such treatment, prevention or amelioration an effective amount of a compound of any one of the above 1) to 7).

10) The method of the above 9), wherein a disorder responsive to the blockade of N-type calcium channels is treated, prevented or ameliorated.

11) A method for treating, preventing or ameliorating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal, comprising administering an effective amount of a compound of any one of the above 1) to 7).

12) The method of the above 11), wherein the method is for treating, preventing or ameliorating pain selected from chronic pain, acute pain, and surgical pain.

13) A method of modulating calcium channels in a mammal, comprising administering to the mammal at least one compound of any one of the above 1) to 7).

14) The method of the above 13), wherein the N-type calcium channel is modulated.

15) The compound having Formula I as described in any one of the above 1) to 7), wherein the compound is $^3$H, $^{11}$C, or $^{14}$C radiolabeled.

16) A method of screening a candidate compound for the ability to bind to a receptor using a radiolabeled compound of the above 15), comprising a) introducing a fixed concentration of the radiolabeled compound to the receptor to form a mixture; b) titrating the mixture with a candidate compound; and c) determining the binding of the candidate compound to said receptor.

17) Use of a compound of Formula I as described in any one of the above 1) to 7) in the manufacture of a medicament for treating, preventing or ameliorating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal.

18) Use of a compound of Formula I as described in any one of the above 1) to 7) in the manufacture of a medicament for treating, preventing or ameliorating pain selected from chronic pain, acute pain, and surgical pain.

19) A pharmaceutical composition for modulating calcium channels in a mammal, comprising the compound having Formula I:

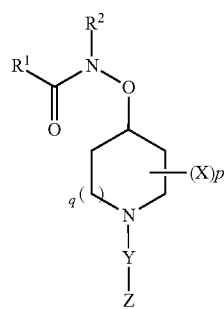

a prodrug, a pharmaceutically acceptable salt or a solvate thereof, wherein:

$R^1$ is optionally substituted alkyl, optionally substituted alkenyl, optionally substituted alkynyl, optionally substituted amino, optionally substituted carbamoyl, optionally substituted cycloalkyl, optionally substituted aryl or optionally substituted heterocyclyl, $R^2$ is hydrogen or optionally substituted alkyl, or $R^1$ and $R^2$ can be taken together with the adjacent atoms to form a ring;

Y is $CR^3R^4$, CO or $SO_m$;

$R^3$ and $R^4$ are each independently hydrogen, cyano, optionally substituted alkyl, optionally substituted alkenyl, optionally substituted alkynyl, optionally substituted cycloalkyl, optionally substituted aryl or optionally substituted heterocyclyl, or $R^3$ and $R^4$ can be taken together with the neighboring carbon atom to form a ring;

Z is optionally substituted alkyl, optionally substituted alkenyl, optionally substituted alkynyl, optionally substituted cycloalkyl, optionally substituted aryl, optionally substituted heterocyclyl, $NR^5R^6$, $COR^5$ or $CONR^5R^6$;

each X is independently =O, optionally substituted alkyl, optionally substituted alkenyl, optionally substituted alkynyl, halogen, cyano, nitro, $NR^5R^6$, $OR^5$, $SR^5$, $COR^5$, $COOR^5$, $CONR^5R^6$, $NR^5COR^6$, $OCOR^5$, $SOR^5$, $SO_2R^5$, $SO_3R^5$, $SONR^5R^6$, $SO_2NR^5R^6$, $NR^5SOR^6$, or $NR^5SO_2R^6$;

$R^5$ and $R^6$ are each independently hydrogen, optionally substituted alkyl, optionally substituted alkenyl, optionally substituted alkynyl, optionally substituted cycloalkyl, optionally substituted aryl or optionally substituted heterocyclyl;

m is 1 or 2;

p is 0, 1 or 2; and q is 0 or 1;

and a pharmaceutically acceptable carrier.

20) A method of treating, preventing or ameliorating a disorder responsive to the blockade of calcium channels in a mammal suffering from said disorder, comprising administering to a mammal in need of such treatment, prevention or amelioration an effective amount of a compound of the above 19).

21) The method of the above 20), wherein a disorder responsive to the blockade of N-type calcium channels is treated, prevented or ameliorated.

22) A method for treating, preventing or ameliorating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal, comprising administering an effective amount of a compound of the above 19).

23) The method of the above 22), wherein the method is for treating, preventing or ameliorating pain selected from the group consisting of chronic pain, acute pain, and surgical pain.

24) A method of modulating calcium channels in a mammal, comprising administering to the mammal at least one compound the above 19).

25) The method of the above 24), wherein the N-type calcium channel is modulated.

26) A method of screening a candidate compound for the ability to bind to a receptor using a radiolabeled compound of the above 19), comprising a) introducing a fixed concentration of the radiolabeled compound to the receptor to form a mixture; b) titrating the mixture with a candidate compound; and c) determining the binding of the candidate compound to said receptor.

27) Use of a compound of the above 19) in the manufacture of a medicament for the treating, preventing or ameliorating stroke, neuronal damage resulting from head trauma, epilepsy, pain, migraine, a mood disorder, schizophrenia, a neurodegenerative disorder, depression, anxiety, a psychosis, hypertension or cardiac arrhythmia in a mammal.

28) Use of a compound of the above 19) in the manufacture of a medicament for the treating, preventing or ameliorating pain selected from the group consisting of chronic pain, acute pain, and surgical pain.

29) A kit comprising a container containing an effective amount of the compound or a pharmaceutically acceptable derivative of the compound of the above 1).

In the present specification, the term "halogen" includes fluorine, chlorine, bromine and iodine. Fluorine or chlorine is preferable. The halogen parts of "haloalkyl", "haloalkoxy", "haloacyl", "haloalkylaryl", "haloalkylarylalkyl", "haloalkylcycloalkyl", "haloalkylheterocyclyl", "haloalkoxyalkyl", "haloalkoxyaryl", "haloalkoxyarylalkyl", "haloalkoxyheterocyclyl", "halogenoaryl", "halogenoarylalkyl", "halogenoaryloxy", and "halogenoaryloxyalkyl" are the same as the above "halogen".

The term "alkyl" includes straight or branched chain alkyl having 1 to 10 carbon atoms, preferably 1 to 6 carbon atoms and most preferably 1 to 3 carbon atoms. For example, included are methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

The optional substituents in "optionally substituted alkyl", include 1) halogen,
2) hydroxy,
3) carboxy,
4) mercapto,
5) cyano,
6) alkoxy optionally substituted with at least one substituent selected from the group consisting of Group A and Group C,
7) acyl optionally substituted with at least one substituent selected from the group consisting of Group A, Group B and Group C,
8) acyloxy optionally substituted with at least one substituent selected from the group consisting of Group A, Group B and Group C
9) alkoxycarbonyl optionally substituted with at least one substituent selected from the group consisting of Group A and Group C,
10) aryloxycarbonyl optionally substituted with at least one substituent selected from the group consisting of Group A, Group B and Group C,
11) alkylthio optionally substituted with at least one substituent selected from the group consisting of Group A and Group C,
12) alkylsulfonyl optionally substituted with at least one substituent selected from the Group A and Group C,
13) amino optionally substituted with at least one substituent selected from the group consisting of Group A, Group B and Group C
14) imino optionally substituted with at least one substituent selected from the group consisting of Group A, Group B and Group C,
15) carbamoyl optionally substituted with at least one substituent selected from the group consisting of Group B and Group C,
16) carbamoyloxy optionally substituted with at least one substituent selected from the group consisting of Group B and Group C,
17) thiocarbamoyl optionally substituted with at least one substituent selected from the group consisting of Group B and Group C,
18) cycloalkyl optionally substituted with at least one substituent selected from the group consisting of Group A, Group B and Group C,
19) cycloalkenyl optionally substituted with at least one substituent selected from the group consisting of Group A, Group B and Group C,
20) aryl optionally substituted with at least one substituent selected from the group consisting of Group A, Group B and Group C,
21) heterocyclyl optionally substituted with at least one substituent selected from the group consisting of Group A, Group B, Group C and oxo,
22) aryloxy optionally substituted with at least one substituent selected from the group consisting of Group A, Group B and Group C,
23) arylthio optionally substituted with at least one substituent selected from the group consisting of Group A, Group B and Group C,
24) cycloalkylsulfonyl optionally substituted with at least one substituent selected from the group consisting of Group A, Group B and Group C,
25) arylsulfonyl optionally substituted with at least one substituent selected from the group consisting of Group A, Group B and Group C,
26) heterocyclylsulfonyl optionally substituted with at least one substituent selected from the group consisting of Group A, Group B, Group C, and oxo and the like.

Group A includes hydroxy, halogen, cyano, alkoxy, haloalkoxy, hydroxyalkoxy, arylalkoxy, acyl, haloacyl, aminoacyl, acyloxy, carboxy, alkoxycarbonyl, carbamoyl, alkylcarbamoyl, and optionally substituted amino, wherein the substituents are selected from the group consisting of alkyl, hydroxyalkyl, alkoxyalkyl, acyl, cycloalkyl, aryl and heterocyclyl.

Group B includes alkyl, haloalkyl, hydroxyalkyl, alkoxyalkyl, aminoalkyl, alkylamino, alkylaminoalkyl, arylalkyl and heterocyclylalkyl.

Group C includes optionally substituted cycloalkyl, optionally substituted cycloalkenyl, optionally substituted aryl, optionally substituted aryloxy and optionally substituted heterocyclyl, wherein the substituents are selected from the group consisting of Group A, Group B and oxo.

The term "optionally substituted alkyl" refers to alkyl that can be substituted with one or more of the above-mentioned substituents at any possible positions.

The alkyl parts of "alkoxy", "alkoxycarbonyl", "alkylsulfonyl", "alkylthio", "haloalkyl", "hydroxyalkyl", "aminoalkyl", "alkylamino", "alkylaminoalkyl", "arylalkyl", "haloalkoxy", "hydroxyalkoxy", "alkoxyalkyl", "arylalkoxy", "alkylcarbamoyl", "heterocyclylalkyl", "alkylenedioxy", "alkoxyaryl", "alkoxyarylalkyl", "alkoxyheterocyclyl", "alkylaryl", "alkylarylalkyl", "alkylcycloalkyl", "alkylheterocyclyl", "aryloxyalkyl", "haloalkylaryl", "haloalkylarylalkyl", "haloalkylcycloalkyl", "haloalkylheterocyclyl", "haloalkoxyalkyl", "haloalkoxyaryl", "haloalkoxyarylalkyl", "halogenoarylalkyl", "halogenoaryloxyalkyl", "haloalkoxyheterocyclyl", "cyanoalkyl", and "cycloalkylalkyl" are as defined for "alkyl". The optional substituents in "optionally substituted alkoxy" include those defined for "optionally substituted alkyl".

The term "alkenyl" refers to straight or branched chain alkenyl of 2 to 10 carbon atoms, preferably 2 to 8 carbon atoms, more preferably 3 to 6 carbon atoms having at least one double bond at any possible positions. For example, useful alkenyl groups include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

Substituents for "optionally substituted alkenyl" are those defined for "optionally substituted alkyl".

The term "alkynyl" refers to straight or branched chain alkynyl of 2 to 10 carbon atoms, preferably 2 to 8 carbon atoms, more preferably 3 to 6 carbon atoms having at least one triple bond at any possible positions. Furthermore, "alkynyl" can have at least one double bond at any possible positions. Suitable alkynyl groups are, for example, ethynyl, propynyl, butynyl, pentynyl, hexynyl, heptynyl, octynyl, nonynyl, decynyl and the like. Substituents for "optionally substituted alkynyl" are those defined for "optionally substituted alkyl".

The term "acyl" refers to straight or branched chain aliphatic acyl having 1 to 10 carbon atoms, preferably 1 to 6 carbon atoms, more preferably 1 to 4 carbon atoms, cyclic aliphatic acyl having 4 to 9 carbon atoms, preferably 4 to 7 carbon atoms, aroyl and heterocyclylcarbonyl. Suitable acyl groups include, for example, formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl, pyridinecarbonyl, pyrimidinecarbonyl, piperidincarbonyl, piperazinocarbonyl, morpholinocarbonyl and the like.

The acyl part in "acyloxy" 'haloacyl" and "aminoacyl" is that defined for "acyl". The term "cycloalkyl" refers to a carbocycle having 3 to 8 carbon atoms, and includes cyclopropyl, cyclobutyl, cyclopentyl, cyclohexyl, cycloheptyl, cyclooctyl and the like. Examples of substituents for "optionally substituted cycloalkyl" are 1) alkyl optionally substituted with at least one substituent selected from the group consisting of Group A and Group C, and 2) the same as those defined for "optionally substituted alkyl".

The term "optionally substituted cycloalkyl" refers to a cycloalkyl defined above that can be substituted with one or more of these substituents.

The cycloalkyl part of "cycloalkylsulfonyl", "alkylcycloalkyl", "cycloalkylalkyl", and "haloalkylcycloalkyl" is as defined for "cycloalkyl".

The term "cycloalkenyl" refers to a group having at least one double bond at any possible positions in the above "cycloalkyl". Examples are cyclopropenyl, cyclobutenyl, cyclopentenyl, cyclohexenyl and cyclohexadienyl. Substituents for "optionally substituted cycloalkenyl" are those defined for "optionally substituted cycloalkyl."

As substituents for "optionally substituted amino" and "optionally substituted carbamoyl", exemplified are 1) alkyl optionally substituted with at least one substituent selected from the group consisting of Group A and Group C, and 2) the same as those defined for "optionally substituted alkyl".

As preferable substituents for "optionally substituted amino" for $R^1$, exemplified are 1) alkyl optionally substituted with at least one substituent selected from the group consisting of Group A and Group C, 2) cycloalkyl optionally substituted with at least one substituent selected from the group consisting of Group A, Group B and Group C, 3) aryl optionally substituted with at least one substituent selected from the group consisting of Group A, Group B and Group C, 4) heterocyclyl optionally substituted with at least one substituent selected from the group consisting of Group A, Group B, Group C and oxo.

As more preferable substituents for "optionally substituted amino" for $R^1$, exemplified are 1) $C_1$ to $C_6$ alkyl optionally substituted with at least one substituent selected from the group consisting of halogen,
cyano,
$C_1$ to $C_6$ alkoxy,
$C_3$ to $C_8$ cycloalkyl,
tetrahydrofuryl,
phenyl optionally substituted with at least one substituent selected from the group consisting of halogen and $C_1$ to $C_6$ alkoxy, and
phenoxy optionally substituted with at least one halogen, 2) $C_3$ to $C_8$ cycloalkyl optionally substituted with at least one substituent selected from the group consisting $C_1$ to $C_6$ alkyl and halo($C_1$ to $C_6$ alkyl), 3) phenyl optionally substituted with at least one substituent selected from the group consisting of halogen, cyano, halo($C_1$ to $C_6$ alkyl) and $C_1$ to $C_6$ alkoxy, 4) pyridyl optionally substituted with at least one substituent selected from the group consisting of halogen, cyano, halo($C_1$ to $C_6$ alkyl) and $C_1$ to $C_6$ alkoxy, 5) tetrahydropyranyl.

The term "optionally substituted amino" refers to an amino defined above that can be substituted with one or more of these substituents.

The term "alkylamino" includes mono-alkylamino and di-alkylamino.

The term "aryl" includes phenyl, naphthyl, anthryl, phenanthryl, indenyl and the like. Phenyl is preferable.

The aryl parts of "aryloxy", "aryloxycarbonyl", "arylthio", "arylsulfonyl", "arylalkyl", "arylalkoxy", "alkylaryl", "alkylarylalkyl", "alkoxyaryl", "alkoxyarylalkyl", "aryloxyalkyl", "halogenoaryl", "halogenoarylalkyl", "halogenoaryloxy", "halogenoaryloxyalkyl", "haloalkylaryl" "haloalkylarylalkyl", "haloalkoxyaryl", "haloalkoxyarylalkyl", and "cyanoaryl" are the same as the above "aryl".

The terms "heterocyclyl" or "heterocycle" refer to a heterocyclic group containing at least one heteroatom arbitrarily selected from the group consisting of O, S and N. Suitable heterocyclyl groups are, for example, 5- or 6-membered heteroaryl groups, such as pyrrolyl, imidazolyl, pyrazolyl, pyridyl, pyridazinyl, pyrimidinyl, pyrazinyl, isoxazolyl, oxazolyl, oxadiazolyl, isothiazolyl, thiazolyl, thiadiazolyl, furyl and thienyl; fused heterocyclyl groups having two rings, such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazoropyridyl, imidazothiazolyl, pyrazinopyridazinyl, quinazolinyl, quinolyl, isoquinolyl, naphthyridinyl, tetrahydroquinolyl and tetrahydrobenzothienyl; fused heterocyclyl groups having three rings such as carbazolyl, acridinyl, xanthenyl, phenothiazinyl, phenoxathiinyl, phenoxazinyl and dibenzofuryl; and non-aromatic heterocyclyl such as dioxanyl, thiiranyl, oxiranyl, oxathiolanyl, azetidinyl, thianyl, pyrrolidinyl, pyrrolinyl, imidazolidinyl, imidazolinyl, pyrazolidinyl, pyrazolinyl, piperidyl, piperazinyl, dihydropyridyl, morpholinyl, morpholino, thiomorpholinyl, thiomorpholino, dihydropyridyl, tetrahydrofuryl, tetrahydropyranyl, tetrahydrothiazolyl and tetrahydroisothiazolyl.

The heterocyclyl parts of "heterocyclylalkyl", "heterocyclylsulfonyl", "alkylheterocyclyl", "alkoxyheterocyclyl", "haloalkylheterocyclyl", and "haloalkoxyheterocyclyl" are the same as the above "heterocyclyl".

Examples of the substituents for "optionally substituted aryl" and "optionally substituted heterocyclyl" are 1) the same as those for the above "optionally substituted alkyl", 2) alkyl optionally substituted with at least one substituent selected from the Group A and Group C, 3) oxo and 4) alkylenedioxy.

These substituents may attach to one or more of any possible positions.

The phrase "$R^1$ and $R^2$ can be taken together with the adjacent atoms to form a ring" means

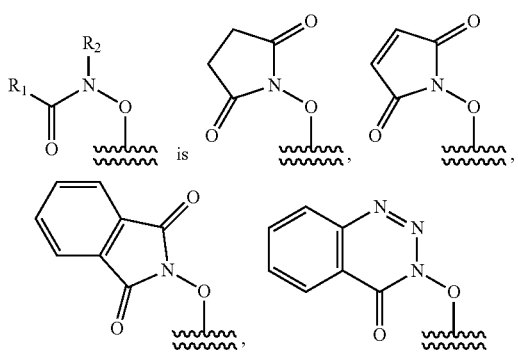
or the like.
The phrase "$R^3$ and $R^4$ can be taken together with the neighboring carbon atom to form a ring" means
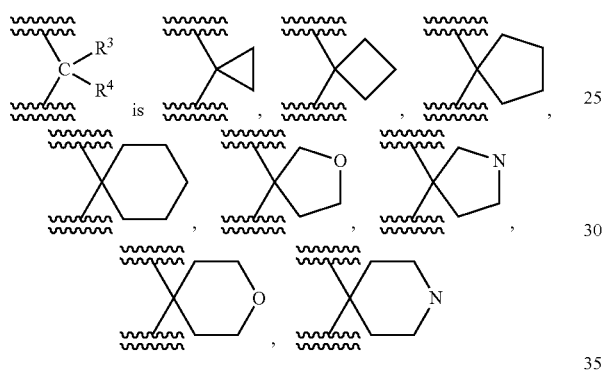
or the like.
When p is 2, each X can be the same or different.
In one embodiment, preferable oxycarbamoyl Compounds are the compounds of the following Formula I:
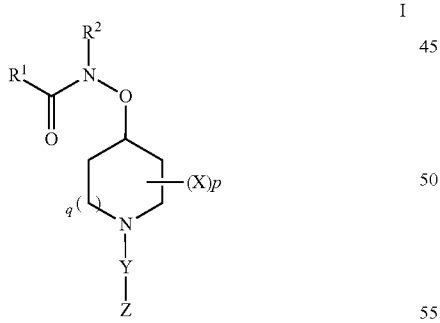
wherein —$R^1$ is selected from the group consisting of
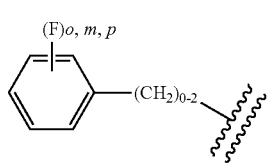
(Ca)
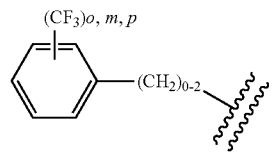
(Cb)
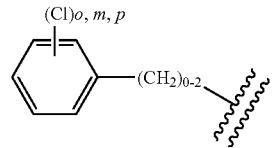
(Cc)
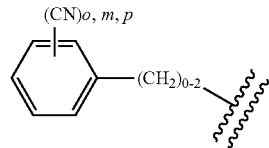
(Cd)
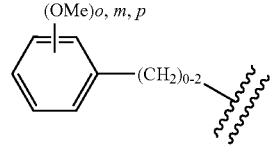
(Ce)
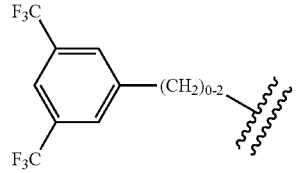
(Cf)
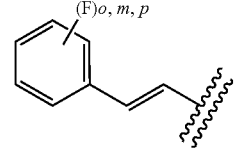
(Cg)
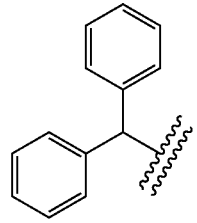
(Ch)
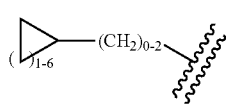
(Ci)
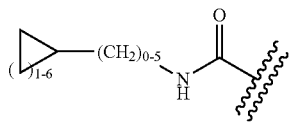
(Cj)
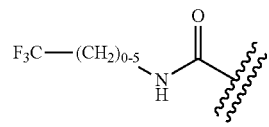
(Ck)

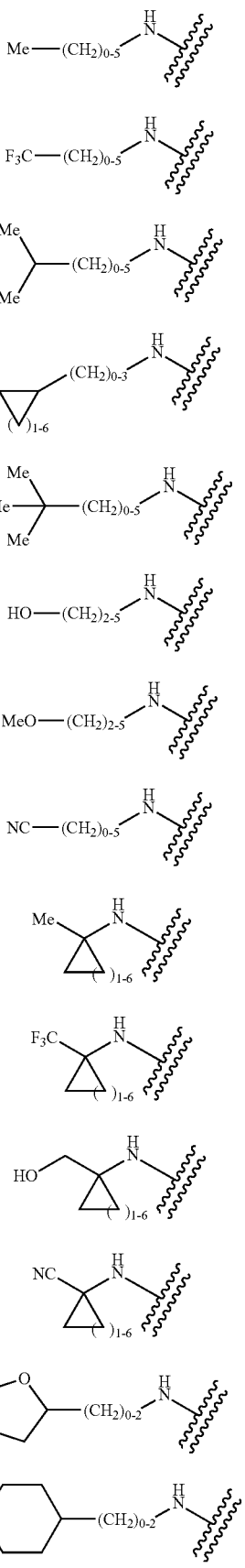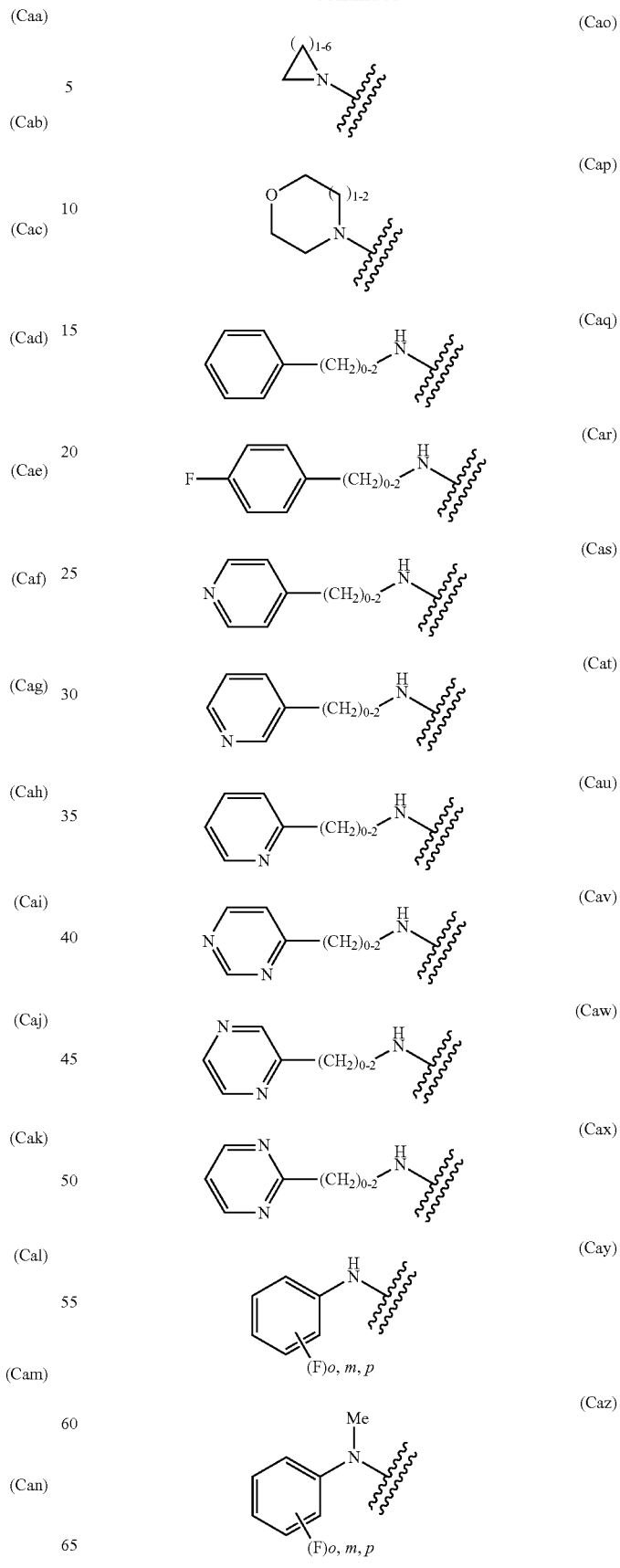

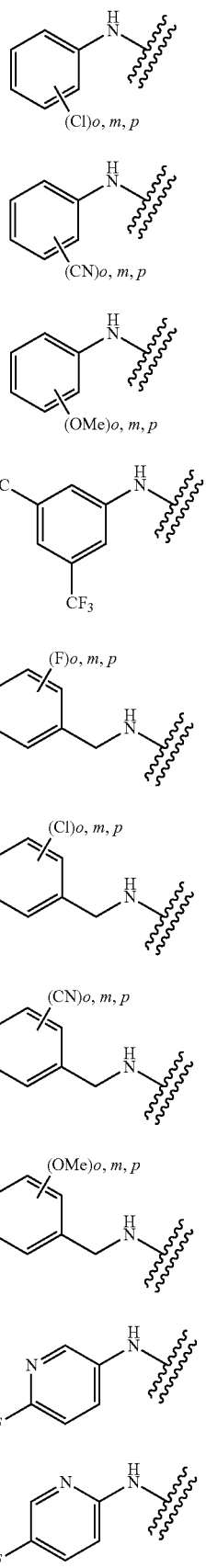
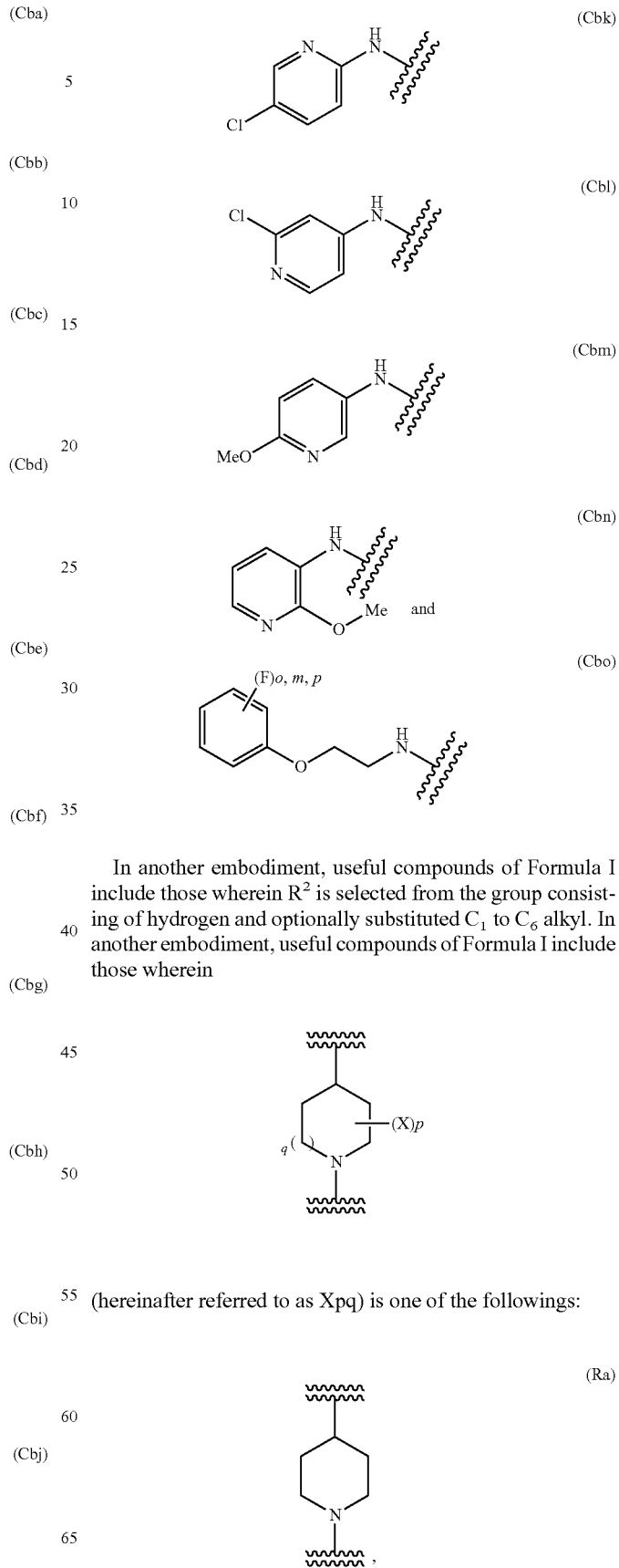
In another embodiment, useful compounds of Formula I include those wherein $R^2$ is selected from the group consisting of hydrogen and optionally substituted $C_1$ to $C_6$ alkyl. In another embodiment, useful compounds of Formula I include those wherein
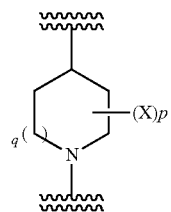
(hereinafter referred to as Xpq) is one of the followings:
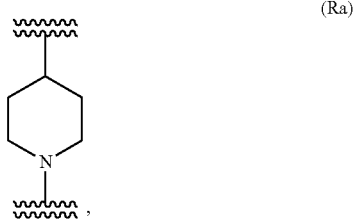

-continued
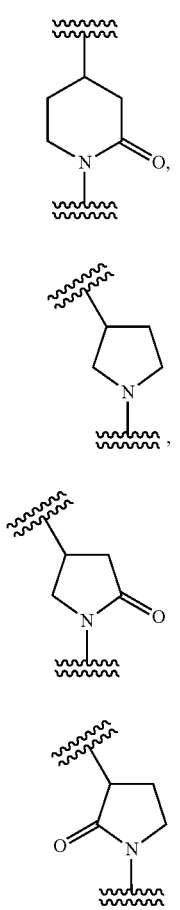
(Rb)
(Rc)
(Rd)
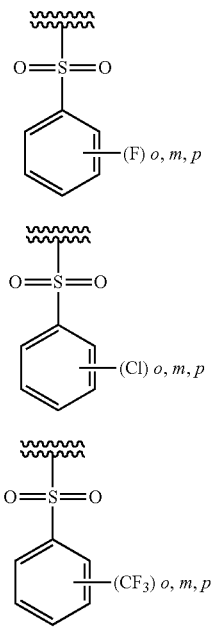 and
(Re)
In another embodiment, useful compounds of Formula I include those wherein Y—Z is one of the following:
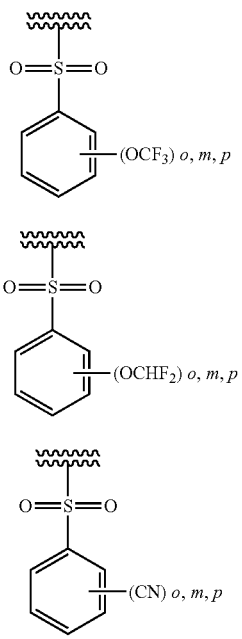
(YZa)
(YZb)
(YZc)
-continued
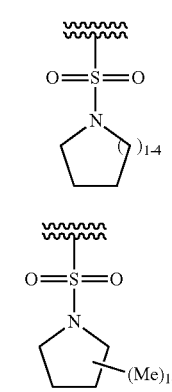
(YZd)
(YZe)
(YZf)
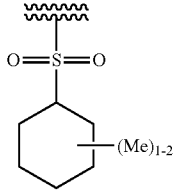
(YZg)
(YZh)
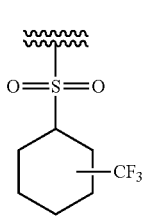
(YZi)
(YZj)
(YZk)

-continued (YZl) 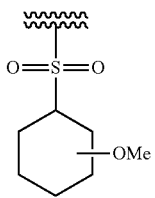

(YZm) 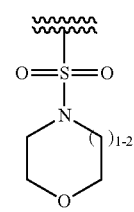

(YZn) 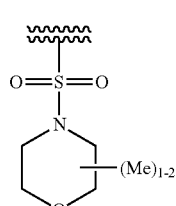

(YZo) 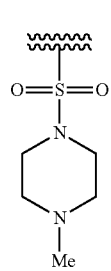

(YZp) 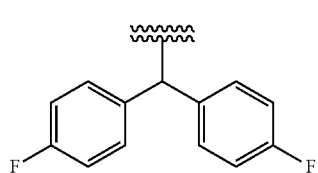

(YZq) 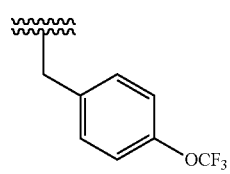

(YZr) 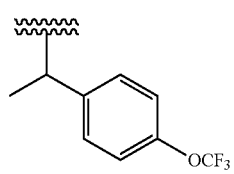

(YZs) 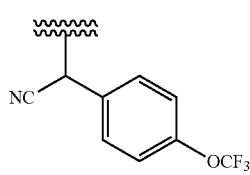

-continued (YZt) 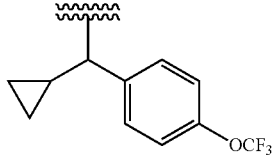

In another embodiment, useful compounds of Formula I include those wherein the combination of =Compound Number, $R^1$, Xpq, and Y—Z (=Compound Number, $R^1$, Xpq, Y—Z) is one of the followings:

(Ia-1,Ca,Ra,YZc),(Ia-2,Cb,Ra,YZc),(Ia-3,Cc,Ra,YZc), (Ia-4,Cd,Ra,YZc),(Ia-5,Cf,Ra,YZc), (Ia-6,Cg,Ra,YZc),(Ia-7,Ch,Ra,YZc),(Ia-8,Ca,Ra,YZd),(Ia-9,Cb,Ra,YZd),(Ia-10,Cc,Ra,YZd),(Ia-11,Cd,Ra,YZd),(Ia-12,Cf,Ra,YZd),(Ia-13,Cg,Ra,YZd),(Ia-14,Ch,Ra,YZd),(Ia-15,Ca,Rc,YZc),(Ia-16,Cb,Rc,YZc),(Ia-17,Cc,Rc,YZc),(Ia-18,Cd,Rc,YZc),(Ia-19,Cf,Rc,YZc),(Ia-20,Cg,Rc,YZc),(Ia-21,Ch,Rc,YZc),(Ia-22,Ca,Rc,YZd),(Ia-23,Cb,Rc,YZd),(Ia-24,Cc,Rc,YZd),(Ia-25,Cd,Rc,YZd),(Ia-26,Cf,Rc,YZd),(Ia-27,Cg,Rc,YZd),(Ia-28,Ch,Rc,YZd),(Ia-29,Caa,Ra,YZc),(Ia-30,Cab,Ra,YZc),(Ia-31,Cad,Ra,YZc),(Ia-32,Cae,Ra,YZc),(Ia-33,Cai,Ra,YZc),(Ia-34,Caj,Ra,YZc),(Ia-35,Caq,Ra,YZc),(Ia-36,Car,Ra,YZc),(Ia-37,Cau,Ra,YZc),(Ia-38, Cay,Ra,YZc),(Ia-39,Caz,Ra,YZc),(Ia-40,Cba,Ra,YZc),(Ia-41,Cbb,Ra,YZc),(Ia-42,Cbc,Ra,YZc),(Ia-43,Cbd,Ra,YZc),(Ia-44,Cbm,Ra,YZc),(Ia-45,Cbo,Ra,YZc),(Ia-46,Caa,Ra,YZd), (Ia-47,Cab,Ra,YZd), (Ia-48,Cad,Ra,YZd),(Ia-49,Cae,Ra,YZd),(Ia-50,Cai,Ra,YZd),(Ia-51,Caj,Ra,YZd),(Ia-52,Caq,Ra,YZd),(Ia-53,Car,Ra,YZd),(Ia-54,Cau,Ra,YZd),(Ia-55,Cay,Ra,YZd),(Ia-56,Caz,Ra,YZd),(Ia-57,Cba,Ra,YZd),(Ia-58,Cbb,Ra,YZd),(Ia-59,Cbc,Ra,YZd),(Ia-60,Cbd,Ra,YZd),(Ia-61,Cbm,Ra,YZd),(Ia-62,Cbo,Ra,YZd),(Ia-63,Caa,Ra,YZg),(Ia-64,Cab,Ra,YZg),(Ia-65,Cad,Ra,YZg),(Ia-66,Cae,Ra,YZg),(Ia-67,Cai,Ra,YZg),(Ia-68,Caj,Ra,YZg), (Ia-69,Caq,Ra,YZg),(Ia-70,Car,Ra,YZg),(Ia-71,Cau,Ra,YZg),(Ia-72,Cay,Ra,YZg),(Ia-73,Caz,Ra,YZg),(Ia-74,Cba,Ra,YZg),(Ia-75,Cbb,Ra,YZg),(Ia-76,Cbc,Ra,YZg),(Ia-77,Cbd,Ra,YZg),(Ia-78,Cbm,Ra,YZg),(Ia-79,Cbo,Ra,YZg),(Ia-80,Caa,Ra,YZi),(Ia-81,Cab,Ra,YZi),(Ia-82,Cad,Ra,YZi),(Ia-83,Cae,Ra,YZi),(Ia-84,Cai,Ra,YZi),(Ia-85,Caj,Ra,YZi),(Ia-86,Caq,Ra,YZi),(Ia-87,Car,Ra,YZi),(Ia-88,Cau,Ra,YZi),(Ia-89,Cay,Ra,YZi),(Ia-90,Caz,Ra,YZi),(Ia-91,Cba,Ra,YZi),(Ia-92,Cbb,Ra,YZi),(Ia-93,Cbc,Ra,YZi),(Ia-94,Cbd,Ra,YZi),(Ia-95,Cbm,Ra,YZi),(Ia-96,Cbo,Ra,YZi),(Ia-97,Caa,Ra,YZk),(Ia-98,Cab,Ra,YZk),(Ia-99,Cad,Ra,YZk), (Ia-100,Cae,Ra,YZk),(Ia-101,Cai,Ra,YZk),(Ia-102,Caj,Ra,YZk),(Ia-103,Caq,Ra,YZk),(Ia-104,Car,Ra,YZk),(Ia-105,Cau,Ra,YZk),(Ia-106,Cay,Ra,YZk),(Ia-107,Caz,Ra,YZk),(Ia-108, Cba,Ra,YZk),(Ia-109,Cbb,Ra,YZk),(Ia-110,Cbc,Ra,YZk),(Ia-111,Cbd,Ra,YZk),(Ia-112,Cbm,Ra,YZk),(Ia-113,Cbo,Ra,YZk),(Ia-114,Caa,Rc,YZc),(Ia-115,Cab,Rc,YZc),(Ia-116,Cad,Rc,YZc),(Ia-117,Cae,Rc,YZc),(Ia-118,Cai,Rc,YZc),(Ia-119,Caj,Rc,YZc),(Ia-120,Caq,Rc,YZc),(Ia-121,Car,Rc,YZc),(Ia-122,Cau,Rc,YZc),(Ia-123,Cay,Rc,YZc),(Ia-124,Caz,Rc,YZc),(Ia-125,Cba,Rc,YZc),(Ia-126,Cbb,Rc,YZc),(Ia-127,Cbc,Rc,YZc),(Ia-128,Cbd,Rc,YZc), (Ia-129,Cbm,Rc,YZc),(Ia-130,Cbo,Rc,YZc),(Ia-131,Caa,Rc,YZd),(Ia-132,Cab,Rc,YZd),(Ia-133,Cad,Rc,YZd),(Ia-134,Cae,Rc,YZd),(Ia-135,Cai,Rc,YZd),(Ia-136,Caj,Rc,YZd),(Ia-137, Caq,Rc,YZd),(Ia-138,Car,Rc,YZd),(Ia-139,Cau,Rc,YZd),(Ia-140,Cay,Rc,YZd),(Ia-141,Caz,Rc,YZd),(Ia-142,Cba,Rc,YZd),(Ia-143,Cbb,Rc,YZd),(Ia-144,Cbc,Rc,YZd),(Ia-145,Cbd,Rc,YZd),(Ia-146,Cbm,Rc,YZd),(Ia-147,Cbo,Rc,YZd),(Ia-

148,Caa,Rc,YZg),(Ia-149,Cab,Rc,YZg),(Ia-150,Cad,Rc, YZg),(Ia-151,Cae,Rc,YZg),(Ia-152,Cai,Rc,YZg),(Ia-153, Caj,Rc,YZg),(Ia-154,Caq,Rc,YZg),(Ia-155,Car,Rc,YZg), (Ia-156,Cau,Rc,YZg),(Ia-157,Cay,Rc,YZg), (Ia-158,Caz, Rc,YZg),(Ia-159,Cba,Rc,YZg),(Ia-160,Cbb,Rc,YZg),(Ia-161,Cbc,Rc,YZg),(Ia-162,Cbd,Rc,YZg),(Ia-163,Cbm,Rc, YZg),(Ia-164,Cbo,Rc,YZg),(Ia-165,Caa,Rc,YZi),(Ia-166, Cab,Rc,YZi),(Ia-167,Cad,Rc,YZi),(Ia-168,Cae,Rc,YZi), (Ia-169,Cai,Rc,YZi),(Ia-170,Caj,Rc,YZi),(Ia-171,Caq,Rc, YZi),(Ia-172,Car,Rc,YZi),(Ia-173,Cau,Rc,YZi),(Ia-174, Cay,Rc,YZi),(Ia-175,Caz,Rc,YZi),(Ia-176,Cba,Rc,YZi),(Ia-177,Cbb,Rc,YZi),(Ia-178,Cbc,Rc,YZi), (Ia-179,Cbd,Rc, YZi),(Ia-180,Cbm,Rc,YZi),(Ia-181,Cbo,Rc,YZi),(Ia-182, Caa,Rc,YZk),(Ia-183,Cab,Rc,YZk),(Ia-184,Cad,Rc,YZk), (Ia-185,Cae,Rc,YZk),(Ia-186,Cai,Rc,YZk),(Ia-187, Caj,Rc, YZk),(Ia-188,Caq,Rc,YZk),(Ia-189,Car,Rc,YZk),(Ia-190, Cau,Rc,YZk),(Ia-191,Cay,Rc,YZk),(Ia-192,Caz,Rc,YZk), (Ia-193,Cba,Rc,YZk),(Ia-194,Cbb,Rc,YZk),(Ia-195,Cbc, Rc,YZk),(Ia-196,Cbd,Rc,YZk),(Ia-197,Cbm,Rc,YZk),(Ia-198,Cbo,Rc,YZk)

In another embodiment, useful compounds of Formula I include those wherein:

$R^1$ is alkyl optionally substituted with aryl, halogenoaryl, alkylaryl, haloalkylaryl, alkoxyaryl, haloalkoxyaryl, aryloxy and/or halogenoaryloxy, alkenyl optionally substituted with aryl, halogenoaryl, alkylaryl, haloalkylaryl, alkoxyaryl, haloalkoxyaryl, aryloxy and/or halogenoaryloxy, amino optionally substituted with alkyl, haloalkyl, cyanoalkyl, cycloalkylalkyl, alkoxyalkyl, haloalkoxyalkyl, arylalkyl, halogenoarylalkyl, alkylarylalkyl, haloalkylarylalkyl, alkoxyarylalkyl, haloalkoxyarylalkyl, aryloxyalkyl, halogenoaryloxyalkyl, heterocyclylalkyl, cycloalkyl, alkylcycloalkyl, haloalkylcycloalkyl, aryl, halogenoaryl, alkylaryl, haloalkylaryl, cyanoaryl, alkoxyaryl, haloalkoxyaryl, heterocyclyl, alkylheterocyclyl, haloalkylheterocyclyl, alkoxyheterocyclyl and/or haloalkoxyheterocyclyl, carbamoyl optionally substituted with alkyl, haloalkyl, cycloalkylalkyl and/or cycloalkyl, cycloalkyl optionally substituted with halogen, alkyl, haloalkyl, alkoxy, haloalkoxy, and/or cyano, aryl optionally substituted with halogen, alkyl, haloalkyl, alkoxy, haloalkoxy, and/or cyano, or heterocyclyl optionally substituted with halogen, alkyl, haloalkyl, alkoxy, haloalkoxy, and/or cyano, Y is $SO_2$ or $CR^3R^4$, $R^3$ and $R^4$ are each independently hydrogen, cyano, alkyl, haloalkyl, aryl or halogenoaryl, or $R^3$ and $R^4$ can be taken together with the neighboring carbon atom to form a ring;

and

Z is aryl optionally substituted with halogen, alkyl, haloalkyl, alkoxy and/or haloalkoxy or heterocyclyl optionally substituted with halogen, alkyl, haloalkyl, alkoxy and/or haloalkoxy.

The invention disclosed herein is also meant to encompass prodrugs of the disclosed compounds. Prodrugs are considered to be any covalently bonded carriers that release the active parent drug in vivo. Non-limiting examples of prodrugs include esters or amides of compounds of Formula I having hydroxy or amino as a substituent, and these can be prepared by reacting such compounds with anhydrides such as succinic anhydride.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, and preferably $^3H$, $^{11}C$, and $^{14}C$. Isotopically-labeled compounds of the present invention can be prepared by methods known in the art.

The present invention is also directed specifically to $^3H$, $^{11}C$, and $^{14}C$ radiolabeled compounds of Formula I as well as their pharmaceutically acceptable salts, prodrugs and solvates, and the use of any such compounds as radioligands for their binding site on the calcium channel. For example, one use of the labeled compounds of the present invention is the characterization of specific receptor binding. Another use of the labeled compounds of the present invention is an alternative to animal testing for the evaluation of structure-activity relationships. For example, the receptor assay may be performed at a fixed concentration of a labeled compound of Formula I and at increasing concentrations of a test compound in a competition assay. For example, tritiated compounds of any of Formula I can be prepared by introducing tritium into the particular compound of Formula I, for example, by catalytic dehalogenation with tritium. This method may include reacting a suitably halogen-substituted precursor of a compound of Formula I with tritium gas in the presence of a suitable catalyst, for example, Pd/C, in the presence or absence of a base. Other suitable methods for preparing tritiated compounds can be found in NPL 6. $^{14}C$-labeled compounds can be prepared by employing starting materials having a $^{14}C$ carbon. Some of the compounds disclosed herein may contain one or more asymmetric centers and may thus give rise to enantiomers, diastereomers, and other stereoisomeric forms. The present invention is meant to encompass the uses of all such possible forms, as well as their racemic and resolved forms and mixtures thereof. The individual enantiomers may be separated according to methods known to those of ordinary skill in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The invention disclosed herein also encompasses the use of all salts of the disclosed compounds, including all non-toxic pharmaceutically acceptable salts thereof of the disclosed compounds. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, hydrofluoride, phosphate, sulfate, nitrate and the like; organic acid salts such as citrate, lactate, tartrate, maleate, fumarate, mandelate, acetate, dichloroacetate, trifluoroacetate, oxalate, formate, succinate, and the like; sulfonates such as methanesulfonate, benzenesulfonate, p-toluenesulfonate and the like; and amino acid salts such as arginate, aspraginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention with a solution of a pharmaceutically acceptable non-toxic base such as sodium hydroxide, potassium hydroxide, choline hydroxide, sodium carbonate and the like.

The invention disclosed herein is also meant to encompass solvates of the disclosed compounds. One type of solvate is a hydrate. Solvates typically do not contribute significantly to the physiological activity or toxicity of the compounds and as such can function as pharmacological equivalents.

Some compounds of the present invention may have one or more of the following characteristics:
  high affinity for calcium ($Ca^{2+}$) channels, especially N-type calcium channels,
  high selectivity to calcium ($Ca^{2+}$) channels, especially N-type calcium channels versus other channels,
  reduced side effect,
  high stability
  high oral absorbability,
  high bioavailability,
  low clearance,
  easily transfers to brain
  long half-life,
  long efficacy of a medicine and/or
  high protein-unbound fraction.

These compounds are considered useful as blockers of calcium ($Ca^{2+}$) channels, especially N-type calcium channels.

Since compounds of Formula I are blockers of calcium ($Ca^{2+}$) channels, a number of diseases and conditions mediated by calcium ion influx can be treated by employing these compounds. Therefore, the present invention provides a method of treating, preventing or ameliorating stroke, neuronal damage resulting from head trauma, epilepsy, pain (e.g., acute pain, chronic pain, which includes but is not limited to, neuropathic pain and inflammatory pain or surgical pain), migraine, a mood disorder, schizophrenia, a neurodegenerative disorder (e.g., Alzheimer's disease, amyotrophic lateral sclerosis (ALS), or Parkinson's disease), depression, anxiety, a psychosis, hypertension, or cardiac arrhythmia. In one embodiment, the invention provides a method of treating pain. In another embodiment, the type of pain treated is chronic pain. In another embodiment, the type of pain treated is neuropathic pain. In another embodiment, the type of pain treated is inflammatory pain. In another embodiment, the type of pain treated is acute pain. In each instance, such method of treatment, prevention, or amelioration require administering to an animal in need of such treatment, prevention or amelioration an amount of a compound of the present invention that is therapeutically effective in achieving said treatment, prevention or amelioration. In one embodiment, the amount of such compound is the amount that is effective as to block calcium channels in vivo.

Chronic pain includes, but is not limited to, neuropathic pain, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (NPL 7).

The inflammatory process is a complex series of biochemical and cellular events activated in response to tissue injury or the presence of foreign substances (NPL 8). Inflammation often occurs at the site of injured tissue, or foreign material, and contributes to the process of tissue repair and healing. The cardinal signs of inflammation include erythema (redness), heat, edema (swelling), pain and loss of function (NPL 8). The majority of patients with inflammatory pain do not experience pain continually, but rather experience enhanced pain when the inflamed site is moved or touched. Inflammatory pain includes, but is not limited to, osteoarthritis and rheumatoid arthritis.

Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present invention is also directed more generally to a method for treating a disorder responsive to the blockade of calcium channels, and particularly the selective blockade of N-type calcium channels, in an animal suffering from said disorder, said method comprising administering to the animal an effective amount of a compound represented by any of defined Formula I, or a pharmaceutically acceptable salt, prodrug or solvate thereof The present invention is also directed to the use of a compound represented by any of defined Formula I, or a pharmaceutically acceptable salt, prodrug or solvate thereof, in the manufacture of a medicament for treating a disorder responsive to the blockade of calcium channels in an animal suffering from said disorder. In one embodiment, the disorder is responsive to the selective blockade of N-type calcium channels.

Furthermore, the present invention is directed to a method of modulating calcium channels, especially N-type calcium channels, in an animal in need thereof, said method comprising administering to the animal at least one compound represented by any of defined Formula I, or a pharmaceutically acceptable salt, prodrug or solvate thereof.

The present invention is also directed to the use of a compound represented by any of defined Formula I, or a pharmaceutically acceptable salt, prodrug or solvate thereof, in the manufacture of a medicament for modulating calcium channels, especially N-type calcium channels, in an animal in need thereof.

Synthesis of Compounds

The compounds of the present invention can be prepared in a number of ways well known to those skilled in the art of organic synthesis. The compounds of the present invention can be synthesized using the methods outlined below, together with methods known in the art of synthetic organic chemistry, or variations thereof as appreciated by those skilled in the art. Preferred methods include, but are not limited to, those described below. The novel compounds of Formula I can be prepared using the reactions and techniques described in this section. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. It is understood by one skilled in the art of organic synthesis that the functionality present on various portions of the starting molecule in a reaction must be compatible with the reagents and reactions proposed. Not all compounds of Formula I falling into a given class may be compatible with some of the reaction conditions required in some of the methods described. Such restrictions to the substituents which are compatible with the reaction conditions will be readily apparent to one skilled in the art and alternative methods can be used. The compounds of Formula I can be prepared by techniques and procedures readily available to one skilled in the art, for example by following the procedures as set forth in the following Schemes. These Schemes are not intended to limit the scope of the invention in any way. All substituents, unless otherwise indicated, are previously defined. The reagents and starting materials are readily available to one skilled in the art.

Purity of compounds was verified by LCMS measurement. LCMS methods are as follows;

(Method A) Column: Phenomemex Luna C18 (4.6×50 mm, 5 micron particle size), Temperature: 50° C., Pressure limit: 400 bar, Monitored at OD 254 nm, reference 360 nm, Flow rate: 2 ml/min.

HPLC Gradient (Buffer A=0.1% $HCO_2H/H_2O$, Buffer B=0.1% $HCO_2H/CH_3CN$)

| Time (min.) | % B |
|---|---|
| 0 | 15 |
| 1.9 | 45 |
| 4.3 | 45 |
| 8.3 | 95 |
| 11.3 | 95 |
| 11.4 | 15 |
| 15.4 | 15 |

(Method B) Column: Discovery HS C18 (4.6×150 mm, 3 micron particle size), Temperature: 25° C., Pressure limit: 400 bar, Monitored at OD 260 nm, reference 360 nm, Flow rate: 1 ml/min.

HPLC Gradient (Buffer A=0.1% $TFA/H_2O$, Buffer B=0.1% $TFA/CH_3CN$)

| Time (min.) | % B |
|---|---|
| 0 | 15 |
| 1.9 | 45 |
| 4.3 | 45 |
| 8.3 | 95 |
| 11.3 | 95 |
| 11.4 | 15 |
| 15.4 | 15 |

(Method C) Column: Phenomemex Luna C18 (4.6×50 mm, 5 micron particle size), Temperature: 50° C., Pressure limit: 344.75 bar, Monitored at OD 254 nm, Flow rate: 3 ml/min.

HPLC Gradient (Buffer A=0.1% $HCO_2H/H_2O$, Buffer B=0.1% $HCO_2H/CH_3CN$)

| Time (min.) | % B |
|---|---|
| 0 | 10 |
| 3.0 | 100 |
| 4.0 | 100 |

In order to generate compounds of Formula I, a multi-step reaction sequence as described in Scheme 1 may be employed. Herein, a suitably N-protected 4-hydroxypiperidine or the corresponding equivalent (1a) is reacted with a suitably N-protected hydroxylamine.

Typically the reaction is effected using standard "Mitsunobu-reaction" conditions, familiar to one skilled in the art, such as diethyl azodicarboxylate/triphenylphosphine.

Deprotection of $P_1$ group of the compound (1b) may be accomplished using standard conditions, familiar to one skilled in the art. The acid (Z—Y—OH, Y: C═O), acid chloride (Z—Y—Cl, Y: C═O), acid anhydride (Z—Y—Z, Y: C═O), sulfonyl chloride (Z—Y—Cl, Y: $SO_2$) or alkyl halide (Z—Y-hal, Y: $CR^3R^4$, hal: Cl, Br or I) may be coupled with amine (1c) by using standard conditions, familiar to one skilled in the art. Deprotection of $P_2$ group of the compound (1d) may be accomplished using standard conditions, familiar to one skilled in the art. The resulting hydroxylamine (1e) may then be coupled with an acid chloride ($R^1COCl$) or a carboxylic acid ($R^1CO_2H$) wherein $R^1$ is described above, using standard amide coupling conditions, familiar to one skilled in the art, such as N-ethyldimethylaminopropylcarbodiimide hydrochloride/1-hydroxybenzotriazole to yield the desired oxycarbamoyl compound (I). The hydroxylamine (1e) may also be coupled with an isocyanate ($R^1NCO$) or an amine ($R^1NH_2$) wherein $R^1$ is described above, using standard urea formation conditions, familiar to one skilled in the art, such as 1,1'-carbonyldiimidazole or trichloromethyl chloroformate to give the desired oxyurea compound (I). An isocyanate ($R^1NCO$) may be also generated in situ from an acid ($R^1CO_2H$) using standard Curtius rearrangement reaction conditions, familiar to one skilled in the art, such as diphenyl phosphorazidate.

An alternative way of preparing some of the compounds of the present invention is detailed in Scheme 2.

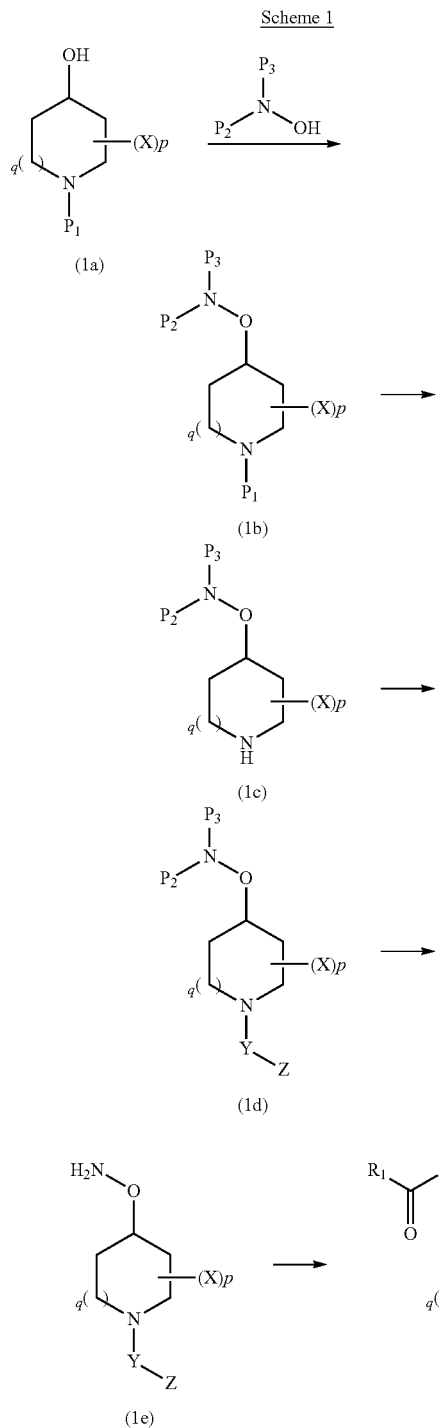

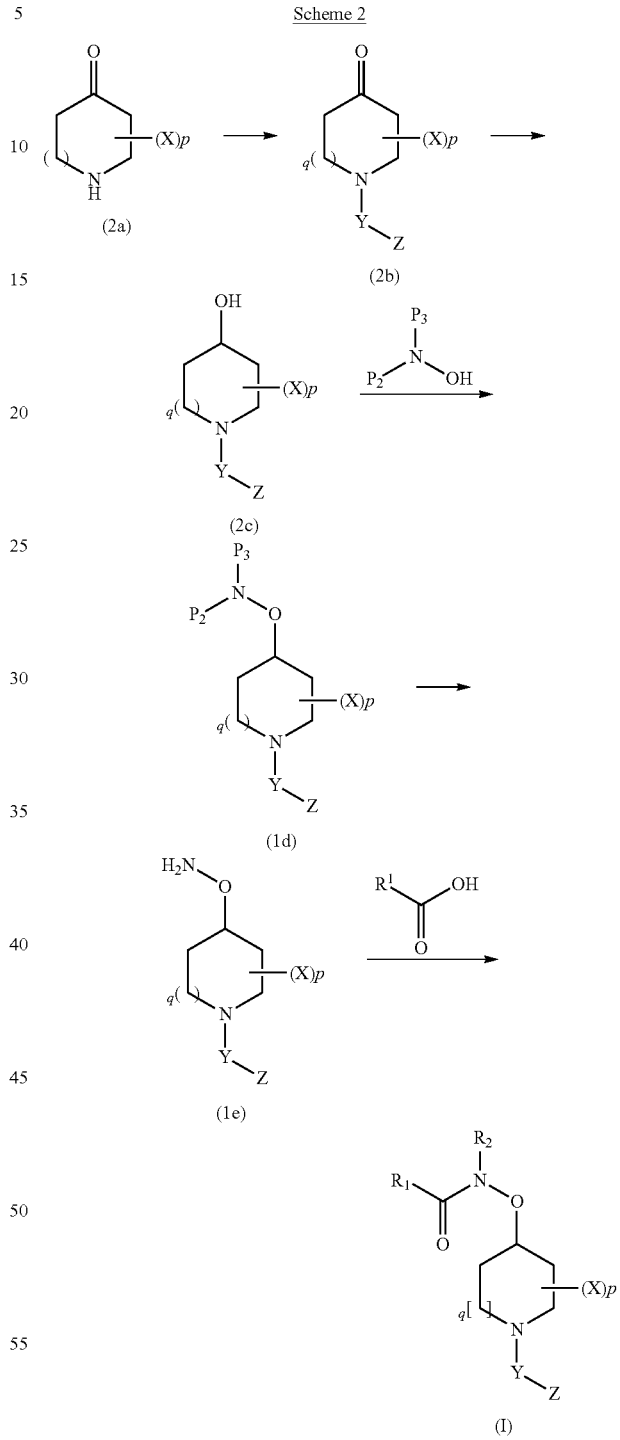

wherein $P_1$ and $P_2$ are each independently an amino protecting group such as t-butoxycarbonyl and the like and $P_3$ is hydrogen, or $P_2$ and $P_3$ taken together, with the nitrogen atom to which they are attached, form phthalimide and the like, and the other symbols are the same as defined above.

wherein $P_2$ is an amino protecting group such as t-butoxycarbonyl and the like and $P_3$ is hydrogen, or $P_2$ and $P_3$ taken together, with the nitrogen atom to which they are attached, form phthalimide and the like, and the other symbols are the same as defined above.

As an alternative to Scheme 1, Scheme 2 employs a piperidone or the corresponding equivalent (2a), which may be coupled with the acid chloride (Z—Y—Cl, Y: C=O), acid anhydride (Z—Y—Z, Y: C=O), sulfonyl chloride (Z—Y—Cl, Y: SO$_2$) or alkyl halide (Z—Y-hal, Y: CR$^3$R$^4$, hal: Cl, Br or I) by using standard conditions, familiar to one skilled in the art. The resultant ketone (2b) can then be reduced to the alcohol (2c). Any conventional method of reducing a ketone to an alcohol may be utilized to effect this conversion. The resulting alcohol reacts with a suitably N-protected hydroxylamine, whereby P$_2$ is, for example, tert-butoxycarbonyl. Typically the reaction is effected using standard "Mitsunobu-reaction" conditions, familiar to one skilled in the art, such as diethyl azodicarboxylate/triphenylphosphine. The resultant compound (1d) can be transformed to the compounds of formula (I) in an analogous manner previously described in Scheme 1.

An alternative way of preparing some of the compounds of the present invention is detailed in Scheme 3.

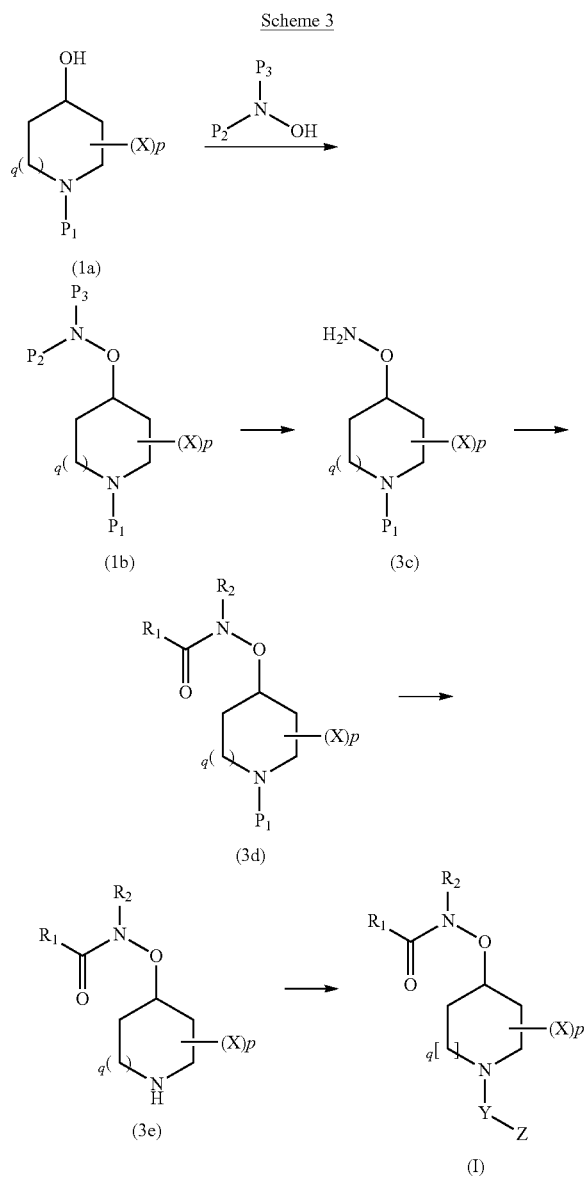

As an alternative to Scheme 1 and 2, Scheme 3 introduces the carbamoyl moiety first into the hydroxylamine (3c). The resulting oxycarbamoyl compound (3d) can be transformed to the compounds of formula (I) in an analogous manner previously described in Scheme 1.

Testing of Compounds

Representative compounds of the present invention were assessed by calcium mobilization and/or electrophysiological assays for calcium channel blocker activity. One aspect of the present invention is based on the use of the compounds herein described as N-type calcium channel blockers. In one aspect of the present invention, it has been found that certain compounds herein described show selectivity as N-type calcium channel blockers. Based upon this property, these compounds are considered useful in treating, preventing, or ameliorating migraine, epilepsy, a mood disorder, schizophrenia, a neurodegenerative disorder (such as, e.g., Alzheimer's disease, ALS, or Parkinson's disease), a psychosis, depression, anxiety, hypertension, or cardiac arrhythmia. The compounds of the present invention are also expected to be effective in treating, preventing or ameliorating pain, such as acute pain, chronic pain, which includes but is not limited to, neuropathic pain and inflammatory pain or surgical pain.

More specifically, the present invention is directed to compounds of Formula I that are blockers of calcium channels. According to the present invention, those compounds having preferred N-type calcium channel blocking properties exhibit an IC$_{50}$ of about 100 μM or less in the calcium mobilization and/or electrophysiological assays described herein. Preferably, the compounds of the present invention exhibit an IC$_{50}$ of 10 μM or less. Most preferably, the compounds of the present invention exhibit an IC$_{50}$ of about 1.0 μM or less. Compounds of the present invention can be tested for their N-type and L-type Ca$^{2+}$ channel blocking activity by the following calcium mobilization and/or electrophysiological assays. In one embodiment, compounds useful in the present invention are those represented by any one of Formula I that exhibit selectivity for N-type calcium channels over L-type calcium channels in the calcium mobilization and/or electrophysiological assays described herein. The phrase "selectivity for N-type calcium channels over L-type calcium channels" is used herein to mean that the ratio of an IC$_{50}$ for L-type channel blocking activity for a compound of the present invention over an IC$_{50}$ for N-type channel blocking activity for the same compound is more than 1, i.e., LTCC IC$_{50}$/NTCC IC$_{50}$>1. Preferably, compounds of the present invention exhibit an LTCC IC$_{50}$/NTCC IC$_{50}$ ratio of about 2 or more, about 10 or more, about 20 or more, about 30 or more, about 50 or more, or about 100 or more.

Calcium Mobilization and Electrophysiological Assay Protocols:

Cell maintenance and differentiation. Unless noted otherwise, cell culture reagents were purchased from Mediatech of Herndon, Md. IMR32 cells (American Type Culture Collection, ATCC, Manassas, Va.) were routinely cultured in growth medium consisting of minimum essential medium containing 10% fetal bovine serum (FBS, Hyclone, Logan, Utah), 100 U/mL penicillin, 100 μg/mL streptomycin, 2 mM L-glutamine, 1 mM sodium pyruvate, and 1×MEM non-essential amino acids. 80-90% confluent flasks of cells were differentiated using the following differentiation medium: Growth medium plus 1 mM dibutyryl cyclic AMP (Sigma, St. Louis, Mo.), and 2.5 μM bromodeoxyuridine (Sigma). Cells were differentiated for 8 days by replacing differentiation medium every 2-3 days. A7r5 (ATCC) cells were maintained and routinely cultured in A7r5 growth medium consisting of Dulbecco's Modified Eagles Medium containing 10% FBS, 100 U/mL penicillin, 100 μg/mL streptomycin, 4 mM L-glutamine, and 0.15% sodium bicarbonate. 80-90% confluent flasks of cells were differentiated using the following differentiation medium: A7r5 Growth Medium plus 1 mM dibutyryl cyclic AMP (Sigma). Cells were differentiated for 8 days by replacing differentiation medium every 2-3 days.

Recombinant human embryonal kidney cells (HEK293, ATCC) stably transfected with either N-type calcium channel (NTCC) subunits (α1b, α2δ, and β3) or L-type calcium channel (LTCC) subunits (α1c, α2δ, and β1) were routinely cultured in growth medium consisting of Dulbecco's Modified Eagles Medium containing 10% FBS, 100 U/mL penicillin, 100 μg/mL streptomycin, 4 mM L-glutamine, 500 μg/mL geneticin (G418), 20 μg/mL Blasticidin S (InVivogen, San Diego, Calif.) and 500 μg/mL zeocin (InVivogen). FLIPR Calcium Mobilization Assay for N-type Calcium Channel. One day prior to performing this assay, differentiated IMR32 cells were treated with 1x CellStripper, and seeded on poly-D-lysine-coated 96-well clear-bottom black plates (Becton Dickinson, Franklin Lakes, N.J.) at 200,000 cells/well. On the day of the assay, the cell plates were washed with IMR32 buffer (127 mM NaCl, 1 mM KCl, 2 mM $MgCl_2$, 700 μM $NaH_2PO_4$, 5 mM $CaCl_2$, 5 mM $NaHCO_3$, 8 mM HEPES, 10 mM glucose, pH 7.4), then pre-stimulated with KCl and loaded as follows: 0.05 mL of IMR32 buffer, 0.05 mL of each compound tested diluted in IMR32 buffer containing 20 μM nitrendipine (Sigma), and 0.1 mL KCl dissolved in IMR32 buffer, plus Fluo-4 were added (3 μM final concentration, Molecular Probes, Eugene, Oreg.). Final test compound concentrations ranged from about 846 pM to about 17 μM, final nitrendipine concentration was 5 μM, and final KCl concentration was 90 mM. After 1 hour, the cells were washed twice with 0.05 mL of each compound tested in nitrendipine-containing IMR32 buffer (no KCl or Fluo-4), and then replaced with 0.1 mL of each compound tested in nitrendipine-containing IMR32 buffer. Plates were then transferred to a Fluorimetric Imaging Plate Reader (FLIPR[96], Molecular Devices, Inc., Sunnyvale, Calif.) for assay. The FLIPR measured basal Fluo-4 fluorescence for 315 seconds (i.e., 5 minutes and 15 seconds), then added 0.1 mL KCl agonist dissolved in IMR32 buffer and measured fluorescence for another 45 seconds. Final test compound concentrations on the cells after FLIPR read ranged from about 846 pM to about 17 μM, final nitrendipine concentration was 5 μM, and final KCl concentration was 90 mM. Data were collected over the entire time course and analyzed using Excel, Graph Pad Prism (version 3.02, Graph Pad, San Diego, Calif.), or an in-house non-linear regression analysis software.

FLIPR Calcium Mobilization Assay for L-type Calcium Channel. One day prior to performing this assay, HEK293 cells stably expressing recombinant rat L-type calcium channel (LTCC) subunits (α1c, α2δ, and β1) were trypsinized, then seeded on poly-D-lysine-coated 96-well clear-bottom black plates (Becton Dickinson, Franklin Lakes, N.J.) at 75,000 cells/well. On the day of the assay, the plates were washed with LTCC wash buffer (127 mM NaCl, 2 mM $MgCl_2$, 700 μM $NaH_2PO_4$, 5 mM $CaCl_2$, 5 mM $NaHCO_3$, 8 mM HEPES, 10 mM glucose, pH 7.4), then loaded with 0.1 mL of LTCC wash buffer containing Fluo-4 (3 μM final concentration, Molecular Probes, Eugene, Oreg.). After 1 hour, the cells were washed with 0.1 mL LTCC wash buffer and resuspended in 0.05 mL LTCC assay buffer (same composition as LTCC wash buffer). Plates were then transferred to a FLIPR[96] for assay. The FLIPR measured basal Fluo-4 fluorescence for 15 seconds, then added 0.05 mL of each compound tested diluted in LTCC assay buffer at final concentrations ranging from about 846 pM to about 17 μM. Fluo-4 fluorescence was then measured for 5 minutes. 0.1 mL KCl agonist dissolved in LTCC assay buffer was then added to the cells to produce a final concentration of 90 mM KCl, and fluorescence was measured for another 45 seconds. Data were collected over the entire time course and analyzed using Excel, Graph Pad Prism, or an in-house regression analysis software. Alternative FLIPR Calcium Mobilization Assay for L-type Calcium Channel.

Alternatively, the following cell line and procedure may be used for the FLIPR calcium mobilization assay for L-type calcium channel. One day prior to performing this assay, differentiated A7r5 cells are trypsinized, then seeded on tissue culture treated 96-well clear-bottom black plates (Becton Dickinson, Franklin Lakes, N.J.) at a dilution of 1:1 from a confluent T150 $cm^2$ flask. On the day of the assay, the plates are washed with A7r5 wash buffer (127 mM NaCl, 2 mM $MgCl_2$, 700 μM $NaH_2PO_4$, 5 mM $CaCl_2$, 5 mM $NaHCO_3$, 8 mM HEPES, 10 mM glucose, pH 7.4), then loaded with 0.1 mL of A7r5 wash buffer containing Fluo-4 (3 μM final concentration, Molecular Probes, Eugene, Oreg.). After 1 hour, the cells are washed with 0.1 mL A7r5 wash buffer and resuspended in 0.05 mL A7r5 assay buffer that is composed of A7r5 wash buffer plus 50 μM valinomycin (Sigma). Plates are then transferred to a FLIPR[96] for assay. The FLIPR measures basal Fluo-4 fluorescence for 15 seconds, then adds 0.05 mL of each compound tested diluted in A7r5 assay buffer at final concentrations ranging from about 846 pM to about 17 μM. Fluo-4 fluorescence is then measured for 5 minutes. 0.1 mL KCl agonist dissolved in A7r5 assay buffer is then added to the cells to produce a final concentration of 90 mM KCl, and fluorescence was measured for another 45 seconds. Data were collected over the entire time course and analyzed using Excel, Graph Pad Prism, or an in-house regression analysis software.

Cloning of N- and L-type calcium channel subunit open reading frame cDNAs. Five cDNAs encoding subunits of the rat N- or L-type calcium channels were cloned by PCR amplification in order to reconstitute functional channels in a heterologous system. These were the alpha1b (α1b), beta1 (β1), beta3 (β3), alpha2delta (α2δ), and alpha1c (α1c) subunit cDNAs. The alpha1b subunit cDNA has been described by NPL 9. The beta1 subunit cDNA has been described by NPL 10. The beta3 subunit cDNA has been described by NPL 11. The alpha2delta subunit cDNA has been described by NPL 12. The alpha1c subunit cDNA has been described by NPL 13.

The 7.0 kb cDNA containing the entire α1b open reading frame (ORF) was PCR amplified as two overlapping cDNA fragments, i.e., a 2.7 kb 5' fragment and a 4.4 kb 3' fragment. The 5' fragment was amplified from rat brain cDNA using primers 1 (SEQ ID NO:1, TABLE 1) and 2 (SEQ ID NO:2, TABLE 1), and the 3' fragment was amplified from rat spinal cord cDNA using primers 3 (SEQ ID NO:3, TABLE 1) and 4 (SEQ ID NO:4, TABLE 1). The two fragments were joined by ligation at a common restriction site to create the entire 7.0 kb cDNA. This ORF encodes the protein isoform generated by alternative splicing termed "+A ΔSFMG ΔET" according to the nomenclature of NPL 14). The entire cDNA was sequenced with redundant coverage on both strands. The cDNA was then inserted into the mammalian expression vector pcDNA6.2DEST (Invitrogen, Carlsbad Calif.) by homologous recombination using the Gateway system (Invitrogen). The 1.8 kb cDNA encoding the β1 subunit, the 1.45 kb cDNA encoding the beta3 subunit, and the 3.3 kb cDNA encoding the alpha2delta subunit were cloned by PCR amplification from rat spinal cord cDNA (β1) or brain cDNA (β3, α2δ). Primers 5 (SEQ ID NO:5, TABLE 1) and 6 (SEQ ID NO:6, TABLE 1) were used for the β1 cDNA amplification; primers 7 (SEQ ID NO:7, TABLE 1) and 8 (SEQ ID NO:8, TABLE 1) were used for the β3 cDNA amplification; and primers 9 (SEQ ID NO:9, TABLE 1) and 10 (SEQ ID NO:10, TABLE 1) were used for the α2δ cDNA amplification. PCR products were subcloned and fully sequenced on both strands. Clones matching the reference sequence (β1: NM_017346; β3: NM_012828; α2δ: M86621) and the gene's GenBank rat genomic DNA sequences were recombined into the mammalian expression vector pcDNA3.2DEST (β1, β3) or pcDNA3.1-Zeo (α2δ), which had been modified to a vector compatible with the Gateway recombination system using the Gateway vector adaptor kit (Invitrogen). Proper recombination was confirmed by sequencing of recombinogenic regions. For β3 expression vector, proper protein expression was confirmed by Western blot analysis of lysates of transfected HEK293 cells using a rabbit polyclonal antiserum directed against the rat β3 subunit (USA Biological).

The 6.5 kb cDNA encoding the L-type calcium channel α1c subunit was cloned by PCR amplification from rat heart cDNA using primers 11 (SEQ ID NO:11, TABLE 1) and 12 (SEQ ID NO:12, TABLE 1). The PCR fragment was subcloned and fully sequenced on both strands to confirm its identity. A clone matching consensus reference sequence M59786 and rat genomic DNA sequences was recombined into the mammalian expression vector pcDNA6.2DEST. Sequences around the recombinogenic region were sequenced to confirm accurate recombination into the expression vector.

TABLE 1

| PRIMER SEQUENCE | SEQ ID NO. |
|---|---|
| CACC ATG GTC CGC TTC GGG GAC | 1 |
| CCG TTC AGT GGC CTC CTC C | 2 |
| C TAG CAC CAG TGA TCC TGG TCTG | 3 |
| AGT GCG TTG TGA GCG CAG TA | 4 |
| CAC CAT GGT CCA GAA GAG CGG | 5 |
| TCTCAGCGGATGTAGACGCCT | 6 |
| CAC CAT GTA TGA CGA CTC CTA C | 7 |
| GGT GGT CAG TAG CTG TCC TTA GG | 8 |
| CAC CAT GGC TGC TGG CTG CCT | 9 |
| AGA GGG TCA CCA TAG ATA GTG TCT G | 10 |
| CACCATGATTCGGGCCTTCGCT | 11 |
| AGCCTGCGGACTACAGGTTGCTGAC | 12 |

N-type Recombinant Cell Line Development. N-type calcium channel expressing HEK-293 cells were created in two stages. Stage 1 was created as follows. The rat α1b, and β3 cDNA expression constructs (2.5 μg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 μg/mL blasticidin and 500 μg/mL geneticin, and incubated for 3 weeks at 37° C., 5% $CO_2$, 95% humidity. Plates containing ≦1 clone per well were cultured until wells positive for single clones were confluent. Individual clones were then arrayed into columns of a destination 96-well plate, and partly split into 6-well plates for culture maintenance. Array plates were washed once with IMR32 buffer and cells loaded for 1 hour with 0.1 mL of IMR32 buffer containing Fluo-4 (3 μM final concentration, Molecular Probes). Then they were washed twice with 0.1 mL of IMR32 buffer, and replaced with 0.1 mL IMR32 buffer. Plates were then transferred to a FLIPR[96] for assay. The FLIPR measured basal Fluo-4 fluorescence for 315 seconds, then added 0.1 mL KCl agonist dissolved in IMR32 buffer and measured fluorescence for another 45 seconds. Final KCl concentration was 90 mM. Data were collected over the entire time course and analyzed using Excel, Graph Pad Prism, or Activity Base (version 5.1, IDBS, Parsippany, N.J.) software. The clone with the greatest signal-to-noise ratio, best stability of response with passage number, and best adhesion to PDL precoated plates (Becton Dickinson) was expanded, characterized and used for stage 2 cell line development. Stage 2 of N-type cell line development was carried out as follows. The rat α2δ cDNA expression construct (5 μg each) was transfected into the stage 1 N-type clonal cell line by Lipofectamine Plus reagent (Invitrogen), as per manufacturer's instructions. 24 hours later, cells were split in limiting dilution into multiple 96-well plates in selection media containing 20 μg/mL blasticidin, 500 μg/mL geneticin, and 250 μg/mL zeocin and incubated for 3 weeks at 37° C., 5% $CO_2$, 95% humidity. Plates containing ≦1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded, characterized and tested in electrophysiology for the best current size, N-type pharmacology, N-type characteristic current-voltage relationship and kinetics as described below.

L-type Recombinant Cell Line Development. L-type calcium channel expressing HEK-293 cells were created in two stages. Stage 1 was created as follows. The rat α1c, and β1 cDNA expression constructs (2.5 μg each) were co-transfected into human embryonic kidney (HEK-293) cells by Lipofectamine Plus reagent (Invitrogen), as per manufacturer's instructions. 24 hours later, cells were split in limiting dilution into multiple 96-well plates in selection media containing 20 μg/mL blasticidin and 500 μg/mL geneticin, and incubated for 3 weeks at 37° C., 5% $CO_2$, 95% humidity. Plates containing ≦1 clone per well were cultured until wells positive for single clones were confluent. Individual clones were then arrayed into columns of a destination 96-well plate, and partly split into 6-well plates for culture maintenance. Array plates were washed once with LTCC wash (or assay) buffer and cells loaded for 1 hour with 0.1 mL of LTCC buffer containing Fluo-4 (3 μM final concentration, Molecular Probes). Then they were washed twice with 0.1 mL of LTCC buffer, and replaced with 0.1 mL LTCC buffer. Plates were then transferred to a FLIPR[96] for assay. The FLIPR measured basal Fluo-4 fluorescence for 315 seconds, then added 0.1 mL KCl agonist dissolved in LTCC buffer and measured fluorescence for another 45 seconds. Final KCl concentration was 90 mM. Data were collected over the entire time course and analyzed using Excel, Graph Pad Prism, or Activity Base software. The clone with the greatest signal-to-noise ratio, best stability of response with passage number, and best adhesion to PDL precoated plates (Becton Dickinson) was expanded, characterized and used for stage 2 cell line development.

Stage 2 of L-type cell line development was carried out as follows. The rat α2δ cDNA expression construct (5 μg each) was transfected into the stage 1 L-type clonal cell line by Lipofectamine Plus reagent (Invitrogen), as per manufacturer's instructions. 24 hours later, cells were split in limiting dilution into multiple 96-well plates in selection media containing 20 μg/mL blasticidin, 500 μg/mL geneticin, and 250 μg/mL zeocin and incubated for 3 weeks at 37° C., 5% $CO_2$, 95% humidity. Plates containing ≦1 clone per well were cultured and handled according to the same steps and procedures described above for the stage 1 cell line. The three clones with the greatest signal-to-noise, best stability of response with passage number, and best adhesion to PDL precoated plates (Becton Dickinson) were expanded and characterized.

N-type Electrophysiology in Recombinant Cells. For electrophysiological recording, the cells expressing α1b, β3 and α2δ subunits were seeded on 35-mm culture Petri dishes at a density of approximately $10^4$ cells/dish and kept in an incubator for up to three days for subsequent recordings. For recordings, the dishes were positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings were made using conventional patch-clamp techniques (NPL 15) at room temperature (22-24° C.). The patch-clamp pipettes were pulled from WPI, thick-walled borosilicate glass (WPI, Sarasota, Fla.). Currents were recorded using an Axopatch 200A amplifier (Axon Instruments, Union City, Calif.) and were leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes were back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranged from 2 to 3 MOhm and was compensated by 75-80% by the built-in electronic circuitry.

Currents were elicited by stepping from a holding potential of −90 mV to 0 mV for 20 ms every 20 sec. At the −90 mV membrane voltage about 50% of channels were in the inactivated state, and thus contact with a blocker would involve interaction with both resting and inactivated channels. Every drug was applied at 3 to 4 concentrations increasing in a cumulative manner. Fractional inhibition levels in steady-state were used to draw the partial inhibition concentration curves to get the $IC_{50}$ (i.e. concentration causing 50% reduction in the size of the response) values at −90 mV.

Stock solutions of each test compound were prepared using DMSO. Serial dilutions to desired concentrations were done with bath solution; concentration of DMSO in final solutions was 0.1%. Drugs were applied by gravity flow using a plane multi-barrel array shooter positioned 0.5 mm apart from the cell.

All curve fittings were carried out using Origin software (version 5.0, Microcal). A Hill equation was fit to the concentration-inhibition curves to determine $IC_{50}$ values. N-type Electrophysiology in Neuronal Cells. To determine dissociation constants in resting versus inactivated state for N-type calcium channels, neuronal cells that endogenously express N-type calcium channels can be used. For electrophysiological recording, the neuronal cells expressing N-type calcium channels are seeded on 35-mm culture Petri dishes at a density of approximately $10^4$ cells/dish and kept in an incubator for up to three days for subsequent recordings. For recordings, the dishes are positioned on the stage of an inverted microscope (Nikon, Eclipse E600, Japan) and superfused with a bath solution comprised of $BaCl_2$ (11 mM), $MgCl_2$ (1.5 mM), HEPES (10 mM), TEA chloride (120 mM), glucose (10 mM) adjusted to pH 7.4 with KOH. Whole-cell voltage-clamp recordings are made using conventional patch-clamp techniques (NPL 15) at room temperature (22-24° C.). The patch-clamp pipettes are pulled from WPI, thick-walled borosilicate glass (WPI, Sarasota, Fla.). Currents are recorded using an Axopatch 200A amplifier (Axon Instruments, Union City, Calif.) and leak-subtracted (P/4), low-pass filtered (1 kHz, 4-pole Bessel), digitized (20-50-μs intervals), and stored using Digidata 1200 B interface and Pclamp8.0/Clampex software (Axon Instruments, Union City, Calif.). The pipettes are back-filled with internal solution containing CsCl (110 mM), $MgCl_2$ (3 mM), EGTA (3 mM), HEPES (40 mM), Mg-ATP (4 mM), $Na_2GTP$ (0.5 mM), and adjusted to pH 7.2 with CsOH. The pipette resistance ranges from 2 to 3 MOhm and is compensated by 75-80% by the built-in electronic circuitry.

Currents are elicited by stepping from a holding potential of −90 mV to 0 mV for 20 ms every 10 sec. At the −90 mV membrane voltage a proportion of channels is in the inactivated state, and thus contact with a blocker would involve interaction with both resting and inactivated channels. This protocol is used as a first tier screen. For dissection of two components of inhibition (resting block with the apparent dissociation constant $K_r$ and inactivated state block with $K_i$), steady-state inactivation curves are collected using a double-pulse protocol. Three-second long depolarizing pre-pulse incrementing in 10 mV steps is followed by a 10 ms test pulse to 0 mV.

Stock solutions of each test compound are prepared using DMSO. Serial dilutions to desired concentrations are done with bath solution; concentration of DMSO in final solutions is 0.1%. Drugs are applied by gravity flow using a plane multi-barrel array shooter positioned ~1 mm apart from the cell.

All curve fittings can be carried out using Origin software (version 5.0, Microcal). A Hill equation is used to fit the concentration-response curves and to determine $IC_{50}$ values. A Boltzman equation is used to fit inactivation curves, returning half-inactivation voltage, $V_{0.5}$, slope p and the amplitude of current at the most negative voltage where eventually all channels are in the resting state. These parameters are used to calculate the apparent dissociation constants: $K_r=((Ab/Ac)/(1-(Ab/Ac))*[b])$ where [b] is the drug concentration, Ac is the maximum test current amplitude in control conditions and Ab is the maximum test current amplitude in the presence of a blocker; $K_i=[b]/((exp(-(dx/p))*(1+([b]/K_r))-1)$ where dx is the difference between half-inactivation voltage $V_{0.5}$ in the presence and absence of drug and p is the slope.

In Vivo Pharmacology

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

The compounds can be tested for their antinociceptive activity in the formalin model as described in NPL 16. Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period mice are weighed and given either the compound of interest administered i.p. or p.o., or the appropriate volume of vehicle (for example, 10% Tween-80 or 0.9% saline) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value<0.05 is considered significant. Compounds are considered to be efficacious for treating acute and chronic pain if they have activity in blocking both the early and second phase of formalin-induced paw-licking activity.

Compounds can be tested for their potential to treat chronic pain (i.e., antiallodynic and antihyperalgesic activities) using the Chung model of peripheral neuropathy (NPL 17). Male Sprague-Dawley rats weighing between 200-225 g are anesthetized with halothane (1-3% in a mixture of 70% air and 30% oxygen), and their body temperature controlled during anesthesia through use of a homeothermic blanket. A 2-cm dorsal midline incision is then made at the L5 and L6 level, and the para-vertebral muscle groups retracted bilaterally. L5 and L6 spinal nerves are then exposed, isolated, and tightly ligated with 6-0 or 7-0 silk suture. A sham operation is performed exposing the contralateral L5 and L6 spinal nerves, without ligating, as a negative control.

Tactile Allodynia: Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia: Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (NPL 18). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both the injured and non-injured paw. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Pharmaceutical Compositions

Although a compound of the present invention may be administered to a mammal in the form of a raw chemical without any other components present, the compound is preferably administered as part of a pharmaceutical composition containing the compound combined with a suitable pharmaceutically acceptable carrier. Such a carrier can be selected from pharmaceutically acceptable excipients and auxiliaries.

Compositions within the scope of the present invention include all compositions where a compound of the present invention is combined with a pharmaceutically acceptable carrier. In a preferred embodiment, the compound is present in the composition in an amount that is effective to achieve its intended therapeutic purpose. While individual needs may vary, a determination of optimal ranges of effective amounts of each compound is within the skill of the art. Typically, the compounds may be administered to mammal, e.g. human, orally at a dose of from about 0.0025 to about 1500 mg per kg body weight of the mammal, or an equivalent amount of a pharmaceutically acceptable salt thereof, per day to treat the particular disorder. A useful oral dose of a compound of the present invention administered to a mammal is from about 0.0025 to about 50 mg per kg body weight of the mammal, or an equivalent amount of the pharmaceutically acceptable salt thereof. For intramuscular injection, the dose is typically about one-half of the oral dose.

A unit oral dose may comprise from about 0.01 to about 50 mg, and preferably about 0.1 to about 10 mg, of the compound. The unit dose can be administered one or more times daily as one or more tablets, each containing from about 0.01 to about 50 mg of the compound, or an equivalent amount of a pharmaceutically acceptable salt or solvate thereof.

In one embodiment, a pharmaceutical composition of the present invention can be administered orally and is formulated into tablets, dragees, capsules or an oral liquid preparation.

Alternatively, a pharmaceutical composition of the present invention can be administered rectally, and is formulated in suppositories.

Alternatively, a pharmaceutical composition of the present invention can be administered by injection.

Alternatively, a pharmaceutical composition of the present invention can be administered transdermally.

Alternatively, a pharmaceutical composition of the present invention can be administered by inhalation or by intranasal administration.

Alternatively, a pharmaceutical composition of the present invention can be administered by the intravaginal route.

A pharmaceutical composition of the present invention can contain from about 0.01 to 99 percent by weight, and preferably from about 0.25 to 75 percent by weight, of active compound(s).

The present methods of the invention, such as the method for treating, preventing, or ameliorating a disorder responsive to the blockade of calcium channels in an animal in need thereof, can further comprise administering a second therapeutic agent to the animal being administered a compound of Formula I. In one embodiment, the second therapeutic agent is administered in an effective amount.

Effective amounts of the other therapeutic agents are known to those skilled in the art. However, it is well within the skilled artisan's purview to determine the other therapeutic agent's optimal effective-amount range. In one embodiment of the invention, where another therapeutic agent is administered to an animal, the effective amount of the compound of the present invention is less than its effective amount would be where the other therapeutic agent is not administered. In this case, without being bound by theory, it is believed that compounds of the present invention and the other therapeutic agent act synergistically to treat, prevent, or ameliorate a disorder or condition.

The second therapeutic agent can be, but is not limited to, an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, and mixtures thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include nonsteroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxipinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see NPL 19 and NPL 20 which are hereby incorporated by reference in their entireties. Suitable Cox-II inhibitors and 5-lipoxygenase inhibitors, as well as combinations thereof, are described in PTL 4, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating or preventing an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating or preventing Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating or preventing epilepsy or seizure include, but are not limited to, carbamazepine, ethosuximide, gabapentin, lamotrigine, phenobarbital, phenytoin, primidone, valproic acid, trimethadione, benzodiazepines, gamma-vinyl GABA, acetazolamide, and felbamate.

Examples of useful therapeutic agents for treating or preventing stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating or preventing a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating or preventing psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating or preventing ALS include, but are not limited to, baclofen, neurotrophic factors, riluzole, tizanidine, benzodiazepines such as clonazepan and dantrolene.

Examples of useful therapeutic agents for treating or preventing cognitive disorders include, but are not limited to, agents for treating or preventing dementia such as tacrine; donepezil; ibuprofen; antipsychotic drugs such as thioridazine and haloperidol; and antidepressant drugs such as those given below.

Examples of useful therapeutic agents for treating or preventing a migraine include, but are not limited to, sumatriptan; methysergide; ergotamine; caffeine; and beta-blockers such as propranolol, verapamil, and divalproex.

Examples of useful therapeutic agents for treating or preventing vomiting include, but are not limited to, 5-HT3 receptor antagonists such as odansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating or preventing dyskinesia include, but are not limited to, reserpine and tetrabenazine.

Examples of useful therapeutic agents for treating or preventing depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate. A compound of the present invention and the second therapeutic agent can act additively or, in one embodiment, synergistically. In one embodiment, a compound of the present invention is administered concurrently with the second therapeutic agent; for example, a composition comprising an effective amount of a compound of Formula I, and an effective amount of a second therapeutic agent can be administered. Alternatively, a composition comprising an effective amount of a compound of Formula I and a different composition comprising an effective amount of a second therapeutic agent can be concurrently administered. In another embodiment, an effective amount of a compound of the present invention is administered prior or subsequent to administration of an effective amount of the second therapeutic agent. In this embodiment, the compound of the present invention is administered while the second therapeutic agent exerts its therapeutic effect, or the other therapeutic agent is administered while the compound of the present invention exerts its preventive or therapeutic effect for treating, ameliorating or preventing a disorder or condition.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the parenteral, subcutaneous, intravenous, intramuscular, intraperitoneal, transdermal, intranasal, rectal, intravaginal or buccal route, or by inhalation. Alternatively, or concurrently, administration can be by the oral route. The dosage administered and route of administration will vary, depending upon the circumstances of the particular subject, and taking into account such factors as age, health, and weight of the recipient, condition or disorder to be treated, kind of concurrent treatment, if any, frequency of treatment, and the nature of the effect desired.

A pharmaceutical composition of the present invention is preferably manufactured in a manner which is itself known, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores. Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound may be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLES

Example 1

4-Fluoro-N-(1-(3-(trifluoromethyl)phenylsulfonyl)piperidin-4-yloxy)benzamide

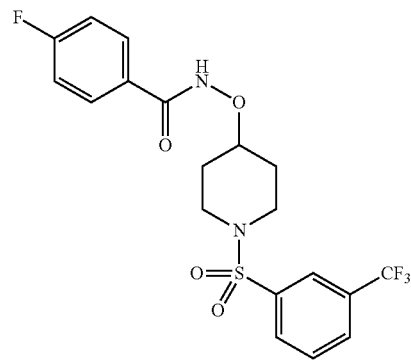 [SMILES: O=C(NOC1CCN(S(=O)(=O)c2cccc(C(F)(F)F)c2)CC1)c1ccc(F)cc1]

a) Diethyl azodicarboxylate (17.4 g, 100 mmol) was added to a solution of tert-butyl 4-hydroxypiperidine-1-carboxylate (7.50 g, 37.3 mmol), 2-hydroxyisoindoline-1,3-dione (6.08 g, 37.3 mmol) and triphenylphosphine (19.6 g, 74.6 mmol) in tetrahydrofuran (100 ml) at 0° C. The reaction mixture was stirred at room temperature for 17 hours and concentrated in vacuo. The residue was purified by column chromatography (ethyl acetate/petroleum ether: 5/95 to 12.5/87.5) to give tert-butyl 4-(1,3-dioxoisoindolin-2-yloxy)piperidine-1-carboxylate (5.81 g, 45%) as a white solid: LCMS: 247 [M+1]$^+$.

b) tert-Butyl 4-(1,3-dioxoisoindolin-2-yloxy)piperidine-1-carboxylate (3.81 g, 11.0 mmol) was added to trifluoroacetic acid (80 ml) and the mixture was stirred at room temperature for 30 minutes. The reaction was concentrated in vacuo and the residue was triturated with diethyl ether (100 ml). The resulting solid was washed with diethyl ether (20 ml×3) to give 2-(piperidin-4-yloxy)isoindoline-1,3-dione trifluoroacetic acid (3.50 g, 90%) as a white solid: LCMS: 247 [M+1]⁺.

c) 3-(Trifluoromethyl)benzenesulfonyl chloride (3.23 g, 13.2 mmol) was added to a solution of 2-(piperidin-4-yloxy) isoindoline-1,3-dione trifluoroacetic acid (3.56 g, 9.80 mmol) and N,N-diisopropylethylamine (7.10 g, 55.0 mmol) in CH₂Cl₂ (85 ml), and stirred at room temperature for 17 hours. The reaction mixture was washed with aqueous 1 N HCl solution (20 ml×3), aqueous NaHCO₃ solution (20 ml×3), brine (20 ml×2), dried over Na₂SO₄, filtered and concentrated in vacuo to give 2-(1-(3-(trifluoromethyl)phenylsulfonyl)piperidin-4-yloxy)isoindoline-1,3-dione (4.12 g, 93%) as a white solid: LCMS: 454 [M+1]⁺.

d) A solution of 2-(1-(3-(trifluoromethyl)phenylsulfonyl)piperidin-4-yloxy)isoindoline-1,3-dione (4.85 g, 10.0 mmol) and hydrazine monohydrate (550 mg, 11.0 mmol) in ethanol (30 ml) was stirred at room temperature for 30 minutes. The resulting solid was filtered off and concentrated in vacuo. The residue was triturated with diethyl ether (80 ml), and the resulting solid was filtered off again and concentrated in vacuo to give O-(1-(3-(trifluoromethyl)phenylsulfonyl)piperidin-4-yl)hydroxylamine (3.00 g, 93%) as a white solid: LCMS: 325 [M+1]⁺.

e) 1-(3-Dimethylaminopropyl)-3-ethylcarboiimide hydrochloride (138 mg, 0.72 mmol) was added to a solution of O-(1-(3-(trifluoromethyl)phenylsulfonyl)piperidin-4-yl)hydroxylamine (195 mg, 0.60 mmol), 1-hydroxybenzotriazole (97.0 mg, 0.72 mmol), 4-fluorobenzoic acid (84.0 mg, 0.60 mmol) and N,N-diisopropylethylamine (233 mg, 1.80 mmol) in N,N-dimethylformamide (8 ml). The reaction mixture was stirred at room temperature for 17 hours and quenched with H₂O (50 ml) and aqueous 1 N HCl solution (pH=3). The aqueous phase was extracted with CH₂Cl₂ (20 ml×3) and the combined organic phase was washed with aqueous NaHCO₃ solution and brine, dried over Na₂SO₄, filtered and concentrated in vacuo. The residue was purified by column chromatography (ethyl acetate/petroleum ether: 50/50) to give 4-fluoro-N-(1-(3-(trifluoromethyl)phenylsulfonyl)piperidin-4-yloxy)benzamide (217 mg, 81%) as a white solid: LCMS: 447 [M+1]⁺. ¹H NMR (DMSO-d₆) δ: 1.71 (m, 2H), 1.88 (m, 2H), 3.07 (m, 4H), 3.97 (t, 1H), 7.27 (t, 2H), 7.74 (m, 2H), 7.98 (m, 2H), 8.10 (m, 2H), 11.4 (s, 1H).

Example 2

3-(Trifluoromethyl)-N-(1-(3-(trifluoromethyl)phenylsulfonyl)piperidin-4-yloxy)benzamide was prepared as described in EXAMPLE 1

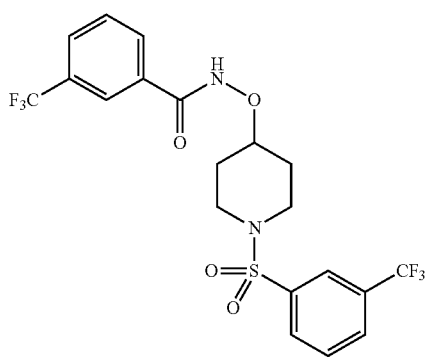 [SMILES: O=C(NOC1CCN(S(=O)(=O)c2cccc(C(F)(F)F)c2)CC1)c1cccc(C(F)(F)F)c1]

white solid: LCMS: 497 [M+1]⁺. ¹H NMR (DMSO-d₆) δ: 1.74 (m, 2H), 1.89 (m, 2H), 3.04 (m, 2H), 3.14 (m, 2H), 4.00 (t, 1H), 7.70 (t, 1H), 7.94 (m, 5H), 8.10 (m, 2H), 11.7 (s, 1H).

Example 3

2-(4-Fluorophenyl)-N-(1-(3-(trifluoromethyl)phenylsulfonyl)piperidin-4-yloxy)acetamide was prepared as described in EXAMPLE 1

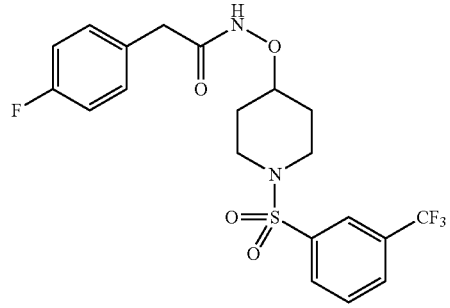 [SMILES: O=C(Cc1ccc(F)cc1)NOC1CCN(S(=O)(=O)c2cccc(C(F)(F)F)c2)CC1]

white solid: LCMS: 461 [M+1]⁺. ¹H NMR (DMSO-d₆) δ: 1.64 (m, 2H), 1.81 (m, 2H), 3.03 (m, 4H), 3.24 (m, 2H), 3.82 (m, 1H), 7.19 (m, 4H), 7.90 (m, 2H), 8.09 (m, 2H), 11.0 (s, 1H).

Example 4

2-(3-(Trifluoromethyl)phenyl)-N-(1-(3-(trifluoromethyl)phenylsulfonyl)piperidin-4-yloxy)acetamide was prepared as described in EXAMPLE 1

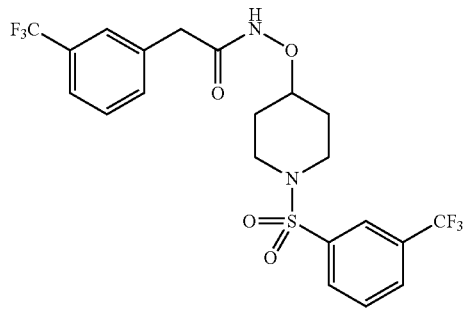 [SMILES: O=C(Cc1cccc(C(F)(F)F)c1)NOC1CCN(S(=O)(=O)c2cccc(C(F)(F)F)c2)CC1]

white solid: LCMS: 511 [M+1]⁺. ¹H NMR (DMSO-d₆) δ: 1.61 (m, 2H), 1.81 (m, 2H), 3.02 (m, 4H), 3.37 (s, 2H), 3.82 (m, 1H), 7.54 (m, 4H), 7.90 (m, 2H), 8.08 (m, 2H), 11.1 (s, 1H).

Example 5

3-(4-Fluorophenyl)-N-(1-(3-(trifluoromethyl)phenylsulfonyl)piperidin-4-yloxy)propanamide was prepared as described in EXAMPLE 1

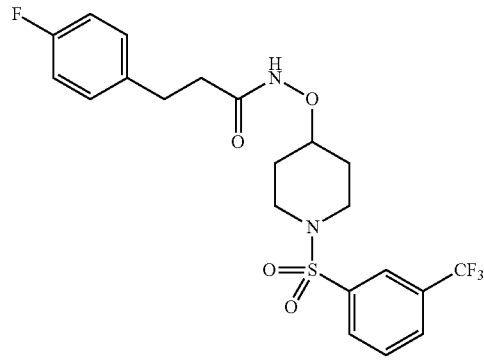 [SMILES: O=C(CCc1ccc(F)cc1)NOC1CCN(S(=O)(=O)c2cccc(C(F)(F)F)c2)CC1]

white solid: LCMS: 475 [M+1]⁺. ¹H NMR (DMSO-d₆) δ: 1.53 (m, 2H), 1.69 (m, 2H), 2.19 (t, 2H), 2.74 (m, 2H), 3.03 (m, 4H), 3.70 (s, 1H), 7.11 (m, 4H), 8.00 (m, 4H), 10.7 (s, 1H).

Example 6

4-Chloro-N-(1-(3-(trifluoromethyl)phenylsulfonyl)piperidin-4-yloxy)benzamide

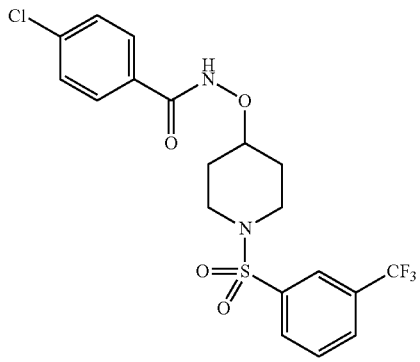 [SMILES: O=C(NOC1CCN(S(=O)(=O)c2cccc(C(F)(F)F)c2)CC1)c1ccc(Cl)cc1]

a) NaBH₄ (180 mg, 4.74 mmol) was added to a solution of 1-(3-(trifluoromethyl)phenylsulfonyl)piperidin-4-one (2.56 g, 8.34 mmol) in methanol (15 ml) at 0° C., and stirred at room temperature for 1 hour. The reaction was quenched with H₂O (50 ml) and extracted with ethyl acetate (20 ml×2). The combined organic phase was washed with H₂O (20 ml×2) and brine (20 ml×2), dried over Na₂SO₄ and concentrated in vacuo to give 1-(3-(trifluoromethyl)phenylsulfonyl)piperidin-4-ol (2.17 g, 84%) as a white solid: LCMS: 310 [M+1]⁺.

b) A solution of diethyl azodicarboxylate (1.10 g, 6.32 mmol) in tetrahydrofuran (5 ml) was added dropwise to a mixture of 1-(3-(trifluoromethyl)phenylsulfonyl)piperidin-4-ol (0.94 g, 3.04 mmol), 2-hydroxyisoindoline-1,3-dione (0.50 g, 3.07 mmol) and triphenylphosphine (1.65 g, 6.30 mmol) in tetrahydrofuran (10 ml) at 0° C. The reaction mixture was stirred at room temperature for 17 hours and concentrated in vacuo. The residue was purified by column chromatography (ethyl acetate/petroleum ether: 25/75) to give 2-(1-(3-(trifluoromethyl)phenylsulfonyl)piperidin-4-yloxy)isoindoline-1,3-dione (1.02 g, 74%) as a white solid: LCMS: 455 [M+1]⁺.

c) Hydrazine monohydrate (250 mg, 4.24 mmol) was added to a solution of 2-(1-(3-(trifluoromethyl)phenylsulfonyl)piperidin-4-yloxy)isoindoline-1,3-dione (1.02 g, 2.24 mmol) in ethanol (10 ml) and stirred at room temperature for 30 minutes. The resulting solid was filtered off and concentrated in vacuo. The residue was triturated with diethyl ether (30 ml), and the resulting solid was filtered off again and concentrated in vacuo to give O-(1-(3-(trifluoromethyl)phenylsulfonyl)piperidin-4-yl)hydroxylamine (720 mg, 94%) as a white solid: LCMS: 343 [M+1]⁺.

d) 1-(3-Dimethylaminopropyl)-3-ethylcarboiimide hydrochloride (138 mg, 0.72 mmol) was added to a solution of O-(1-(3-(trifluoromethyl)phenylsulfonyl)piperidin-4-yl)hydroxylamine (195 mg, 0.60 mmol), 1-hydroxybenzotriazole (97.0 mg, 0.72 mmol), 4-chlorobenzoic acid (94.0 mg, 0.60 mmol) and N,N-diisopropylethylamine (233 mg, 1.80 mmol) in N,N-dimethylformamide (6 ml). The reaction mixture was stirred at room temperature for 17 hours and quenched with H₂O (8 ml) and aqueous 1 N HCl solution (pH=3). The aqueous phase was extracted with CH₂Cl₂ (20 ml×3) and the combined organic phase was washed with aqueous NaHCO₃ solution and brine, dried over Na₂SO₄, filtered and concentrated in vacuo. The residue was purified by column chromatography (ethyl acetate/hexane: 67/33) to give 4-chloro-N-(1-(3-(trifluoromethyl)phenylsulfonyl)piperidin-4-yloxy)benzamide (172 mg, 62%) as a white solid: LCMS: 463 [M+1]⁺. ¹H NMR (DMSO-d₆) δ: 1.70 (m, 2H), 1.90 (m, 2H), 3.01 (m, 2H), 3.13 (m, 2H), 3.98 (d, 1H), 7.51 (d, 2H), 7.68 (m, 2H), 7.95 (m, 2H), 8.11 (m, 2H), 11.6 (s, 1H).

Example 7

3-Cyano-N-(1-(3-(trifluoromethyl)phenylsulfonyl)piperidin-4-yloxy)benzamide was prepared as described in EXAMPLE 6

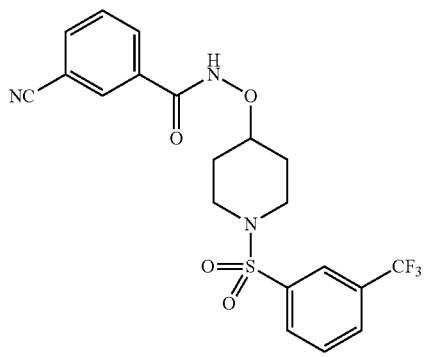 [SMILES: N#Cc1cccc(C(=O)NOC2CCN(S(=O)(=O)c3cccc(C(F)(F)F)c3)CC2)c1]

white solid: LCMS: 454 [M+1]⁺. ¹H NMR (DMSO-d₆) δ: 1.72 (m, 2H), 1.88 (m, 2H), 3.04 (m, 2H), 3.13 (m, 2H), 4.00 (s, 1H), 7.66 (d, 1H), 7.94 (m, 4H), 8.10 (m, 3H), 11.7 (s, 1H).

Example 8

2-(3,5-Bis(trifluoromethyl)phenyl)-N-(1-(3-(trifluoromethyl)phenylsulfonyl)piperidin-4-yloxy)acetamide was prepared as described in EXAMPLE 6

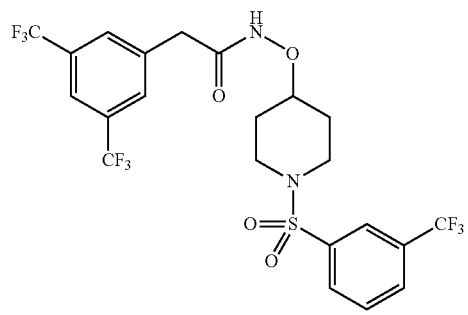 [SMILES: O=C(Cc1cc(C(F)(F)F)cc(C(F)(F)F)c1)NOC1CCN(S(=O)(=O)c2cccc(C(F)(F)F)c2)CC1]

white solid: LCMS: 579 [M+1]⁺. ¹H NMR (DMSO-d₆) δ: 1.64 (m, 2H), 1.80 (m, 2H), 3.04 (m, 4H), 3.53 (m, 2H), 3.84 (d, 1H), 7.93 (m, 5H), 8.11 (m, 2H), 11.1 (s, 1H).

Example 9

2,2-Diphenyl-N-(1-(3-(trifluoromethyl)phenylsulfonyl)piperidin-4-yloxy)acetamide was prepared as described in EXAMPLE 6

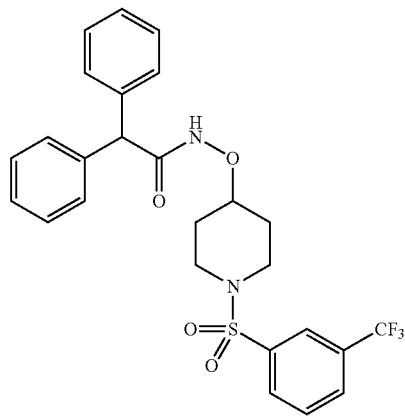 [SMILES: O=C(NOC1CCN(S(=O)(=O)c2cccc(C(F)(F)F)c2)CC1)C(c1ccccc1)c1ccccc1]

white solid: LCMS: 519 [M+1]⁺. ¹H NMR (DMSO-$d_6$) δ: 1.62 (m, 2H), 1.78 (m, 2H), 3.01 (m, 4H), 3.85 (s, 1H), 4.66 (s, 1H), 7.25 (m, 10H), 7.92 (m, 2H), 8.10 (m, 2H), 11.3 (s, 1H).

Example 10

(E)-3-(4-Fluorophenyl)-N-(1-(3-(trifluoromethyl)phenylsulfonyl)piperidin-4-yloxy)acrylamide was prepared as described in EXAMPLE 6

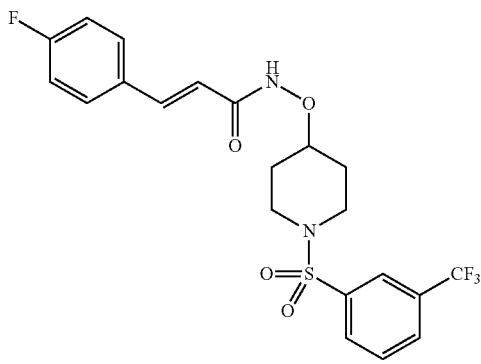 [SMILES: O=C(/C=C/c1ccc(F)cc1)NOC1CCN(S(=O)(=O)c2cccc(C(F)(F)F)c2)CC1]

white solid: LCMS: 473 [M+1]⁺. ¹H NMR (DMSO-$d_6$) δ: 1.70 (m, 2H), 1.89 (m, 2H), 3.05 (d, 2H), 3.15 (m, 2H), 3.94 (s, 1H), 6.35 (d, 2H), 7.45 (d, 2H), 7.63 (t, 2H), 7.95 (m, 2H), 8.15 (m, 2H), 11.1 (s, 1H).

Example 11

N-(1-(3-(Trifluoromethyl)phenylsulfonyl)piperidin-4-yloxy)cyclopropanecarboxamide was prepared as described in EXAMPLE 6

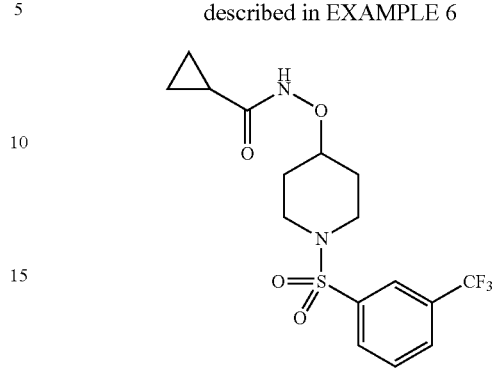

white solid: LCMS: 393 [M+1]⁺. ¹H NMR (DMSO-$d_6$) δ: 0.63 (d, 4H), 1.32 (d, 1H), 1.62 (m, 2H), 1.83 (m, 2H), 2.98 (t, 2H), 3.09 (t, 2H), 3.80 (m, 1H), 7.91 (m, 2H), 8.09 (m, 2H), 10.90 (s, 1H).

Example 12

3-Cyano-N-(1-(4-(trifluoromethoxy)phenylsulfonyl)piperidin-4-yloxy)benzamide

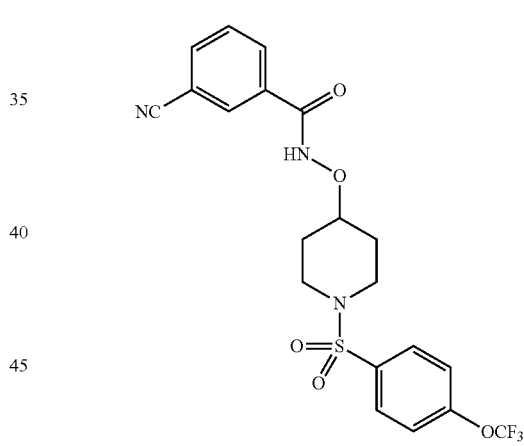

a) 4-Trifluoromethoxyphenylsulfonyl chloride (4.34 g, 16.7 mmol) was added to a solution of 4-piperidone monohydrate hydrochloride (2.99 g, 19.5 mmol) and N,N-diisopropylethylamine (9.50 ml, 57.5 mmol) in $CH_2Cl_2$ (50 ml) at 0° C. and stirred at room temperature for 20 hours. The reaction mixture was concentrated in vacuo and the residue was diluted with ethyl acetate (250 ml), washed with aqueous 1 N HCl solution (50 ml), $H_2O$ (50 ml), saturated aqueous $NaHCO_3$ solution (50 ml) and brine (50 ml), dried over $Na_2SO_4$ and concentrated in vacuo to give 1-(4-(trifluoromethoxy)phenylsulfonyl)piperidin-4-one (4.37 g, 81%) as a off-white solid.

b) $NaBH_4$ (719 mg, 19.0 mmol) was added in portions to a suspension of 1-(4-(trifluoromethoxy)phenylsulfonyl)piperidin-4-one (3.07 g, 9.50 mmol) in ethanol (50 ml) at 0° C. and stirred at room temperature for 2 hours. The reaction was quenched with acetone (50 ml) at 0° C. and concentrated in vacuo. The residue was diluted with ethyl acetate (100 ml), washed with saturated aqueous NaHCO₃ and brine, dried over Na₂SO₄, filtered and concentrated in vacuo to give 1-(4-(trifluoromethoxy)phenylsulfonyl)piperidin-4-ol (3.09 g, 100%) as a white solid: LCMS: 326 [M+1]⁺.

c) Diethyl azodicarboxylate (8.86 g, 33.8 mmol) was added to a solution of 1-(4-(trifluoromethoxy)phenylsulfonyl)piperidin-4-ol (10.0 g, 30.7 mmol), 2-hydroxyisoindoline-1,3-dione (5.01 g, 30.7 mmol) and triphenylphosphine (8.86 g, 33.8 mmol) in tetrahydrofuran (100 ml) at 0° C. The reaction mixture was stirred at room temperature for 17 hours and concentrated in vacuo. The residue was purified by column chromatography (ethyl acetate/petroleum ether: 33/67) to give 2-(1-(4-(trifluoromethoxy)phenylsulfonyl)piperidin-4-yloxy)isoindoline-1,3-dione (11.6 g, 80%) as a white solid: LCMS: 471 [M+1]⁺.

d) Hydrazine monohydrate (636 mg, 10.8 mmol) was added to a solution of 2-(1-(4-(trifluoromethoxy)phenylsulfonyl)piperidin-4-yloxy)isoindoline-1,3-dione (4.23 g, 9.00 mmol) in ethanol (40 ml) and stirred at 50° C. for 2 hours. The resulting solid was filtered off and concentrated in vacuo. The residue was triturated with diethyl ether (80 ml), and the resulting solid was filtered off again and concentrated in vacuo to give O-(1-(4-(trifluoromethoxy)phenylsulfonyl)piperidin-4-yl)hydroxylamine (2.63 g, 86%) as a white solid: LCMS: 341 [M+1]⁺.

e) 1-(3-Dimethylaminopropyl)-3-ethylcarboiimide hydrochloride (160 mg, 0.84 mmol) was added to a solution of O-(1-(4-(trifluoromethoxy)phenylsulfonyl)piperidin-4-yl)hydroxylamine (238 mg, 0.70 mmol), 1-hydroxybenzotriazole (114 mg, 0.84 mmol), 3-cyanobenzoic acid (103 mg, 0.70 mmol) and N,N-diisopropylethylamine (271 mg, 2.10 mmol) in N,N-dimethylformamide (6 ml). The reaction mixture was stirred at room temperature for 17 hours and quenched with H₂O (10 ml) and aqueous 1 N HCl solution (pH=3). The aqueous phase was extracted with CH₂Cl₂ (20 ml×3) and the combined organic phase was washed with aqueous NaHCO₃ solution and brine, dried over Na₂SO₄, filtered and concentrated in vacuo. The residue was purified by column chromatography (ethyl acetate/hexane: 33/67) to give 3-cyano-N-(1-(4-(trifluoromethoxy)phenylsulfonyl)piperidin-4-yloxy)benzamide (118 mg, 36%) as a white solid: LCMS: 470 [M+1]⁺. ¹H NMR (DMSO-d₆) δ: 1.77 (s, 2H), 1.92 (s, 2H), 3.02 (s, 2H), 3.12 (s, 2H), 4.03 (s, 1H), 7.67 (m, 3H), 8.01 (m, 5H), 11.7 (s, 1H).

Example 13

N¹-Cyclopropyl-N²-(1-(4-(trifluoromethoxy)phenylsulfonyl)piperidin-4-yloxy)oxalamide

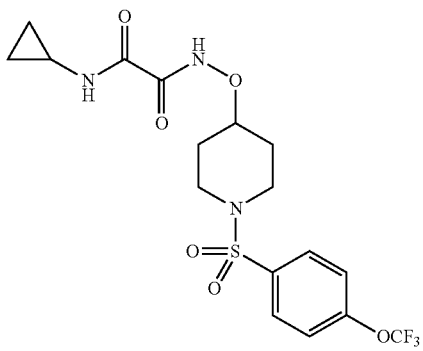 [SMILES: O=C(NOC1CCN(S(=O)(=O)c2ccc(OC(F)(F)F)cc2)CC1)C(=O)NC1CC1]

a) Ethyl chlorooxoacetate (0.145 ml, 1.30 mmol) was added to a solution of O-(1-(4-(trifluoromethoxy)phenylsulfonyl)piperidin-4-yl)hydroxylamine (390 mg, 1.15 mmol) and triethylamine (0.246 ml, 1.76 mmol) in CH₂Cl₂ (8 ml) and stirred at room temperature for 2 hours. The reaction mixture was diluted with CH₂Cl₂ and washed with aqueous NaHCO₃ solution (10 ml) and concentrated in vacuo to give crude product of N-[1-(4-trifluoromethoxybenzenesulfonyl)piperidin-4-yloxy]oxalamic acid ethyl ester.

b) Aqueous 1 N NaOH solution (5 ml) was added to a solution of N-[1-(4-trifluoromethoxybenzenesulfonyl)piperidin-4-yloxy]oxalamic acid ethyl ester in tetrahydrofuran-methanol (1:1, 10 ml) and stirred at room temperature for 1 hour. The reaction was quenched with aqueous 1 N HCl solution (6 ml). The resulting precipitation was collected and washed with H₂O to give N-[1-(4-trifluoromethoxybenzenesulfonyl)piperidin-4-yloxy]oxalamic acid (422 mg).

c) 1-(3-Dimethylaminopropyl)-3-ethylcarboiimide hydrochloride (70 mg, 0.37 mmol) was added to a solution of N-[1-(4-trifluoromethoxybenzenesulfonyl)piperidin-4-yloxy]oxalamic acid (102 mg, 0.247 mmol) 1-hydroxybenzotriazole (36 mg, 0.27 mmol) and cyclopropylamine (0.042 ml, 0.61 mmol) in N,N-dimethylformamide (5 ml). The reaction mixture was stirred at room temperature for 16 hours and quenched with aqueous 1 N HCl solution (5 ml) and H₂O (5 ml). The resulting precipitation was collected and washed with H₂O and diethyl ether to give N¹-cyclopropyl-N²-(1-(4-(trifluoromethoxy)phenylsulfonyl)piperidin-4-yloxy)oxalamide (48 mg, 43%) as a white solid: LCMS: 452 [M+1]⁺. ¹H NMR (DMSO-d₆) δ: 0.59 (m, 4H), 1.69 (m, 2H), 1.82 (m, 2H), 2.73 (m, 1H), 3.04 (m, 4H), 3.96 (m, 1H), 7.65 (d, 2H), 7.88 (d, 2H), 8.81 (d, 1H), 11.9 (s, 1H).

Example 14

N¹-(Cyclopropylmethyl)-N²-(1-(4-(trifluoromethoxy)phenylsulfonyl)piperidin-4-yloxy)oxalamide was prepared as described in EXAMPLE 13

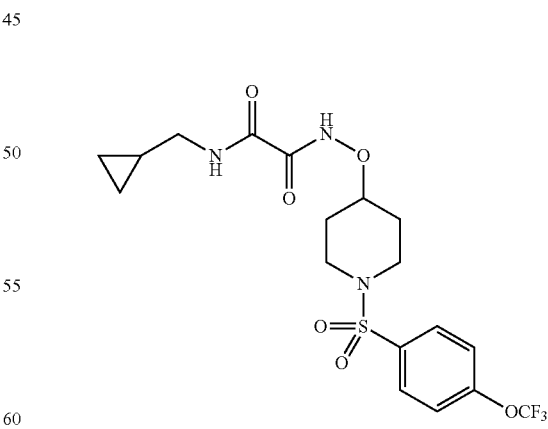

white solid: LCMS: 466 [M+1]⁺. ¹H NMR (DMSO-d₆) δ: −0.01 (m, 2H), 0.20 (m, 2H), 0.83 (m, 1H), 1.52 (m, 2H), 1.65 (m, 2H), 2.78 (t, 2H), 2.86 (4H, m), 3.79 (1H, m), 7.47 (d, 2H), 7.71 (d, 2H), 8.68 (t, 1H), 11.8 (s, 1H).

Example 15

N$^1$-(2,2,2-Trifluoroethyl)-N$^2$-(1-(4-(trifluoromethoxy)phenylsulfonyl)piperidin-4-yloxy)oxalamide was prepared as described in EXAMPLE 13

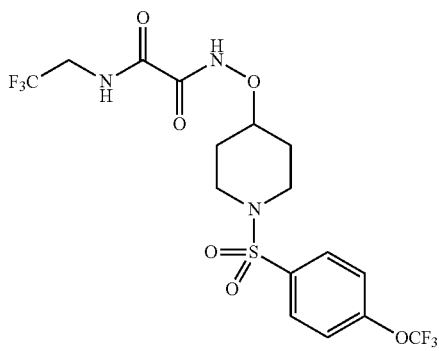 [SMILES: O=C(NCC(F)(F)F)C(=O)NOC1CCN(S(=O)(=O)c2ccc(OC(F)(F)F)cc2)CC1]

white solid: LCMS: 494 [M+1]$^+$. $^1$H NMR (DMSO-d$_6$) δ: 1.48 (m, 2H), 1.62 (m, 2H), 2.82 (4H, m), 3.66 (2H, m), 3.76 (1H, m), 7.43 (d, 2H), 7.67 (d, 2H), 9.19 (t, 1H), 11.9 (s, 1H).

Example 16

(S)-4-Fluoro-N-(1-(3-(trifluoromethyl)phenylsulfonyl)pyrrolidin-3-yloxy)benzamide

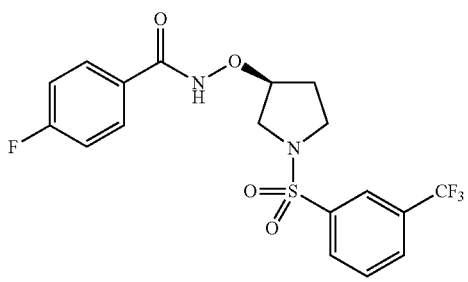 [SMILES: O=C(NO[C@H]1CCN(S(=O)(=O)c2cccc(C(F)(F)F)c2)C1)c1ccc(F)cc1]

a) Diethyl azodicarboxylate (17.4 g, 100 mmol) was added to a solution of (R)-tert-butyl 3-hydroxypyrrolidin-1-carboxylate (9.40 g, 50.0 mmol), 2-hydroxyisoindoline-1,3-dione (8.16 g, 50.0 mmol) and triphenylphosphine (26.2 g, 100 mmol) in tetrahydrofuran (100 ml) at 0° C. The reaction mixture was stirred at room temperature for 17 hours and concentrated in vacuo. The residue was purified by column chromatography (ethyl acetate/petroleum ether: 5/95 to 12.5/87.5) to give (S)-tert-butyl 3-(1,3-dioxoisoindoline-2-yloxy)pyrrolidin-1-carboxylate (6.74 g, 41%) as a white solid: LCMS: 277 [M−55]$^+$.

b) Trifluoroacetic acid (3.42 g, 30.0 mmol) was added to a solution of (S)-tert-butyl 3-(1,3-dioxoisoindolin-2-yloxy)pyrrolidin-1-carboxylate (3.32 g, 10.0 mmol) CH$_2$Cl$_2$ (25 ml) at 0° C. The reaction mixture was stirred at room temperature for 17 hours and concentrated in vacuo. The residue was triturated with diethyl ether (100 ml) to give (S)-2-(pyrrolidin-3-yloxy)isoindoline-1,3-dione)trifluoroacetic acid salt (2.77 g, 80%) as a white solid.

c) 3-Trifluoromethylphenylsulfonyl chloride (1.96 g, 8.00 mmol) was added to a solution of (S)-2-(pyrrolidin-3-yloxy)isoindoline-1,3-dione) trifluoroacetic acid salt (2.77 g, 8.00 mmol) and N,N-diisopropylethylamine (3.10 g, 24.0 mmol) in CH$_2$Cl$_2$ (50 ml) and stirred at room temperature for 4 hours. The reaction mixture was washed with aqueous 1 N HCl solution (50 ml×2), H$_2$O (50 ml×3) and brine (50 ml), dried over Na$_2$SO$_4$, filtered and concentrated in vacuo. The residue was purified by column chromatography (ethyl acetate/petroleum ether: 12.5/87.5 to 50/50) to give (S)-2-(1-(3-trifluoromethyl)phenylsulfonyl)pyrrolidin-3-yloxy)isoindoline-1,3-dione (1.87 g, 53%) as a white solid.

d) Hydrazine solution (0.37 g, 9.30 mmol) was added to a solution of (S)-2-(1-(3-trifluoromethyl)phenylsulfonyl)pyrrolidin-3-yloxy)isoindoline-1,3-dione (3.74 g, 8.40 mmol) in ethanol (16 ml) and stirred at room temperature for 1 hours. The resulting solid was filtered off and concentrated in vacuo. The residue was triturated with diethyl ether (30 ml), and the resulting solid was filtered off again and concentrated in vacuo to give (S)—O-(1-(3-(trifluoromethyl)phenylsulfonyl) pyrrolidin-3-yl)hydroxylamine (2.37 g, 90.0%) as a greenish solid.

e) 1-(3-Dimethylaminopropyl)-3-ethylcarboiimide hydrochloride (68.0 mg, 0.35 mmol) was added to a solution of (S)—O-(1-(3-(trifluoromethyl)phenylsulfonyl)pyrrolidin-3-yl)hydroxylamine (100 mg, 0.32 mmol), 1-hydroxybenzotriazole (45.0 mg, 0.35 mmol), 4-fluorobenzoic acid (45 mg, 0.32 mmol) and N,N-diisopropylethylamine (125 mg, 0.97 mmol) in N,N-dimethylformamide (10 ml). The reaction mixture was stirred at room temperature for 17 hours and quenched with H$_2$O (30 ml). The aqueous phase was extracted with ethyl acetate (30 ml×3) and the combined organic phase was washed with aqueous 0.1 N HCl solution (20 ml), H$_2$O (30 ml×3) and brine (30 ml), dried over Na$_2$SO$_4$, filtered and concentrated in vacuo. The residue was purified by column chromatography (ethyl acetate/hexane: 33/67) to give (S)-2-(4-fluorophenyl)-N-(1-(3-(trifluoromethyl)phenylsulfonyl)pyrrolidin-3-yloxy)acetamide (90.0 mg, 65%) as a white solid: LCMS: 433 [M+1]$^+$. $^1$H NMR (DMSO-d$_6$) δ: 1.88 (m, 1H), 2.04 (m, 1H), 3.37 (m, 3H), 3.54 (d, 1H), 4.55 (s, 1H), 7.29 (t, 2H), 7.76 (m, 2H), 7.87 (t, 1H), 8.06 (t, 2H), 8.15 (d, 1H), 11.6 (s, 1H).

Example 17

(S)-2-(4-Fluorophenyl)-N-(1-(3-(trifluoromethyl) phenylsulfonyl)pyrrolidin-3-yloxy)acetamide was prepared as described in EXAMPLE 16

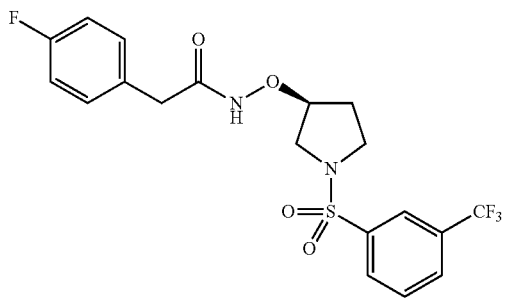 [SMILES: O=C(Cc1ccc(F)cc1)NO[C@H]1CCN(S(=O)(=O)c2cccc(C(F)(F)F)c2)C1]

white solid: LCMS: 447 [M+1]$^+$. $^1$H NMR (DMSO-d$_6$) δ: 1.81 (m, 1H), 1.93 (m, 1H), 3.24 (m, 4H), 3.41 (m, 1H), 3.45 (d, 1H), 3.39 (s, 1H), 7.10 (t, 2H), 7.22 (t, 2H), 7.86 (t, 1H), 8.02 (s, 1H), 8.10 (m, 2H), 11.2 (s, 1H).

Example 18

(S)—N-(1-(3-(Trifluoromethyl)phenylsulfonyl)pyrrolidin-3-yloxy)cyclopropanecarboxamide was prepared as described in EXAMPLE 16

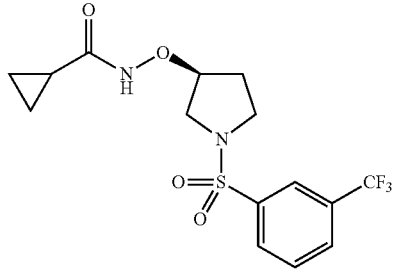 [SMILES: O=C(NO[C@H]1CCN(S(=O)(=O)c2cccc(C(F)(F)F)c2)C1)C1CC1]

white solid: LCMS: 379 [M+1]+. $^1$H NMR (DMSO-d$_6$) δ: 0.66 (m, 4H), 1.33 (m, 1H), 1.84 (m, 1H), 1.95 (m, 1H), 3.29 (m, 3H), 3.44 (d, 1H), 3.40 (t, 1H), 7.89 (t, 1H), 8.05 (s, 1H), 8.13 (m, 2H), 10.5 (s, 1H).

Example 19

(R)-4-Fluoro-N-(1-(3-(trifluoromethyl)phenylsulfonyl)pyrrolidin-3-yloxy)benzamide was prepared as described in EXAMPLE 16

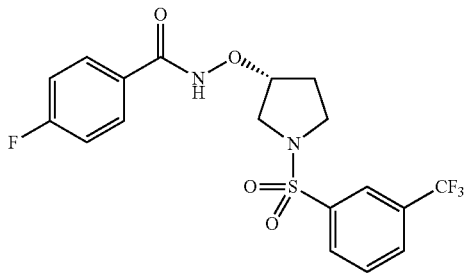 [SMILES: O=C(NO[C@@H]1CCN(S(=O)(=O)c2cccc(C(F)(F)F)c2)C1)c1ccc(F)cc1]

white solid: LCMS: 433 [M+1]+. $^1$H NMR (DMSO-d$_6$) δ: 1.88 (m, 1H), 2.04 (m, 1H), 3.37 (m, 3H), 3.54 (d, 1H), 4.55 (s, 1H), 7.28 (t, 2H), 7.76 (m, 2H), 7.86 (t, 1H), 8.06 (t, 2H), 8.15 (d, 1H), 11.6 (s, 1H).

Example 20

(R)-2-(4-Fluorophenyl)-N-(1-(3-(trifluoromethyl)phenylsulfonyl)pyrrolidin-3-yloxy)acetamide was prepared as described in EXAMPLE 16

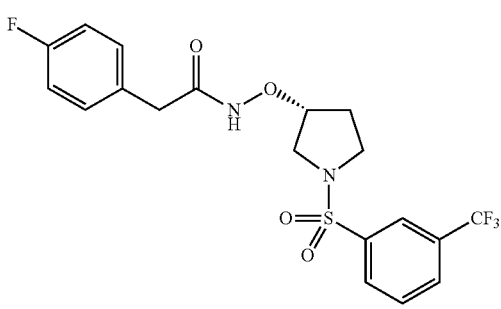 [SMILES: O=C(Cc1ccc(F)cc1)NO[C@@H]1CCN(S(=O)(=O)c2cccc(C(F)(F)F)c2)C1]

white solid: LCMS: 447 [M+1]+. $^1$H NMR (DMSO-d$_6$) δ: 1.81 (m, 1H), 1.93 (m, 1H), 3.24 (m, 4H), 3.41 (m, 1H), 3.45 (d, 1H), 4.39 (s, 1H), 7.10 (t, 2H), 7.22 (t, 2H), 7.85 (t, 1H), 8.08 (m, 3H), 11.1 (s, 1H).

Example 21

(R)—N-(1-(3-(Trifluoromethyl)phenylsulfonyl)pyrrolidin-3-yloxy)cyclopropanecarboxamide was prepared as described in EXAMPLE 16

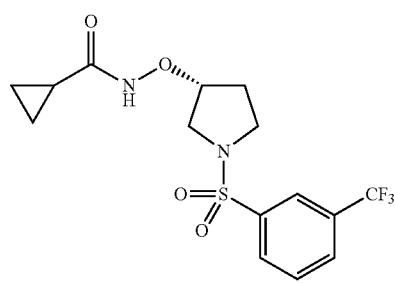 [SMILES: O=C(NO[C@@H]1CCN(S(=O)(=O)c2cccc(C(F)(F)F)c2)C1)C1CC1]

yellow solid: LCMS: 379 [M+1]+. $^1$H NMR (DMSO-d$_6$) δ: 0.60 (m, 4H), 1.31 (m, 1H), 1.85 (m, 1H), 1.93 (m, 1H), 3.3 (m, 3H), 3.41 (d, 1H), 4.37 (s, 1H), 7.59 (t, 1H), 8.01 (d, 1H), 8.13 (t, 2H), 11.02 (s, 1H).

Example 22

1-Ethyl-3-(1-(3-(trifluoromethyl)phenylsulfonyl)piperidin-4-yloxy)urea

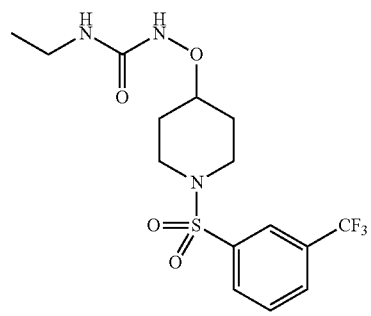 [SMILES: CCNC(=O)NOC1CCN(S(=O)(=O)c2cccc(C(F)(F)F)c2)CC1]

Isocyanatoethane (53.0 mg, 0.74 mmol) was added to a solution of O-(1-(3-(trifluoromethyl)phenylsulfonyl)piperidin-4-yl)hydroxylamine (200 mg, 0.62 mmol) and pyridine (98 mg, 1.23 mmol) in CH$_2$Cl$_2$ (4 ml) and stirred at room temperature for 17 hours. The resulting precipitation was collected, washed with aqueous 1 N HCl solution (10 ml×3), aqueous NaHCO$_3$ solution (10 ml×3), ether (10 ml×2) to give 1-ethyl-3-(1-(3-(trifluoromethyl)phenylsulfonyl)piperidin-4-yloxy)urea (156 mg, 64%) as a white solid: LCMS: 396 [M+1]+. $^1$H NMR (DMSO-d$_6$) δ: 0.98 (m, 3H), 1.73 (m, 2H), 1.86 (m, 2H), 2.85 (m, 2H), 3.00 (m, 2H), 3.18 (n, 2H), 3.60 (m, 1H), 6.65 (m, 1H), 7.91 (m, 2H), 8.01 (m, 2H), 8.82 (s, 1H).

Example 23

1-(4-Fluorophenyl)-3-(1-(3-(trifluoromethyl)phenyl-sulfonyl)piperidin-4-yloxy)urea was prepared as described in EXAMPLE 22

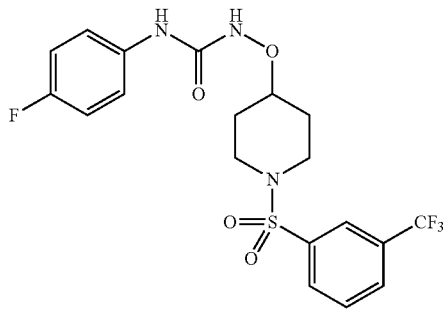 [SMILES: O=C(NOC1CCN(S(=O)(=O)c2cccc(C(F)(F)F)c2)CC1)Nc1ccc(F)cc1]

white solid: LCMS: 462 [M+1]$^+$. $^1$H NMR (DMSO-d$_6$) δ: 1.78 (t, 2H), 1.91 (m, 2H), 2.87 (m, 2H), 3.22 (m, 2H), 3.76 (t, 1H), 7.07 (m, 2H), 7.48 (m, 2H), 7.90 (m, 2H), 8.08 (m, 2H), 8.63 (s, 1H), 9.35 (s, 1H).

Example 24

1-(3,5-Bis(trifluoromethyl)phenyl)-3-(1-(3-(trifluoromethyl)phenylsulfonyl)piperidin-4-yloxy)urea was prepared as described in EXAMPLE 22

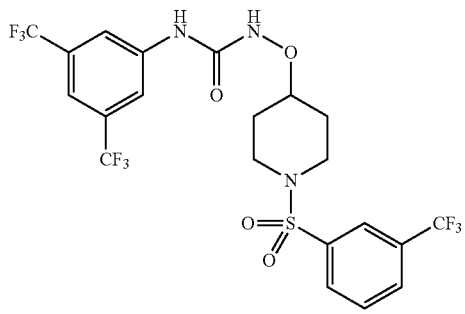 [SMILES: O=C(NOC1CCN(S(=O)(=O)c2cccc(C(F)(F)F)c2)CC1)Nc1cc(C(F)(F)F)cc(C(F)(F)F)c1]

white solid: LCMS: 580 [M+1]$^+$. $^1$H NMR (DMSO-d$_6$) δ: 1.78 (m, 2H), 1.97 (m, 2H), 2.85 (m, 2H), 3.25 (m, 2H), 3.80 (t, 1H), 7.64 (s, 1H), 7.91 (m, 2H), 8.09 (m, 2H), 8.28 (s, 2H), 9.20 (s, 1H), 9.82 (s, 1H).

Example 25

1-Phenyl-3-(1-(3-(trifluoromethyl)phenylsulfonyl)piperidin-4-yloxy)urea was prepared as described in EXAMPLE 22

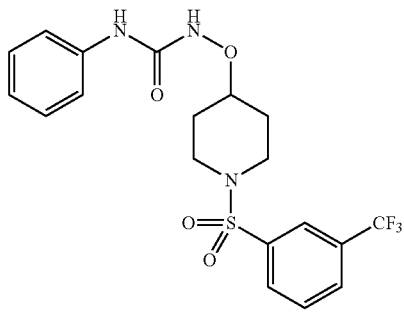 [SMILES: O=C(NOC1CCN(S(=O)(=O)c2cccc(C(F)(F)F)c2)CC1)Nc1ccccc1]

white solid: LCMS: 444 [M+1]$^+$. $^1$H NMR (DMSO-d$_6$) δ: 1.77 (t, 2H), 1.91 (t, 2H), 2.88 (m, 2H), 3.23 (m, 2H), 3.76 (t, 1H), 6.99 (m, 1H), 7.23 (m, 2H), 7.48 (t, 2H), 7.90 (m, 2H), 8.08 (m, 2H), 8.50 (s, 1H), 9.32 (s, 1H).

Example 26

1-Cyclohexyl-3-(1-(3-(trifluoromethyl)phenylsulfonyl)piperidin-4-yloxy)urea was prepared as described in EXAMPLE 22

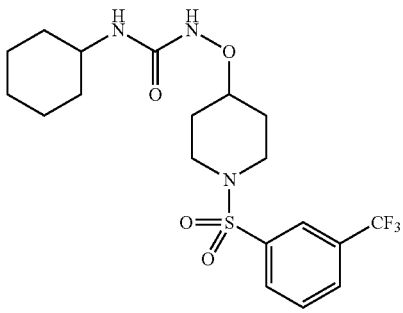 [SMILES: O=C(NOC1CCN(S(=O)(=O)c2cccc(C(F)(F)F)c2)CC1)NC1CCCCC1]

white solid: LCMS: 450 [M+1]$^+$. $^1$H NMR (DMSO-d$_6$) δ: 1.11 (t, 1H), 1.21 (m, 4H), 1.61 (t, 1H), 1.71 (m, 4H), 1.83 (m, 2H), 1.89 (m, 2H), 2.86 (m, 2H), 3.18 (m, 2H), 3.36 (m, 1H), 3.61 (m, 1H), 6.17 (d, 1H), 7.91 (m, 2H), 8.09 (m, 2H), 8.80 (s, 1H).

Example 27

1-(4-Fluorobenzyl)-3-(1-(3-(trifluoromethyl)phenyl-sulfonyl)piperidin-4-yloxy)urea was prepared as described in EXAMPLE 22

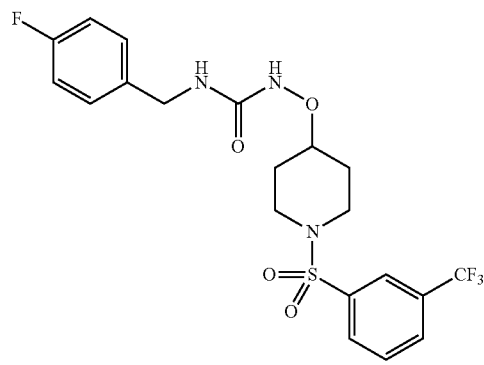 [SMILES: O=C(NCc1ccc(F)cc1)NOC1CCN(S(=O)(=O)c2cccc(C(F)(F)F)c2)CC1]

white solid: LCMS: 476 [M+1]$^+$. $^1$H NMR (DMSO-d$_6$) δ: 1.72 (m, 2H), 1.90 (m, 2H), 2.84 (m, 2H), 3.19 (m, 2H), 3.65 (t, 1H), 4.17 (d, 2H), 7.09 (m, 2H), 7.23 (m, 2H), 7.32 (m, 1H), 7.89 (m, 2H), 8.10 (m, 2H), 8.99 (s, 1H).

Example 28

1-Propyl-3-(1-(3-(trifluoromethyl)phenylsulfonyl)piperidin-4-yloxy)urea

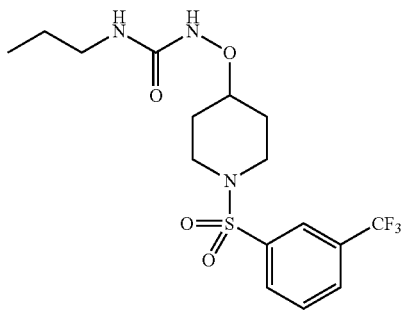 [SMILES: CCCNC(=O)NOC1CCN(S(=O)(=O)c2cccc(C(F)(F)F)c2)CC1]

1,1'-Carbonyldiimidazole (194 mg, 1.20 mmol) was added to a solution of O-(1-(3-(trifluoromethyl)phenylsulfonyl)piperidin-4-yl)hydroxylamine (195 mg, 0.60 mmol) and triethylamine (121 mg, 1.20 mmol) in CH$_2$Cl$_2$ (5 ml) and stirred at room temperature for 17 hours. Propan-1-amine (35.0 mg, 0.60 mmol) was added to the reaction mixture and stirred at room temperature for another 17 hours. The resulting precipitaion was collected, washed with aqueous 1 N HCl solution (10 ml×3), aqueous NaHCO$_3$ solution (10 ml×3), diethyl ether (10 ml×2) to give 1-propyl-3-(1-(3-(trifluoromethyl)phenylsulfonyl)piperidin-4-yloxy)urea (215 mg, 88%) as a white solid: LCMS: 410 [M+1]$^+$. $^1$H NMR (DMSO-d$_6$) δ: 0.77 (t, 3H), 1.37 (m, 2H), 1.73 (m, 2H), 1.88 (m, 2H), 2.87 (m, 4H), 3.17 (m, 2H), 3.61 (t, 1H), 6.63 (t, 1H), 7.90 (m, 2H), 8.08 (m, 2H), 8.79 (s, 1H).

Example 29

1-Butyl-3-(1-(3-(trifluoromethyl)phenylsulfonyl)piperidin-4-yloxy)urea was prepared as described in EXAMPLE 28

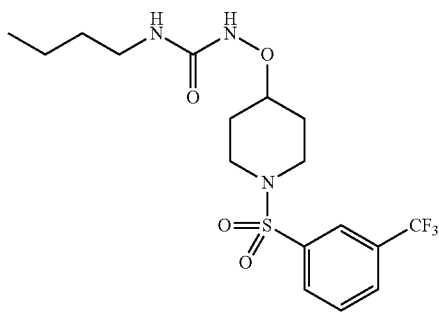 [SMILES: CCCCNC(=O)NOC1CCN(S(=O)(=O)c2cccc(C(F)(F)F)c2)CC1]

white solid: LCMS: 424 [M+1]$^+$. $^1$H NMR (DMSO-d$_6$) δ: 0.83 (t, 3H), 1.21 (m, 2H), 1.35 (m, 2H), 1.70 (m, 2H), 1.85 (m, 2H), 2.85 (m, 2H), 2.97 (m, 2H), 3.18 (t, 2H), 3.61 (t, 1H), 6.61 (t, 1H), 7.91 (m, 2H), 8.10 (m, 2H), 8.79 (s, 1H).

Example 30

1-Cyclopropyl-3-(1-(3-(trifluoromethyl)phenylsulfonyl)piperidin-4-yloxy)urea was prepared as described in EXAMPLE 28

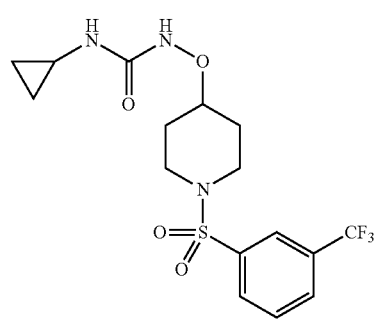 [SMILES: O=C(NOC1CCN(S(=O)(=O)c2cccc(C(F)(F)F)c2)CC1)NC1CC1]

white solid: LCMS: 408 [M+1]$^+$. $^1$H NMR (DMSO-d$_6$) δ: 0.39 (t, 2H), 0.51 (t, 2H), 1.67 (d, 2H), 1.82 (t, 2H), 2.44 (m, 1H), 2.84 (t, 2H), 3.15 (s, 2H), 3.60 (t, 1H), 6.61 (d, 1H), 7.92 (t, 2H), 8.08 (m, 2H), 8.85 (s, 1H).

Example 31

1-(2-(4-Fluorophenoxy)ethyl)-3-(1-(3-(trifluoromethyl)phenylsulfonyl)piperidin-4-yloxy)urea

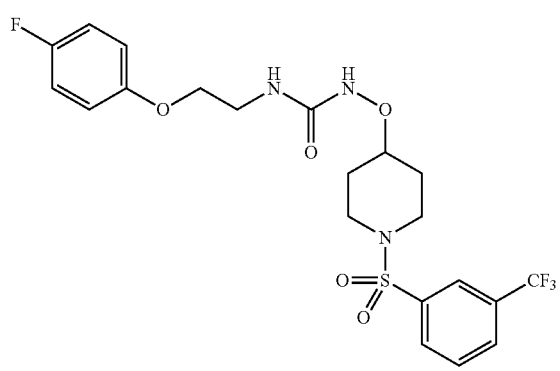 [SMILES: O=C(NCCOc1ccc(F)cc1)NOC1CCN(S(=O)(=O)c2cccc(C(F)(F)F)c2)CC1]

a) tert-Butyl-2-bromoacetate (1.95 g, 10.0 mmol) was added to a mixture of 4-fluorophenol (1.12 g, 10.0 mmol) and NaOH (400 mg, 10.0 mmol) in N,N-dimethylformamide (15 ml) and stirred at room temperature for 17 hours. The reaction was quenched with H$_2$O (50 ml) and extracted by ethyl acetate (50 ml×3). The combined organic phase was washed with H$_2$O (50 ml×4) and brine (50 ml), dried over Na$_2$SO$_4$, filtered and concentrated in vacuo to give tert-butyl 2-(4-fluorophenoxy)acetate (2.16 g, 95%) as yellow oil: LC-MS: 171 [M−55]$^+$.

b) LiAlH$_4$ (378 mg, 10.0 mmol) was added at −15° C. to a solution of tert-butyl 2-(4-fluorophenoxy)acetate (2.03 g, 9.00 mmol) in tetrahydrofuran (10 ml) and stirred at room temperature for 20 minutes. Aqueous 15% NaOH solution (2 ml), Na$_2$SO$_4$ (2.84 g) and H$_2$O (6 ml) were added to the reaction mixture and stirred for 1 hour. The resulting precipitation was filtered off and washed with tetrahydrofuran (30 ml×3). The filtrate was dried over $Na_2SO_4$, filtered and concentrated in vacuo to give 2-(4-fluorophenoxy)ethanol (1.12 g, 80%) as yellow oil: LC-MS: 157 [M+1]$^+$.

c) Diethyl azodicarboxylate (1.25 g, 7.20 mmol) was added to a solution of 2-(4-fluorophenoxy)ethanol (1.12 g, 7.20 mmol), isoindoline-1,3-dione (1.06 g, 7.20 mmol) and triphenylphosphine (1.89 g, 7.20 mmol) in tetrahydrofuran (20 ml) at 0° C. The reaction mixture was stirred at room temperature for 17 hours and concentrated in vacuo. The residue was purified by column chromatography (ethyl acetate/petroleum ether: 10/90 to 12.5/87.5) to give 2-(2-(4-fluorophenoxy)ethyl)isoindoline-1,3-dione (1.05 g, 51%) as a white solid: LCMS: 286 [M+1]$^+$.

d) Hydrazine solution (138 mg, 2.75 mmol) was added to a solution of 2-(2-(4-fluorophenoxy)ethyl)isoindoline-1,3-dione (713 mg, 2.5 mmol) in methanol (8 ml) and stirred at room temperature for 4 hours. The resulting solid was filtered off and concentrated in vacuo. The residue was triturated with diethyl ether (30 ml), and the resulting solid was filtered off again and concentrated in vacuo to give 2-(4-fluorophenoxy)ethanamine (280 mg, 70%) as colorless oil: LCMS: 325 [M+1]$^+$.

e) 1,1′-Carbonyldiimidazole (162 mg, 1.00 mmol) was added to a solution of O-1-(3-(trifluoromethyl)phenylsulfonyl)piperidin-4-yl)hydroxylamine (78.0 mg, 0.50 mmol) and triethylamine (101 mg, 1.00 mmol) in $CH_2Cl_2$ (15 ml) and stirred at room temperature for 24 hours. 2-(4-fluorophenoxy)ethanamine (162 mg, 0.50 mmol) was added to the reaction mixture and stirred at room temperature for another 17 hours. The reaction mixture was diluted with $CH_2Cl_2$ (50 ml) and washed with aqueous 0.1 N HCl solution (20 ml), $H_2O$ (30 ml×3) and brine (30 ml), dried over $Na_2SO_4$, filtered and concentrated in vacuo. The residue was purified by preparative TLC (ethyl acetate/petroleum ether: 67/33) to give 1-(2-(4-fluorophenoy)ethyl-3-(1-(3-(trifluoromethyl)phenylsulfonyl)piperidin-4-yloxy)urea (80 mg, 32%) as a white solid: LCMS: 506 [M+1]$^+$. $^1$H NMR (DMSO-$d_6$) δ: 1.68 (t, 2H), 1.87 (t, 2H), 2.83 (t, 2H), 3.20 (d, 2H), 3.37 (m, 2H), 3.62 (d, 1H), 3.94 (2H, t), 6.84 (t, 1H), 6.93 (m, 2H), 7.09 (t, 2H), 7.91 (t, 1H), 7.97 (s, 1H), 8.07 (d, 1H), 8.13 (d, 1H), 9.01 (s, 1H).

Example 32

1-(4-Fluorophenyl)-1-methyl-3-(1-(3-(trifluoromethyl)phenylsulfonyl)piperidin-4-yloxy)urea was prepared as described in EXAMPLE 28

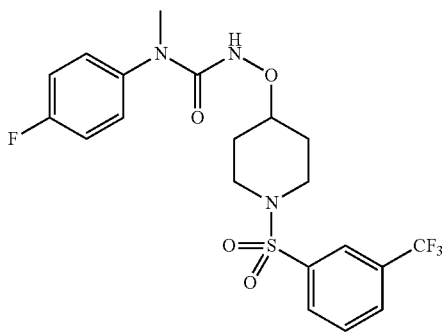 [SMILES: CN(C(=O)NOC1CCN(S(=O)(=O)c2cccc(C(F)(F)F)c2)CC1)c1ccc(F)cc1]

white solid: LCMS: 476 [M+1]$^+$. $^1$H NMR (DMSO-$d_6$) δ: 1.63 (m, 2H), 1.75 (m, 2H), 2.99 (m, 7H), 3.70 (m, 1H), 7.14 (m, 2H), 7.22 (m, 2H), 7.92 (t, 1H), 8.04 (s, 1H), 8.09 (d, 1H), 8.10 (d, 1H), 9.20 (s, 1H).

Example 33

1-(Cyclopropylmethyl)-3-(1-(3-(trifluoromethyl)phenylsulfonyl)piperidin-4-yloxy)urea was prepared as described in EXAMPLE 28

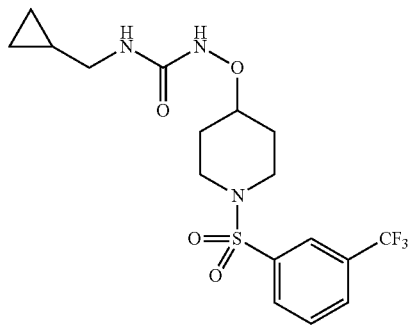 [SMILES: O=C(NCC1CC1)NOC1CCN(S(=O)(=O)c2cccc(C(F)(F)F)c2)CC1]

white solid: LCMS: 422 [M+1]$^+$. $^1$H NMR (DMSO-$d_6$) δ: 0.11 (m, 2H), 0.32 (m, 2H), 0.87 (m, 2H), 1.71 (m, 2H), 1.85 (m, 2H), 2.85 (m, 4H), 3.18 (m, 2H), 3.62 (m, 2H), 6.68 (t, 1H), 7.90 (t, 1H), 7.95 (s, 1H), 8.06 (d, 1H), 8.11 (d, 1H), 8.83 (s, 1H).

Example 34

3-(4-Fluorophenyl)-1-methyl-1-(1-(3-(trifluoromethyl)phenylsulfonyl)piperidin-4-yloxy)urea

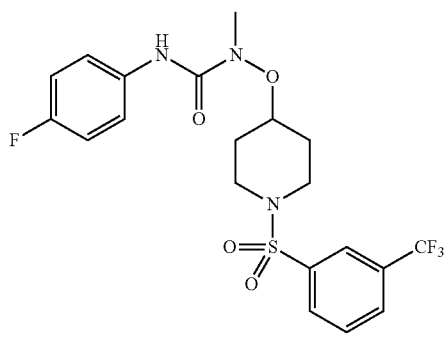 [SMILES: CN(OC1CCN(S(=O)(=O)c2cccc(C(F)(F)F)c2)CC1)C(=O)Nc1ccc(F)cc1]

a) Formaldehyde (166 mg, 5.55 mmol) was added to a solution of O-(1-(3-(trifluoromethyl)phenylsulfonyl)piperidin-4-yl) hydroxylamine (200 mg, 0.617 mmol) in 1,2-dichlorethane (5 ml) and stirred at room temperature for 3 hours. Sodium triacetoxyborohydride was added and stirred at room temperature for 12 hours. The reaction mixture was diluted with of ethyl acetate (30 ml), washed with $H_2O$ and brine, dried over $Na_2SO_4$, filtered and concentrated in vacuo. The residue was purified by column chromatography (the residue was purified by preparative TLC (ethyl acetate/petroleum ether: 67/33) to give N-methyl-O-(1-(3-(trifluoromethyl)phenylsulfonyl)piperidin-4-yl)hydroxylamine (125 mg, 60%) as a white solid.

b) A solution of N-methyl-O-(1-(3-(trifluoromethyl)phenylsulfonyl)piperidin-4-yl)hydroxylamine (130 mg, 0.384 mmol) in tetrahydrofuran (10 ml) was added to a suspension of trichloromethyl chloroformate (91.3 mg, 0.46 mmol) and activated charcoal (20 mg) in tetrahydrofuran (35 ml) at 0° C. over 30 minutes. After stirring at room temperature for 18 hours, the reaction mixture was filtered over silicagel and the filtrate was concentrated in vacuo. The residue was dissolved in tetrahydrofuran (15 ml), 4-fluoroaniline (65 mg, 1.13 mmol) and N,N-diisopropylethylamine (148 mg, 1.15 mmol) were added and the whole was stirred at room temperature for 18 hours. The reaction mixture was concentrated in vacuo and the residue was diluted with ethyl acetate (50 ml), washed with $H_2O$ (20 ml×2), brine (20 ml×2), dried over $Na_2SO_4$ and concentrated in vacuo. The residual solid was recrystallized from diethyl ether to give 3-(4-fluorophenyl)-1-methyl-1-(1-(3-(trifluoromethyl)phenylsulfonyl)piperidin-4-yloxy)urea (89.5 mg, 49%) as a white solid. LCMS: 476 [M+1]$^+$. $^1$H NMR (DMSO-$d_6$) δ: 1.79 (m, 2H), 1.98 (m, 2H), 2.59 (m, 2H), 3.0 (s, 3H), 3.62 (d, 2H), 3.89 (m, 1H), 7.11 (t, 2H), 7.50 (m, 2H), 7.94 (q, 2H), 8.12 (q, 2H), 8.70 (s, 1H).

Example 35

1-(2,2,2-Trifluoroethyl)-3-(1-(3-(trifluoromethyl)phenylsulfonyl)piperidin-4-yloxy)urea was prepared as described in EXAMPLE 28

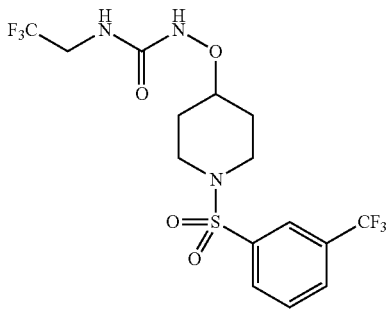 [SMILES: O=C(NCC(F)(F)F)NOC1CCN(S(=O)(=O)c2cccc(C(F)(F)F)c2)CC1]

white solid: LCMS: 450 [M+1]$^+$. $^1$H NMR (DMSO-$d_6$) δ: 1.73 (m, 2H), 1.89 (m, 2H), 2.87 (m, 2H), 3.22 (m, 2H), 3.66 (m, 1H), 3.77 (m, 2H), 7.29 (t, 1H), 7.89-8.14 (m, 4H), 9.33 (s, 1H).

Example 36

1-(1-(3-(Trifluoromethyl)phenylsulfonyl)piperidin-4-yloxy)-3-(3,3,3-trifluoropropyl)urea was prepared as described in EXAMPLE 67

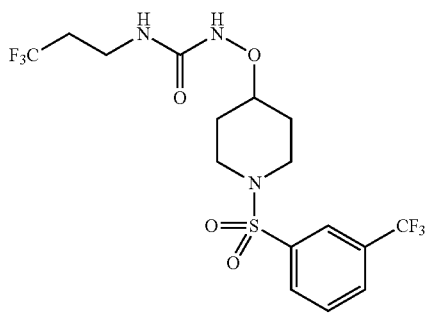 [SMILES: O=C(NCCC(F)(F)F)NOC1CCN(S(=O)(=O)c2cccc(C(F)(F)F)c2)CC1]

white solid: LCMS: 464 [M+1]$^+$. $^1$H NMR (DMSO-$d_6$) δ: 1.72 (m, 2H), 1.88 (m, 2H), 2.40 (m, 2H), 2.87 (m, 2H), 3.21-3.28 (m, 4H), 3.63 (m, 1H), 3.77 (m, 2H), 6.87 (t, 1H), 7.90-8.14 (m, 4H), 9.05 (s, 1H).

Example 37

1-(Cyclopropylmethyl)-3-(1-(4-(trifluoromethoxy)phenylsulfonyl)piperidin-4-yloxy)urea

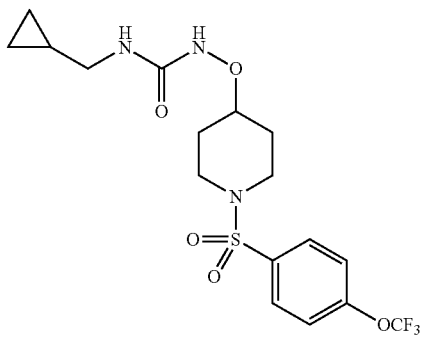 [SMILES: O=C(NCC1CC1)NOC1CCN(S(=O)(=O)c2ccc(OC(F)(F)F)cc2)CC1]

1,1'-Carbonyldiimidazole (227 mg, 1.4 mmol) was added to a solution of O-(1-(4-(trifluoromethoxy)phenylsulfonyl)piperidin-4-yl) hydroxylamine (238 mg, 0.70 mmol) and triethylamine (141 mg, 1.4 mmol) in $CH_2Cl_2$ (6 ml) and stirred at room temperature for 17 hours. Cyclopropylmethanamine (75 mg, 1.05 mmol) was added to the reaction mixture and stirred at room temperature for another 7 hours. The reaction mixture was quenched with $H_2O$ (10 ml) and aqueous 1 N HCl solution (pH=3) and extracted with $CH_2Cl_2$ (70 ml×3). The combined organic phase was washed with aqueous $NaHCO_3$ solution and brine, dried over $Na_2SO_4$, filtered and concentrated in vacuo. The residue was purified by column chromatography (ethyl acetate/n-hexane: 33/67) to give 1-(cyclopropylmethyl)-3-(1-(4-(trifluoromethoxy)phenylsulfonyl)piperidin-4-yloxy)urea (120 mg, 39%) as a white solid. LCMS: 438 [M+1]$^+$. $^1$H NMR (DMSO-$d_6$) δ: 0.14 (m, 2H), 0.35 (m, 2H), 0.90 (m, 1H), 1.74 (m, 2H), 1.86 (m, 2H), 2.85 (m, 4H), 3.20 (m, 2H), 3.65 (m, 1H), 6.71 (m, 1H), 7.65 (m, 2H), 7.90 (m, 2H), 8.86 (s, 1H).

Example 38

1-(Pyridin-4-yl)-3-(1-(4-(trifluoromethoxy)phenylsulfonyl)piperidin-4-yloxy)urea was prepared as described in EXAMPLE 37

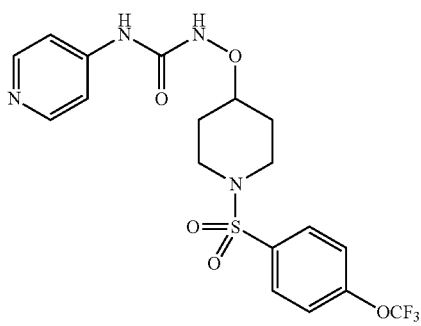 [SMILES: O=C(NOC1CCN(S(=O)(=O)c2ccc(OC(F)(F)F)cc2)CC1)Nc1ccncc1]

white solid: LCMS: 461 [M+1]⁺. ¹H NMR (DMSO-d₆) δ: 1.75 (m, 2H), 1.90 (m, 2H), 2.84 (m, 2H), 3.24 (m, 2H), 3.78 (m, 1H), 7.53 (m, 4H), 7.89 (m, 2H), 8.33 (m, 2H), 8.95 (s, 1H), 9.69 (s, 1H).

Example 39

1-(4-Chlorophenyl)-3-(1-(4-(trifluoromethoxy)phenylsulfonyl)piperidin-4-yloxy)urea was prepared as described in EXAMPLE 37

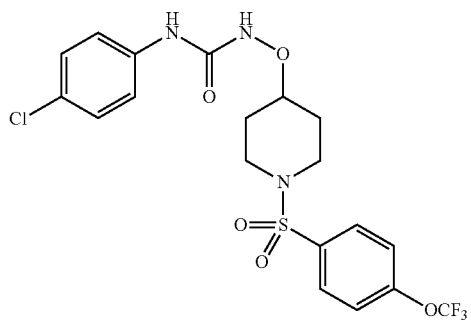 [SMILES: O=C(NOC1CCN(S(=O)(=O)c2ccc(OC(F)(F)F)cc2)CC1)Nc1ccc(Cl)cc1]

white solid: LCMS: 494 [M+1]⁺. ¹H NMR (DMSO-d₆) δ: 1.78 (m, 2H), 1.97 (m, 2H), 2.84 (m, 2H), 3.24 (m, 2H), 3.78 (m, 1H), 7.30 (d, 2H), 7.63 (m, 4H), 7.90 (d, 2H), 8.70 (s, 1H), 9.47 (s, 1H).

Example 40

1-(4-Cyanophenyl)-3-(1-(4-(trifluoromethoxy)phenylsulfonyl)piperidin-4-yloxy)urea was prepared as described in EXAMPLE 37

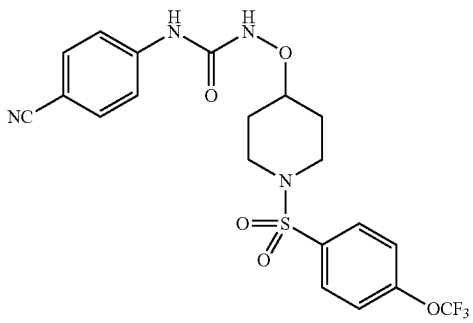 [SMILES: N#Cc1ccc(NC(=O)NOC2CCN(S(=O)(=O)c3ccc(OC(F)(F)F)cc3)CC2)cc1]

white solid: LCMS: 485 [M+1]⁺. ¹H NMR (DMSO-d₆) δ: 1.78 (m, 2H), 1.92 (m, 2H), 2.86 (m, 2H), 3.26 (m, 2H), 3.80 (m, 1H), 7.72 (m, 6H), 7.90 (m, 2H), 9.04 (s, 1H), 9.70 (s, 1H).

Example 41

1-(3-Chlorophenyl)-3-(1-(4-(trifluoromethoxy)phenylsulfonyl)piperidin-4-yloxy)urea was prepared as described in EXAMPLE 37

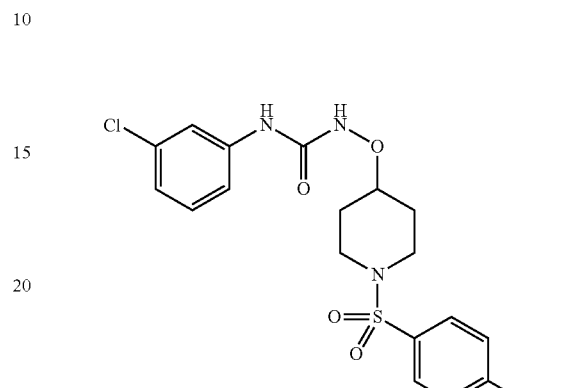

white solid: LCMS: 494 [M+1]⁺. ¹H NMR (DMSO-d₆) δ: 1.78 (m, 2H), 1.94 (m, 2H), 2.83 (m, 2H), 3.26 (m, 2H), 3.78 (m, 1H), 7.45 (m, 6H), 7.90 (m, 2H), 8.74 (s, 1H), 9.53 (s, 1H).

Example 42

1-Cyclohexyl-3-(1-(4-(trifluoromethoxy)phenylsulfonyl)piperidin-4-yloxy)urea was prepared as described in EXAMPLE 37

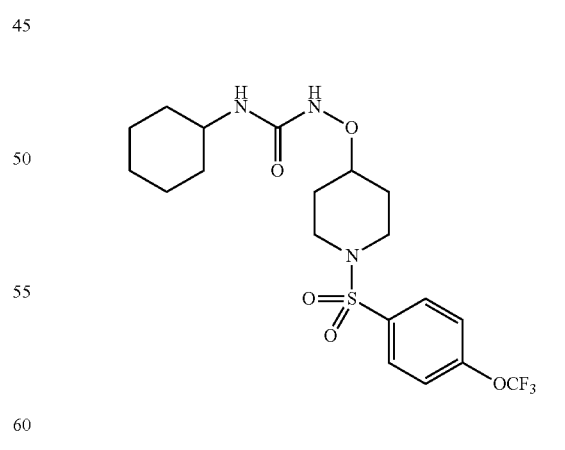

white solid: LCMS: 466 [M+1]⁺. ¹H NMR (DMSO-d₆) δ: 1.08 (m, 1H), 1.18 (m, 4H), 1.55 (d, 1H), 1.68 (m, 6H), 1.83 (m, 2H), 2.82 (m, 2H), 3.14 (m, 2H), 3.35 (m, 1H), 3.62 (m, 1H), 6.18 (d, 1H), 7.62 (d, 2H), 7.86 (d, 2H), 8.81 (s, 1H).

Example 43

1-Cyclopentyl-3-(1-(4-(trifluoromethoxy)phenylsulfonyl)piperidin-4-yloxy)urea was prepared as described in EXAMPLE 37

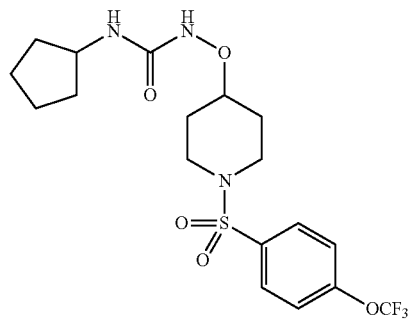 [SMILES: O=C(NOC1CCN(S(=O)(=O)c2ccc(OC(F)(F)F)cc2)CC1)NC1CCCC1]

white solid: LCMS: 452 [M+1]$^+$. $^1$H NMR (DMSO-d$_6$) δ: 1.41 (m, 4H), 1.57 (m, 2H), 1.71 (m, 4H), 1.83 (m, 2H), 2.83 (m, 2H), 3.15 (m, 2H), 3.62 (m, 1H), 3.85 (m, 1H), 6.25 (d, 1H), 7.63 (d, 2H), 7.88 (d, 2H), 8.81 (s, 1H).

Example 44

1-tert-Butyl-3-(1-(4-(trifluoromethoxy)phenylsulfonyl)piperidin-4-yloxy)urea was prepared as described in EXAMPLE 37

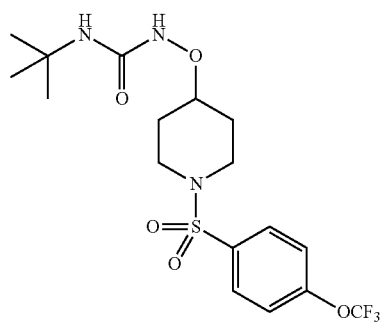 [SMILES: CC(C)(C)NC(=O)NOC1CCN(S(=O)(=O)c2ccc(OC(F)(F)F)cc2)CC1]

white solid: LCMS: 440 [M+1]$^+$. $^1$H NMR (DMSO-d$_6$) δ: 1.19 (s, 9H), 1.65 (m, 2H), 1.85 (m, 2H), 2.86 (m, 2H), 3.09 (m, 2H), 3.64 (m, 1H), 5.67 (s, 1H), 7.62 (d, 2H), 7.87 (d, 2H), 8.72 (s, 1H).

Example 45

1-(4-Fluorobenzyl)-3-(1-(4-(trifluoromethoxy)phenylsulfonyl)piperidin-4-yloxy)urea was prepared as described in EXAMPLE 37

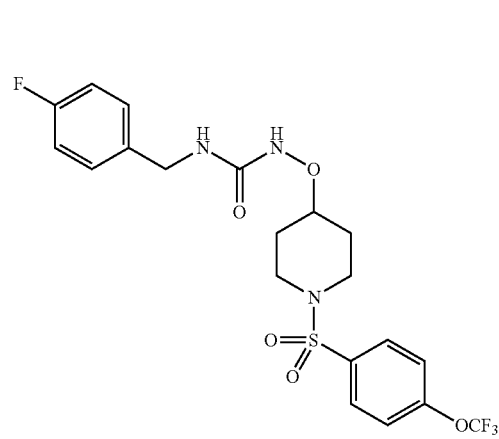 [SMILES: O=C(NCc1ccc(F)cc1)NOC1CCN(S(=O)(=O)c2ccc(OC(F)(F)F)cc2)CC1]

white solid: LCMS: 492 [M+1]$^+$. $^1$H NMR (DMSO-d$_6$) δ: 1.72 (m, 2H), 1.87 (m, 2H), 2.81 (m, 2H), 3.17 (m, 2H), 3.65 (m, 1H), 4.18 (d, 2H), 7.10 (m, 2H), 7.24 (m, 2H), 7.31 (t, 1H), 7.62 (d, 2H), 7.87 (d, 2H), 9.00 (s, 1H).

Example 46

1-(4-Methoxybenzyl)-3-(1-(4-(trifluoromethoxy)phenylsulfonyl)piperidin-4-yloxy)urea was prepared as described in EXAMPLE 37

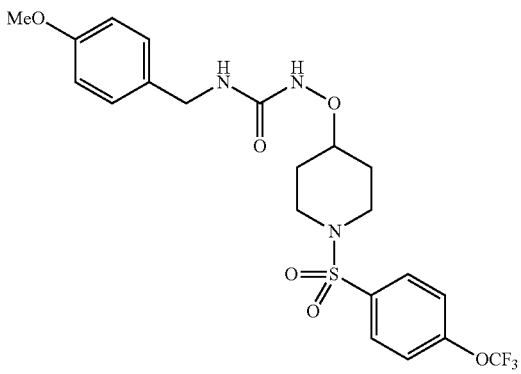 [SMILES: COc1ccc(CNC(=O)NOC2CCN(S(=O)(=O)c3ccc(OC(F)(F)F)cc3)CC2)cc1]

white solid: LCMS: 504 [M+1]$^+$. $^1$H NMR (DMSO-d$_6$) δ: 1.72 (m, 2H), 1.88 (m, 2H), 2.80 (m, 2H), 3.16 (m, 2H), 3.64

(m, 1H), 3.69 (s, 3H), 4.13 (d, 2H), 6.84 (d, 2H), 7.13 (d, 2H), 7.22 (t, 1H), 7.62 (d, 2H), 8.87 (d, 2H), 8.95 (s, 1H).

Example 47

1-(Cyclohexylmethyl)-3-(1-(4-(trifluoromethoxy)phenylsulfonyl)piperidin-4-yloxy)urea was prepared as described in EXAMPLE 37

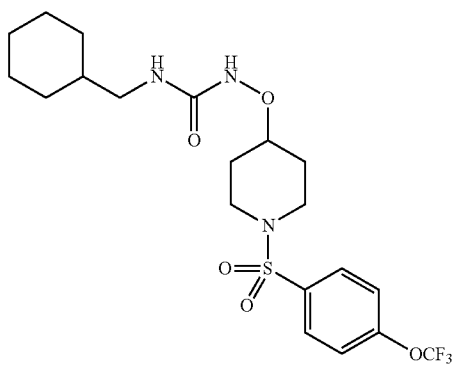 [SMILES: O=C(NCC1CCCCC1)NOC1CCN(S(=O)(=O)c2ccc(OC(F)(F)F)cc2)CC1]

white solid: LCMS: 480 [M+1]⁺. ¹H NMR (DMSO-d$_6$) δ: 0.82 (t, 2H), 1.13 (m, 3H), 1.39 (m, 1H), 1.65 (m, 5H), 1.76 (m, 2H), 1.89 (m, 2H), 2.85 (t, 4H), 3.18 (m, 2H), 3.64 (m, 1H), 6.65 (t, 1H), 7.65 (d, 2H), 7.90 (d, 2H), 8.84 (s, 1H).

Example 48

N-(1-(4-(Trifluoromethoxy)phenylsulfonyl)piperidin-4-yloxy)piperidine-1-carboxamide was prepared as described in EXAMPLE 37

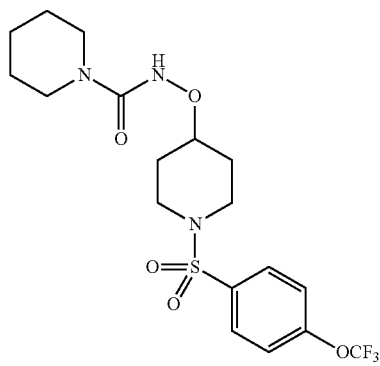 [SMILES: O=C(NOC1CCN(S(=O)(=O)c2ccc(OC(F)(F)F)cc2)CC1)N1CCCCC1]

white solid: LCMS: 452 [M+1]⁺. ¹H NMR (DMSO-d$_6$) δ: 1.37 (m, 4H), 1.49 (m, 2H), 1.67 (m, 2H), 1.81 (m, 2H), 2.97-3.08 (m, 4H), 3.17 (m, 4H), 3.72 (m, 1H), 7.64 (d, 2H), 7.90 (d, 2H), 9.42 (s, 1H).

Example 49

N-(1-(4-(Trifluoromethoxy)phenylsulfonyl)piperidin-4-yloxy)morpholine-4-carboxamide was prepared as described in EXAMPLE 37

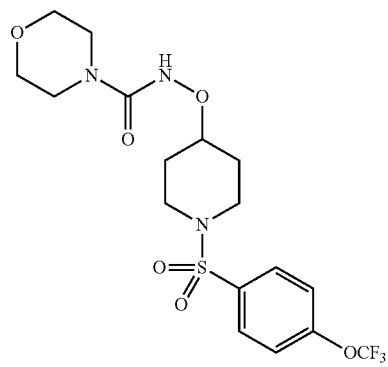 [SMILES: O=C(NOC1CCN(S(=O)(=O)c2ccc(OC(F)(F)F)cc2)CC1)N1CCOCC1]

white solid: LCMS: 454 [M+1]⁺. ¹H NMR (DMSO-d$_6$) δ: 1.67 (m, 2H), 1.83 (m, 2H), 2.98 (m, 2H), 3.06 (m, 2H), 3.18 (m, 4H), 3.50 (m, 4H), 3.74 (m, 1H), 7.64 (d, 2H), 7.90 (d, 2H), 9.57 (s, 1H).

Example 50

1-(Tetrahydro-2H-pyran-4-yl)-3-(1-(4-(trifluoromethoxy)phenylsulfonyl)piperidin-4-yloxy)urea was prepared as described in EXAMPLE 37

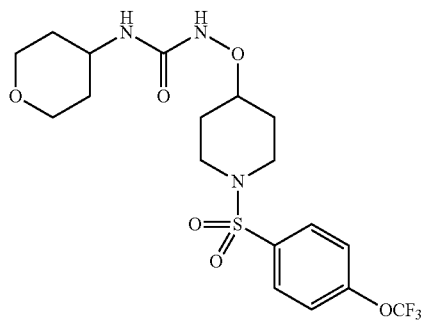 [SMILES: O=C(NOC1CCN(S(=O)(=O)c2ccc(OC(F)(F)F)cc2)CC1)NC1CCOCC1]

white solid: LCMS: 468 [M+1]⁺. ¹H NMR (DMSO-d$_6$) δ: 1.50 (m, 2H), 1.58 (m, 2H), 1.74 (m, 2H), 1.87 (m, 2H), 2.83 (m, 2H), 3.19 (m, 2H), 3.29 (m, 2H), 3.64 (m, 2H), 3.79 (m, 2H), 6.39 (d, 1H), 7.64 (d, 2H), 7.89 (d, 2H), 8.89 (s, 1H).

Example 51

1-(2,2,2-Trifluoroethyl)-3-(1-(4-(trifluoromethoxy)phenylsulfonyl)piperidin-4-yloxy)urea was prepared as described in EXAMPLE 37

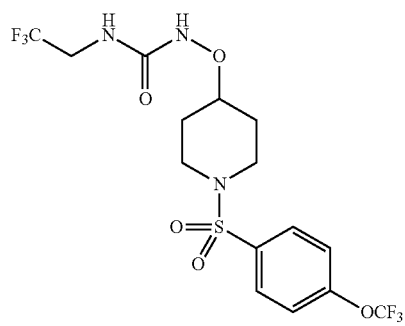 [SMILES: O=C(NCC(F)(F)F)NOC1CCN(S(=O)(=O)c2ccc(OC(F)(F)F)cc2)CC1]

white solid: LCMS: 466 [M+1]+. 1H NMR (DMSO-d6) δ: 1.74 (m, 2H), 1.89 (m, 2H), 2.83 (m, 2H), 3.21 (m, 2H), 3.68 (m, 1H), 3.78 (m, 2H), 7.29 (t, 1H), 7.63 (d, 2H), 7.89 (d, 2H), 9.34 (s, 1H).

Example 52

1-(2-Cyanoethyl)-3-(1-(4-(trifluoromethoxy)phenylsulfonyl)piperidin-4-yloxy)urea was prepared as described in EXAMPLE 37

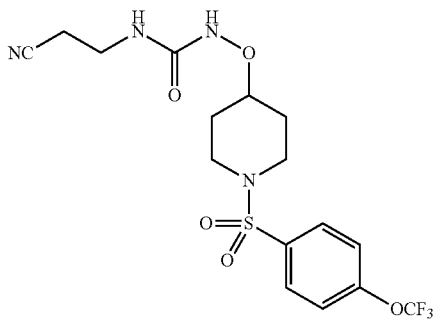

white solid: LCMS: 437 [M+1]+. 1H NMR (DMSO-d6) δ: 1.74 (m, 2H), 1.89 (m, 2H), 2.62 (t, 2H), 2.82 (m, 2H), 3.24 (m, 4H), 3.65 (m, 1H), 7.03 (t, 1H), 7.63 (d, 2H), 7.89 (d, 2H), 9.11 (s, 1H).

Example 53

1-(2-Cyclopropylethyl)-3-(1-(4-(trifluoromethoxy)phenylsulfonyl)piperidin-4-yloxy)urea was prepared as described in EXAMPLE 37

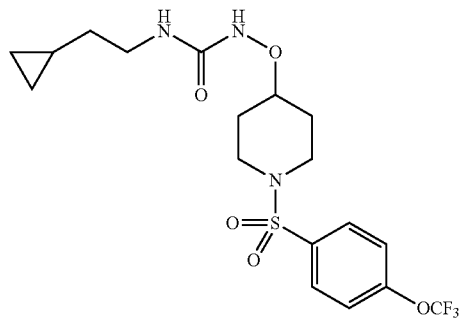 [SMILES: O=C(NCCC1CC1)NOC1CCN(S(=O)(=O)c2ccc(OC(F)(F)F)cc2)CC1]

white solid: LCMS: 452 [M+1]+. 1H NMR (DMSO-d6) δ: 0.00 (m, 2H), 0.36 (m, 2H), 0.61 (m, 1H), 1.29 (m, 2H), 1.70 (m, 2H), 1.87 (m, 2H), 2.83 (m, 2H), 3.08 (m, 2H), 3.18 (m, 2H), 3.63 (m, 1H), 6.63 (t, 1H), 7.63 (d, 2H), 7.89 (d, 2H), 8.83 (s, 1H).

Example 54

1-((Tetrahydrofuran-2-yl)methyl)-3-(1-(4-(trifluoromethoxy)phenylsulfonyl)piperidin-4-yloxy)urea was prepared as described in EXAMPLE 37

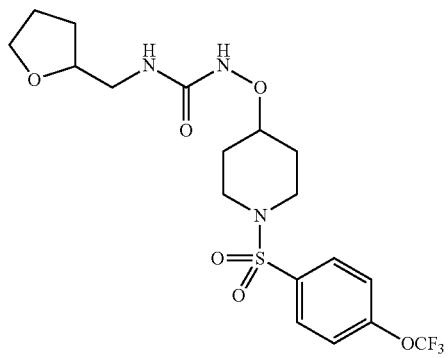 [SMILES: O=C(NCC1CCCO1)NOC1CCN(S(=O)(=O)c2ccc(OC(F)(F)F)cc2)CC1]

white solid: LCMS: 468 [M+1]+. 1H NMR (DMSO-d6) δ: 1.50 (m, 1H), 1.69-1.87 (m, 7H), 2.84 (m, 2H), 3.05 (m, 2H), 3.17 (m, 2H), 3.57-3.82 (m, 6H), 6.60 (t, 1H), 7.64 (d, 2H), 7.89 (d, 2H), 8.95 (s, 1H).

Example 55

1-Cyclobutyl-3-(1-(4-(trifluoromethoxy)phenylsulfonyl)piperidin-4-yloxy)urea was prepared as described in EXAMPLE 37

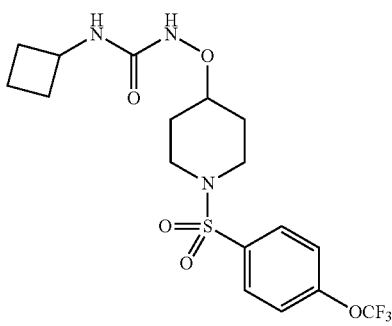 [SMILES: O=C(NOC1CCN(S(=O)(=O)c2ccc(OC(F)(F)F)cc2)CC1)NC1CCC1]

white solid: LCMS: 438 [M+1]+. 1H NMR (DMSO-d6) δ: 1.32 (m, 2H), 1.53 (m, 2H), 1.63-1.86 (m, 6H), 2.61 (m, 2H), 2.97 (m, 2H), 3.42 (m, 1H), 3.86 (m, 1H), 6.50 (d, 1H), 6.60 (t, 1H), 7.42 (d, 2H), 7.67 (d, 2H), 8.64 (s, 1H).

Example 56

1-(2-Methoxyethyl)-3-(1-(4-(trifluoromethoxy)phenylsulfonyl)piperidin-4-yloxy)urea was prepared as described in EXAMPLE 37

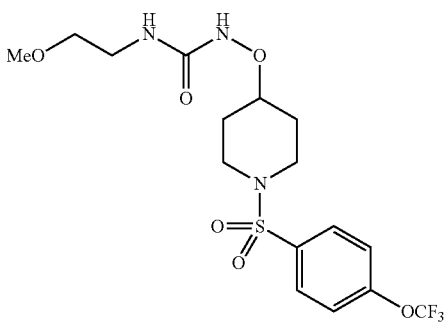 [SMILES: COCCNC(=O)NOC1CCN(S(=O)(=O)c2ccc(OC(F)(F)F)cc2)CC1]

white solid: LCMS: 442 [M+1]+. 1H NMR (DMSO-d6) δ: 1.71 (m, 2H), 1.87 (m, 2H), 2.83 (m, 2H), 3.17 (m, 2H), 3.22 (s, 3H), 3.32 (m, 4H), 3.64 (m, 1H), 6.64 (t, 1H), 7.64 (d, 2H), 7.89 (d, 2H), 8.94 (s, 1H).

Example 57

1-Propyl-3-(1-(4-(trifluoromethoxy)phenylsulfonyl)piperidin-4-yloxy)urea was prepared as described in EXAMPLE 37

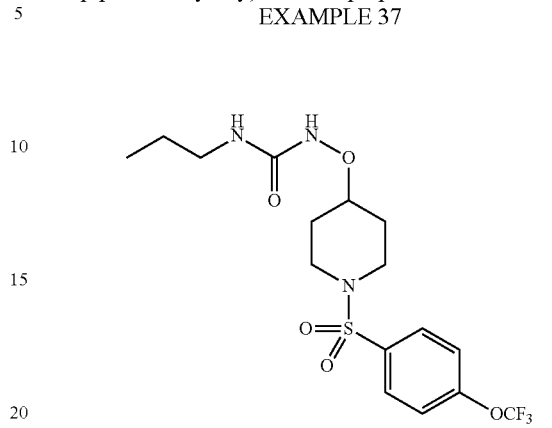

white solid: LCMS: 426 [M+1]+. 1H NMR (DMSO-d6) δ: 0.56 (t, 3H), 1.14 (m, 2H), 1.50 (m, 2H), 1.64 (m, 2H), 2.59 (m, 2H), 2.72 (m, 2H), 2.95 (m, 2H), 3.39 (m, 1H), 6.43 (t, 1H), 7.40 (d, 2H), 7.65 (d, 2H), 8.60 (s, 1H).

Example 58

1-(3-Fluorophenyl)-3-(1-(4-(trifluoromethoxy)phenylsulfonyl)piperidin-4-yloxy)urea

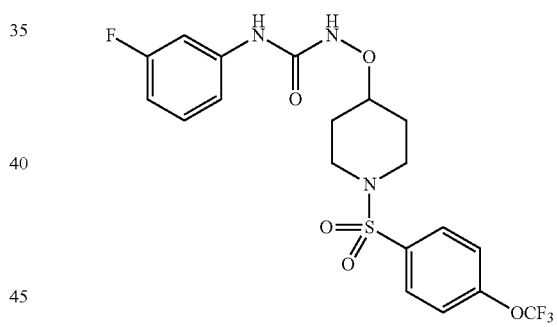

A solution of O-(1-(4-(trifluoromethoxy)phenylsulfonyl)piperidin-4-yl)hydroxylamine (1.02 g, 3.00 mmol) in tetrahydrofuran (20 ml) was added over 1 hour at 0° C. to a solution of trichloromethyl carbonochloridate (890 mg, 4.50 mmol) in tetrahydrofuran (60 ml) and stirred at room temperature for 15 hours. The reaction mixture was concentrated in vacuo and the residue was diluted with tetrahydrofuran (18 ml). 3-Fluoroaniline (100 mg, 0.90 mmol) and N,N-diisopropylethylamine (290 mg, 2.25 mmol) were added and stirred at room temperature for 16 hours. The reaction mixture was quenched with H2O (10 ml) and aqueous 1 N HCl solution (pH=3) and extracted with CH2Cl2 (70 ml×3). The combined organic phase was washed with aqueous NaHCO3 solution and brine, dried over Na2SO4, filtered and concentrated in vacuo. The residue was purified by column chromatography (ethyl acetate/petroleum ether: 33/67) to give 1-(3-fluorophenyl)-3-(1-(4-(trifluoromethoxy)phenylsulfonyl)piperidin-4-yloxy)urea (232 mg, 65%) as a white solid: LCMS: 478 [M+1]+. 1H NMR (DMSO-6) δ: 1.78 (m, 2H), 1.92 (m, 2H), 2.85 (m, 2H), 3.22 (m, 2H), 3.78 (m, 1H), 6.79 (m, 1H), 7.28 (m, 2H), 7.46 (m, 1H), 7.63 (m, 2H), 7.89 (m, 2H), 8.75 (s, 1H), 9.51 (s, 1H).

Example 59

1-(2-Fluorophenyl)-3-(1-(4-(trifluoromethoxy)phenylsulfonyl)piperidin-4-yloxy)urea was prepared as described in EXAMPLE 58

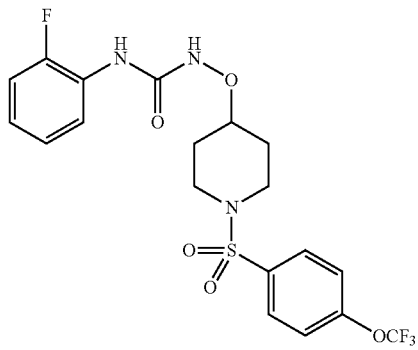 [SMILES: O=C(NOC1CCN(S(=O)(=O)c2ccc(OC(F)(F)F)cc2)CC1)Nc1ccccc1F]

white solid: LCMS: 478 [M+1]$^+$. $^1$H NMR (DMSO-d$_6$) δ: 1.75 (m, 2H), 1.92 (m, 2H), 2.87 (m, 2H), 3.17 (m, 2H), 3.80 (m, 1H), 7.15 (m, 3H), 7.68 (m, 3H), 7.88 (m, 2H), 8.25 (s, 1H), 9.53 (s, 1H).

Example 60

1-(Pyridin-2-yl)-3-(1-(4-(trifluoromethoxy)phenylsulfonyl)piperidin-4-yloxy)urea was prepared as described in EXAMPLE 58

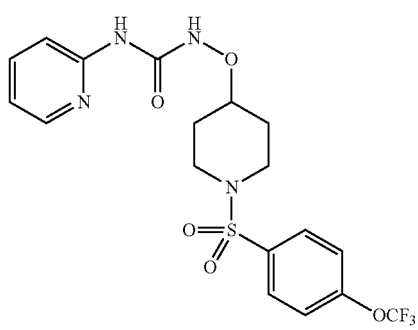 [SMILES: O=C(NOC1CCN(S(=O)(=O)c2ccc(OC(F)(F)F)cc2)CC1)Nc1ccccn1]

white solid: LCMS: 461 [M+1]$^+$. $^1$H NMR (DMSO-$_6$) δ: 1.68 (m, 2H), 1.90 (m, 2H), 2.87 (m, 2H), 3.19 (m, 2H), 3.84 (m, 1H), 6.99 (t, 1H), 7.68 (m, 4H), 7.88 (m, 2H), 8.19 (m, 1H), 8.86 (s, 1H), 10.0 (s, 1H).

Example 61

1-(Pyridin-3-yl)-3-(1-(4-(trifluoromethoxy)phenylsulfonyl)piperidin-4-yloxy)urea was prepared as described in EXAMPLE 58

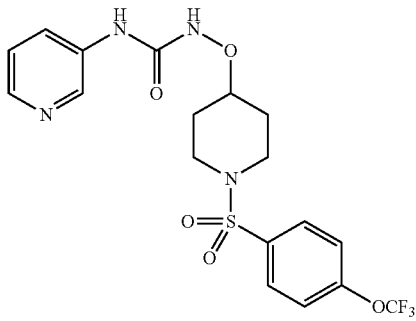 [SMILES: O=C(NOC1CCN(S(=O)(=O)c2ccc(OC(F)(F)F)cc2)CC1)Nc1cccnc1]

white solid: LCMS: 461 [M+1]$^+$. $^1$H NMR (DMSO-$_6$) δ: 1.79 (m, 2H), 1.91 (m, 2H), 2.82 (m, 2H), 3.22 (m, 2H), 3.77 (m, 1H), 7.26 (m, 1H), 7.63 (m, 2H), 7.89 (m, 3H), 8.18 (m, 1H), 8.65 (m, 1H), 8.77 (s, 1H), 9.56 (s, 1H).

Example 62

1-(4-Methoxyphenyl)-3-(1-(4-(trifluoromethoxy)phenylsulfonyl)piperidin-4-yloxy)urea was prepared as described in EXAMPLE 58

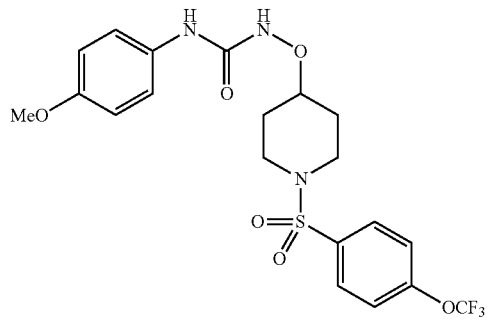 [SMILES: COc1ccc(NC(=O)NOC2CCN(S(=O)(=O)c3ccc(OC(F)(F)F)cc3)CC2)cc1]

white solid: LCMS: 490 [M+1]+. $^1$H NMR (DMSO-$_6$) δ: 1.77 (m, 2H), 1.91 (m, 2H), 2.83 (t, 2H), 3.20 (m, 2H), 3.73

(m, 4H), 6.82 (m, 2H), 7.34 (m, 2H), 7.62 (d, 2H), 7.89 (m, 2H), 8.41 (s, 1H), 9.23 (s, 1H).

Example 63

1-(3-Cyanophenyl)-3-(1-(4-(trifluoromethoxy)phenylsulfonyl)piperidin-4-yloxy)urea was prepared as described in EXAMPLE 58

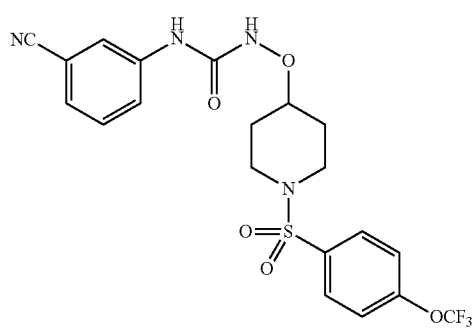 [SMILES: N#Cc1cccc(NC(=O)NOC2CCN(S(=O)(=O)c3ccc(OC(F)(F)F)cc3)CC2)c1]

white solid: LCMS: 485 [M+1]+. 1H NMR (DMSO-d6) δ: 1.77 (m, 2H), 1.93 (d, 2H), 2.82 (m, 2H), 3.24 (m, 2H), 3.78 (m, 1H), 7.44 (m, 2H), 7.61 (t, 2H), 7.85 (m, 3H), 7.89 (m, 1H), 8.88 (s, 1H), 9.63 (s, 1H).

Example 64

1-(3-Methoxyphenyl)-3-(1-(4-(trifluoromethoxy) phenylsulfonyl)piperidin-4-yloxy)urea was prepared as described in EXAMPLE 58

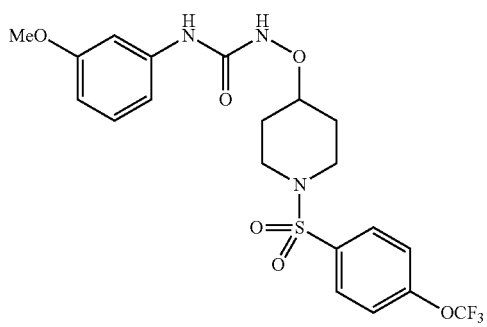 [SMILES: COc1cccc(NC(=O)NOC2CCN(S(=O)(=O)c3ccc(OC(F)(F)F)cc3)CC2)c1]

white solid: LCMS: 490 [M+1]+. 1H NMR (DMSO-d6) δ: 1.77 (m, 2H), 1.93 (m, 2H), 2.82 (t, 2H), 3.22 (m, 2H), 3.73 (m, 4H), 6.55 (m, 1H), 7.13 (m, 3H), 7.62 (d, 2H), 7.89 (t, 2H), 8.50 (s, 1H), 9.36 (s, 1H).

Example 65

1-(6-Methoxypyridin-3-yl)-3-(1-(4-(trifluoromethoxy)phenylsulfonyl)piperidin-4-yloxy)urea was prepared as described in EXAMPLE 58

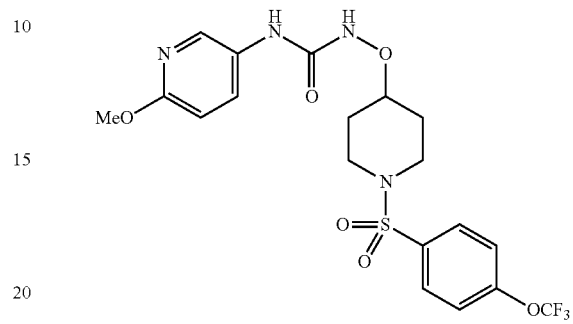

white solid: LCMS: 491 [M+1]+. 1H NMR (DMSO-d6) δ: 1.79 (m, 2H), 1.92 (m, 2H), 2.82 (t, 2H), 3.21 (t, 2H), 3.74 (m, 4H), 6.73 (d, 1H), 7.63 (t, 2H), 7.76 (m, 1H), 7.87 (m, 2H), 8.19 (d, 1H), 8.59 (s, 1H), 9.41 (s, 1H).

Example 66

1-(4-Fluorophenyl)-3-(1-(4-(trifluoromethoxy)phenylsulfonyl)piperidin-4-yloxy)urea

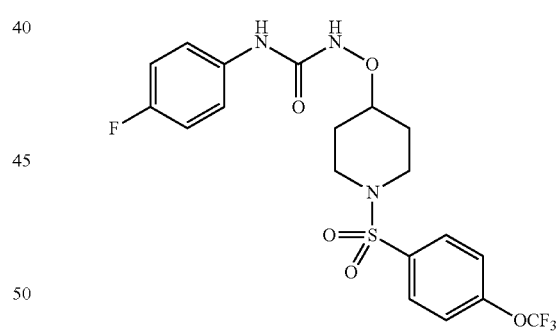

1-Fluoro-4-isocyanatobenzene (96 mg, 0.70 mmol) was added to a solution of O-(1-(4-(trifluoromethoxy)phenylsulfonyl)piperidin-4-yl) hydroxylamine (238 mg, 0.70 mmol) and pyridine (111 mg, 2.1 mmol) in CH2Cl2 (6 ml), and the whole was stirred at room temperature for 17 hours. The resulting precipitation was collected, washed with aqueous 1 N HCl solution (10 ml×3), aqueous NaHCO3 solution (10 ml×3), diethyl ether (10 ml×2) to give 1-(4-fluorophenyl)-3-(1-(4-(trifluoromethoxy)phenylsulfonyl)piperidin-4-yloxy) urea (110 mg, 33%) as a white solid: LCMS: 478 [M+1]+. 1H NMR (DMSO-d6) δ: 1.81 (m, 2H), 1.92 (m, 2H), 2.85 (m, 2H), 3.22 (m, 2H), 3.78 (m, 1H), 7.10 (m, 2H), 7.51 (m, 2H), 7.65 (m, 2H), 7.91 (m, 2H), 8.62 (s, 1H), 9.38 (s, 1H).

Example 67

1-(1-(4-(Trifluoromethoxy)phenylsulfonyl)piperidin-4-yloxy)-3-(3,3,3-trifluoropropyl)urea

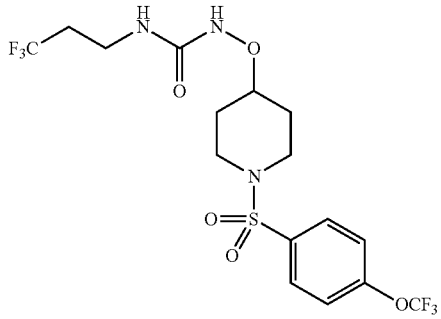 [SMILES: O=C(NCCC(F)(F)F)NOC1CCN(S(=O)(=O)c2ccc(OC(F)(F)F)cc2)CC1]

Diphenyl phosphorazidate (0.108 ml, 0.50 mmol) was added to a solution of 4,4,4-trifluorobutanoic acid (71.0 mg, 0.50 mmol) and triethylamine (0.076 ml, 0.55 mmol) in toluene (3 ml) and the whole was stirred at 80° C. for 1 hour. After cooling to room temperature, tetrahydrofuran (3 ml) and O-1-(4-(trifluoromethoxy)phenylsulfonyl)piperidin-4-yl)hydroxylamine (170 mg, 0.50 mmol) were added and stirred for 2 hours. The reaction mixture was concentrated in vacuo and the residue was diluted with ethyl acetate, washed with $H_2O$, aqueous 0.3N HCl solution, aqueous $NaHCO_3$ solution, dried over $MgSO_4$ and concentrated in vacuo. The residue was purified by column chromatography (chloroform/methanol: 100/0 to 95/5) and the resulting solid was recrystallized from ethyl acetate/hexane to give 1-(1-(4-(trifluoromethoxy)phenylsulfonyl)piperidin-4-yloxy)-3-(3,3,3-trifluoropropyl)urea (188 mg, 78%) as a white solid: LCMS: 480 [M+1]$^+$. $^1$H NMR (DMSO-d$_6$) δ: 1.70 (m, 2H), 1.87 (m, 2H), 2.43 (m, 2H), 2.82 (m, 2H), 3.17-3.33 (m, 4H), 3.63 (m, 1H), 6.87 (t, 1H), 7.64 (d, 2H), 7.89 (d, 2H), 9.05 (s, 1H).

Example 68

1-(4-Fluorophenyl)-3-(1-(piperidin-1-ylsulfonyl)piperidin-4-yloxy)urea

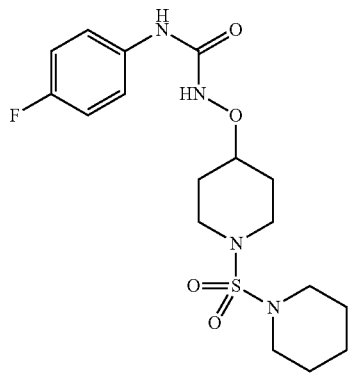 [SMILES: O=C(NOC1CCN(S(=O)(=O)N2CCCCC2)CC1)Nc1ccc(F)cc1]

a) Hydrazine solution (1.40 g, 29.0 mmol) was added to a solution of tert-butyl 4-(1,3-dioxoisoindolin-2-yloxy)piperidine-1-carboxylate (5.00 g, 14.5 mmol) in ethanol (50 ml) and stirred at room temperature for 30 minutes. The resulting solid was filtered off and the filtrate was concentrated in vacuo. The residue was triturated with diethyl ether (30 ml), and the resulting solid was filtered off again and concentrated in vacuo to give tert-butyl 4-(aminooxy)piperidine-1-carboxylate (2.75 g, 88%) as a white solid.

b) A solution of tert-butyl 4-(aminooxy)piperidine-1-carboxylate (2.0 g, 9.2 mmol) in tetrahydrofuran (10 ml) was added over 30 minutes to a suspension of trichloromethyl chloroformate (2.74 g, 13.8 mmol) and activated charcoal (20 mg) in tetrahydrofuran (35 ml) at 0° C. over 30 minutes. After stirring at room temperature for 17 hours, the reaction mixture was filtered over silicagel and the filtrate was concentrated in vacuo. The residue was dissolved in tetrahydrofuran (15 ml), 4-fluoroaniline (2.0 g, 18.4 mmol) and N,N-diisopropylethylamine (3.58 g, 27.6 mmol) were added and the whole was stirred at room temperature for 17 hours. The reaction mixture was concentrated in vacuo and the residue was diluted with ethyl acetate (50 ml), washed with $H_2O$ (20 ml×2), brine (20 ml×2), dried over $Na_2SO_4$ and concentrated in vacuo. The residual solid was recrystallized from diethyl ether to give tert-butyl 4-(3-(4-fluorophenyl)ureidooxy)piperidine-1-carboxylate (2.19 g, 67%) as a white solid: LCMS: 354 [M+1]$^+$.

c) A mixture of tert-butyl 4-(3-(4-fluorophenyl)ureidooxy)piperidine-1-carboxylate (1.5 g, 4.2 mmol) and 1 N HCl solution in dioxane (25 ml) was stirred at room temperature for 3 hours and concentrated in vauo. The residual solid was triturated with diethyl ether (100 ml) to give 1-(4-fluorophenyl)-3-(piperidin-4-yloxy)urea hydrochloride (1.1 g, 90%) as a white solid.

d) A solution of piperidine (300 mg, 3.5 mmol) in $CH_2Cl_2$ (10 ml) was added at 0° C. over 30 minutes to a suspension of sulfuryl dichloride (952 mg, 7.0 mmol) in $CH_2Cl_2$ (35 ml) and the whole was stirred at room temperature for 17 hours. The resulting solid was filtered off and the filtrate was concentrated in vacuo. The residue was dissolved in $CH_2Cl_2$ (15 ml), 1-(4-fluorophenyl)-3-(piperidin-4-yloxy)urea hydrochloride (130 mg, 0.45 mmol) and N,N-diisopropylethylamine (174 mg, 1.35 mmol) was added, and the whole was stirred at 50° C. for 24 hours. The reaction mixture was concentrated in vacuo and the residue was diluted with ethyl acetate (50 ml), washed with $H_2O$ (20 ml×2), brine (20 ml×2), dried over $Na_2SO_4$ and concentrated in vacuo. The residue was purified by column chromatography (ethyl acetate/petroleum ether: 50/50) to give 1-(4-fluorophenyl)-3-(1-(piperidin-1-ylsulfonyl)piperidin-4-yloxy)urea (90 mg, 50%) as a white solid: LCMS: 401 [M+1]$^+$. $^1$H NMR (DMSO-d$_6$) δ: 1.48 (s, 6H), 1.7 (m, 2H), 1.89 (m, 2H), 2.98 (m, 2H), 3.1 (m, 4H), 3.4 (m, 2H), 3.87 (m, 1H), 7.08 (t, 2H), 7.86 (m, 2H), 8.65 (s, 1H), 9.42 (s, 1H).

Example 69

1-(4-Fluorophenyl)-3-(1-(morpholinosulfonyl)piperidin-4-yloxy)urea was prepared as described in EXAMPLE 68

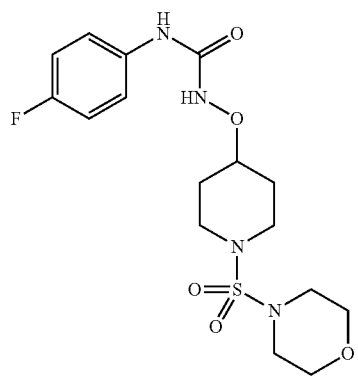 [SMILES: O=C(NOC1CCN(S(=O)(=O)N2CCOCC2)CC1)Nc1ccc(F)cc1]

white solid: LC-MS: 403 [M+1]⁺. ¹H NMR (DMSO-d₆) δ: 1.31 (m, 2H), 1.92 (m, 2H), 3.07 (m, 6H), 3.48 (m, 2H), 3.35 (t, 4H), 3.82 (m, 1H), 7.09 (t, 2H), 7.54 (q, 2H), 8.66 (s, 1H), 9.42 (s, 1H).

Example 70

1-(4-Fluorophenyl)-3-(1-(4-methylpiperidin-1-ylsulfonyl)piperidin-4-yloxy)urea was prepared as described in EXAMPLE 68

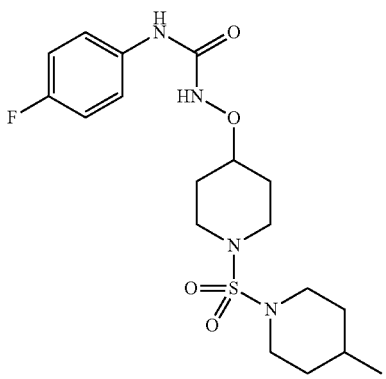 [SMILES: CC1CCN(S(=O)(=O)N2CCC(ONC(=O)Nc3ccc(F)cc3)CC2)CC1]

white solid: LC-MS: 415 [M+1]⁺. ¹H NMR (DMSO-d₆) δ: 0.87 (s, 3H), 1.02 (m, 2H), 1.46 (m, 1H), 1.67 (m, 4H), 1.96 (m, 2H), 2.72 (t, 2H), 2.97 (m, 2H), 3.51 (m, 4H), 3.82 (m, 1H), 7.09 (t, 2H), 7.54 (q, 2H), 8.65 (s, 1H), 9.41 (s, 1H).

Example 71

1-(1-(3,5-Dimethylpiperidin-1-ylsulfonyl)piperidin-4-yloxy)-3-(4-fluorophenyl)urea was prepared as described in EXAMPLE 68

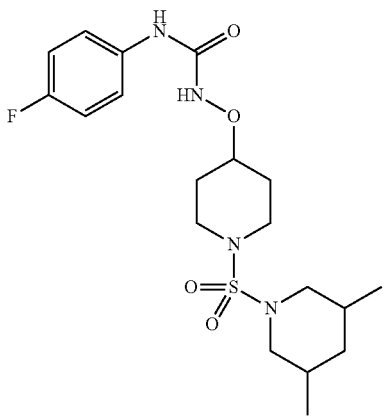 [SMILES: CC1CC(C)CN(S(=O)(=O)N2CCC(ONC(=O)Nc3ccc(F)cc3)CC2)C1]

white solid: LC-MS: 429 [M+1]⁺. ¹H NMR (DMSO-d₆) δ: 0.87 (m, 6H), 0.89 (m, 1H), 1.55 (m, 2H), 1.67 (m, 3H), 1.89 (m, 2H), 2.25 (t, 2H), 2.98 (m, 2H), 3.46 (m, 4H), 3.81 (m, 1H), 7.11 (t, 2H), 7.54 (m, 2H), 8.66 (s, 1H), 9.43 (s, 1H).

Example 72

1-(1-(Azepan-1-ylsulfonyl)piperidin-4-yloxy)-3-(4-fluorophenyl)urea was prepared as described in EXAMPLE 68

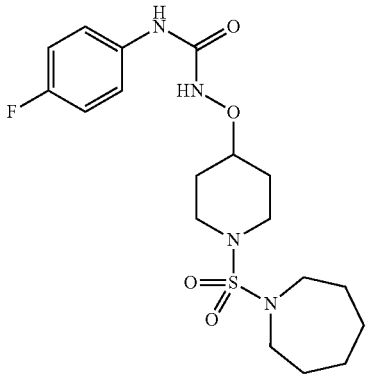 [SMILES: O=C(NOC1CCN(S(=O)(=O)N2CCCCCC2)CC1)Nc1ccc(F)cc1]

white solid: LC-MS: 415 [M+1]⁺. ¹H NMR (DMSO-d₆) δ: 1.51 (m, 4H), 1.67 (m, 4H), 1.72 (m, 2H), 1.93 (m, 2H), 2.91 (m, 2H), 3.28 (m, 4H), 3.33 (m, 2H), 3.81 (m, 1H), 7.09 (t, 2H), 7.54 (q, 2H), 8.64 (s, 1H), 9.41 (s, 1H).

Example 73

1-(4-Fluorophenyl)-3-(1-(4-methylpiperazin-1-ylsulfonyl)piperidin-4-yloxy)urea a) Sulfuryl dichloride (1.22 ml, 15.0 mmol) was added at room temperature to a solution of N-methylpiperazine (0.555 ml, 5.00 mmol) in acetonitrile (10 ml) and the whole was stirred under reflux for 6 hours. The reaction mixture was concentrated in vacuo and the resulting solid was collected and washed with diethyl ether to give 4-methylpiperazine-1-sulfonyl chloride hydrochloride.

b) 4-Methylpiperazine-1-sulfonyl chloride hydrochloride (227 mg, 0.966 mmol) was added at room temperature to a solution of 1-(4-fluorophenyl)-3-(piperidin-4-yloxy)urea hydrochloride (140 mg, 0.483 mmol) and K₂CO₃ (200 mg, 1.45 mmol) in H₂O-dioxane (1:1, 4 ml), and the whole was stirred at room temperature for 18 hours. The reaction was quenched with K₂CO₃ (200 mg) in H₂O (10 ml), extracted with ethyl acetate (20 ml×3). The combined organic layer was washed with brine (10 ml), dried over Na₂SO₄, filtered and concentrated in vacuo. The residue was purified by column chromatography (chloroform/methanol: 90/10) to give 1-(4- fluorophenyl)-3-(1-(4-methylpiperazin-1-ylsulfonyl)piperidin-4-yloxy)urea (139 mg, 69%) as pale yellow amorphous: LCMS: 416 [M+1]$^+$. $^1$H NMR (DMSO-d$_6$) δ: 1.72 (m, 2H), 1.93 (m, 2H), 2.19 (s, 3H), 2.35 (m, 4H), 3.01-3.13 (m, 6H), 3.45 (m, 2H), 3.85 (m, 1H), 7.11 (m, 2H), 7.55 (m, 2H), 8.68 (s, 1H), 9.45 (s, 1H).

Example 74 rac-1-(1-((2S,6R)-2,6-Dimethylmorpholinosulfonyl)piperidin-4-yloxy)-3-(4-fluorophenyl)urea

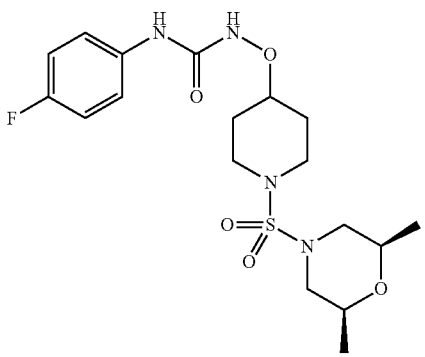 [SMILES: C[C@@H]1CN(S(=O)(=O)N2CCC(ONC(=O)Nc3ccc(F)cc3)CC2)C[C@H](C)O1]

a) Sulfuryl dichloride (0.363 ml, 4.47 mmol) was added at room temperature to a solution of cis-2,6-dimethylmorpholine (0.500 ml, 4.06 mmol) and 4-dimethylaminopyridine (496 mg, 4.06 mmol) in CH$_2$Cl$_2$ (5 ml) and the whole was stirred at room temperature for 24 hours. The reaction mixture was quenched with H$_2$O (10 ml) and extracted with ethyl acetate (20 ml×3). The combined organic layer was washed with brine (10 ml), dried over Na$_2$SO$_4$, filtered and concentrated in vacuo to give cis-2,6-dimethylmorpholine-4-sulfonyl chloride.

b) rac-1-(1-((2S,6R)-2,6-Dimethylmorpholinosulfonyl)piperidin-4-yloxy)-3-(4-fluorophenyl)urea was prepared as described in Example 73 white solid: LC-MS: 431 [M+1]$^+$. $^1$H NMR (DMSO-d$_6$) δ: 1.09 (d, 6H), 1.73 (m, 2H), 1.95 (m, 2H), 2.44 (m, 2H), 3.06 (m, 2H), 3.33-3.58 (m, 6H), 3.85 (m, 1H), 7.10 (m, 2H), 7.55 (m, 2H), 8.69 (s, 1H), 9.45 (s, 1H).

Example 75

1-(4-Fluorophenyl)-3-(1-(3-(trifluoromethyl)piperidin-1-ylsulfonyl)piperidin-4-yloxy)urea was prepared as described in EXAMPLE 74

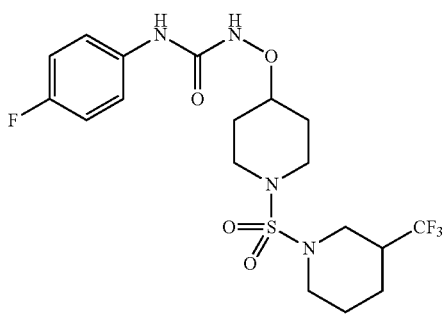 [SMILES: O=C(NOC1CCN(S(=O)(=O)N2CCCC(C(F)(F)F)C2)CC1)Nc1ccc(F)cc1]

white solid: LC-MS: 469 [M+1]$^+$. $^1$H NMR (DMSO-d$_6$) δ: 1.39-1.53 (m, 2H), 1.73 (m, 3H), 1.93 (m, 3H), 2.57 (m, 1H), 2.85 (m, 2H), 3.03 (m, 2H), 3.46-3.66 (m, 4H), 3.85 (H, m), 7.11 (m, 2H), 7.55 (m, 2H), 8.69 (s, 1H), 9.45 (s, 1H).

Example 76

1-(4-Fluorophenyl)-3-(1-(3-methylpiperidin-1-ylsulfonyl)piperidin-4-yloxy)urea was prepared as described in EXAMPLE 74

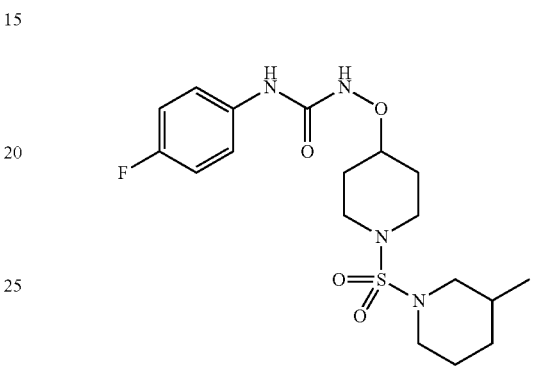

white solid: LC-MS: 415 [M+1]$^+$. $^1$H NMR (DMSO-d$_6$) δ: 0.86 (d, 3H), 1.01 (m, 1H), 1.39-1.74 (m, 6H), 1.93 (m, 2H), 2.42 (m, 1H), 2.73 (m, 1H), 3.00 (m, 2H), 3.44 (m, 4H), 3.84 (m, 1H), 7.11 (mt, 2H), 7.56 (m, 2H), 8.68 (s, 1H), 9.44 (s, 1H).

Example 77

1-(1-(Azocan-1-ylsulfonyl)piperidin-4-yloxy)-3-(4-fluorophenyl)urea was prepared as described in EXAMPLE 74

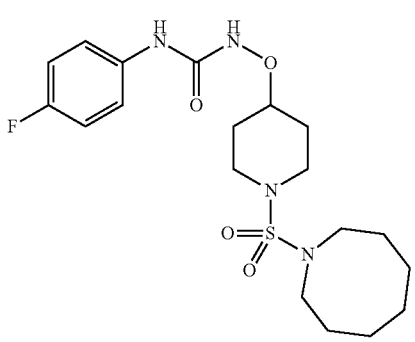 [SMILES: O=C(NOC1CCN(S(=O)(=O)N2CCCCCCC2)CC1)Nc1ccc(F)cc1]

white solid: LC-MS: 429 [M+1]$^+$. $^1$H NMR (DMSO-d$_6$) δ: 1.55-1.76 (m, 12H), 1.94 (m, 2H), 2.94 (m, 2H), 3.22-3.38 (m, 6H), 3.83 (m, 1H), 7.10 (m, 2H), 7.55 (m, 2H), 8.67 (s, 1H), 9.44 (s, 1H).

Example 78

1-(1-(1,4-Oxazepan-4-ylsulfonyl)piperidin-4-yloxy)-3-(4-fluorophenyl)urea

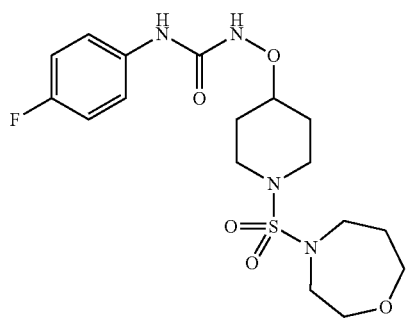 [SMILES: O=C(NOC1CCN(S(=O)(=O)N2CCCOCC2)CC1)Nc1ccc(F)cc1]

a) Sulfuryl dichloride (0.078 ml, 0.96 mmol) was added at room temperature to a solution of homomorphorine hydrochloride (120 mg, 0.872 mmol) and 4-dimethylaminopyridine (213 mg, 1.74 mmol) in $CH_2Cl_2$ (2 ml) and the whole was stirred at room temperature for 3.5 hours. The reaction mixture was quenched with $H_2O$ (10 ml) and extracted with ethyl acetate (20 ml×3). The combined organic layer was washed with brine (10 ml), dried over $Na_2SO_4$, filtered and concentrated in vacuo to give homomorpholine-4-sulfonyl chloride.

b) 1-(1-(1,4-Oxazepan-4-ylsulfonyl)piperidin-4-yloxy)-3-(4-fluorophenyl)urea was prepared as described in EXAMPLE 73 white solid: LC-MS: 417 [M+1]$^+$. $^1$H NMR (DMSO-$d_6$) δ: 1.74 (m, 2H), 1.82 (m, 2H), 1.94 (m, 2H), 2.96 (m, 2H), 3.33-3.42 (m, 6H), 3.66 (m, 4H), 3.84 (m, 1H), 7.11 (m, 2H), 7.56 (m, 2H), 8.68 (s, 1H), 9.45 (s, 1H).

Example 79

1-(4-Fluorophenyl)-3-(1-(2-methylpyrrolidin-1-ylsulfonyl)piperidin-4-yloxy)urea was prepared as described in EXAMPLE 78

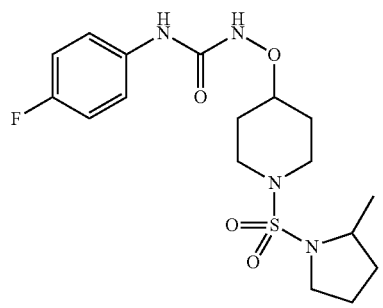 [SMILES: CC1CCCN1S(=O)(=O)N1CCC(ONC(=O)Nc2ccc(F)cc2)CC1]

brownish solid: LC-MS: 401 [M+1]$^+$. $^1$H NMR (DMSO-$d_6$) δ: 1.15 (d, 3H), 1.53 (m, 1H), 1.69-2.03 (m, 7H), 2.97 (m, 2H), 3.22 (m, 2H), 3.40 (m, 2H), 3.76-3.86 (m, 2H), 7.11 (m, 2H), 7.56 (m, 2H), 8.68 (s, 1H), 9.44 (s, 1H).

Example 80

1-(1-(4,4-Difluoropiperidin-1-ylsulfonyl)piperidin-4-yloxy)-3-(4-fluorophenyl)urea was prepared as described in EXAMPLE 78

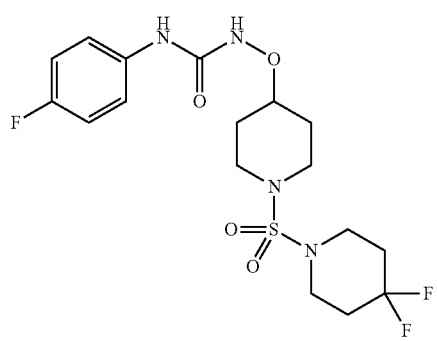 [SMILES: O=C(NOC1CCN(S(=O)(=O)N2CCC(F)(F)CC2)CC1)Nc1ccc(F)cc1]

white solid: LC-MS: 437 [M+1]$^+$. $^1$H NMR (DMSO-$d_6$) δ: 1.73 (m, 2H), 1.94-2.09 (m, 6H), 3.04 (m, 2H), 3.29-3.33 (m, 2H), 3.45 (m, 2H), 3.86 (m, 1H), 7.11 (m, 2H), 7.56 (m, 2H), 8.69 (s, 1H), 9.45 (s, 1H).

Example 81

1-(4-Fluorophenyl)-3-(1-(4-methoxypiperidin-1-ylsulfonyl)piperidin-4-yloxy)urea was prepared as described in EXAMPLE 78

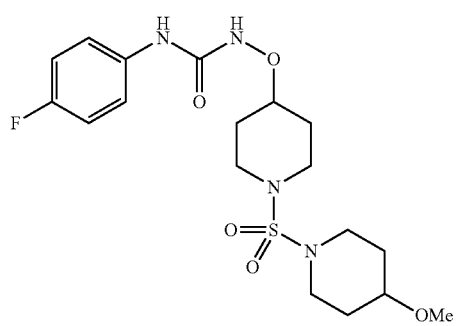 [SMILES: COC1CCN(S(=O)(=O)N2CCC(ONC(=O)Nc3ccc(F)cc3)CC2)CC1]

pale yellow solid: LC-MS: 431 [M+1]$^+$. $^1$H NMR (DMSO-$d_6$) δ: 1.48 (m, 2H), 1.68-1.99 (m, 6H), 3.00 (m, 4H), 3.24 (s, 3H), 3.32-3.44 (m, 5H), 3.85 (m, 1H), 7.11 (m, 2H), 7.55 (m, 2H), 8.68 (s, 1H), 9.45 (s, 1H).

Example 82

1-(1-(3,3-Difluoropiperidin-1-ylsulfonyl)piperidin-4-yloxy)-3-(4-fluorophenyl)urea was prepared as described in EXAMPLE 78

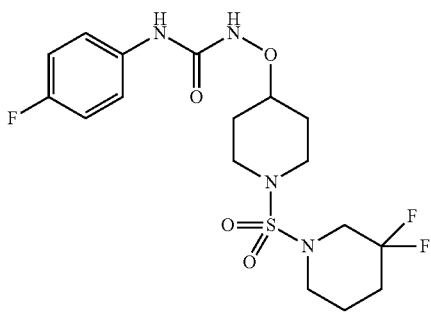 [SMILES: O=C(NOC1CCN(S(=O)(=O)N2CCCC(F)(F)C2)CC1)Nc1ccc(F)cc1]

white solid: LC-MS: 437 [M+1]⁺. ¹H NMR (DMSO-$d_6$) δ: 1.74 (m, 4H), 1.99 (m, 4H), 3.03 (m, 2H), 3.22 (m, 2H), 3.46 (m, 4H), 3.85 (m, 1H), 7.11 (m, 2H), 7.55 (m, 2H), 8.68 (s, 1H), 9.46 (s, 1H).

Example 83

1-(4-Fluorophenyl)-3-(1-(pyrrolidin-1-ylsulfonyl)piperidin-4-yloxy)urea was prepared as described in EXAMPLE 78

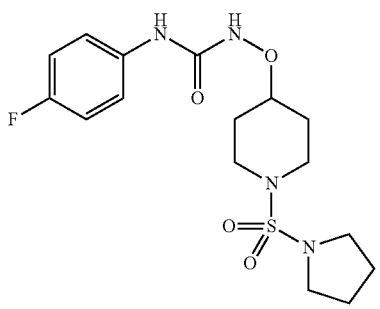 [SMILES: O=C(NOC1CCN(S(=O)(=O)N2CCCC2)CC1)Nc1ccc(F)cc1]

pale yellow solid: LC-MS: 387 [M+1]⁺. ¹H NMR (DMSO-$d_6$) δ: 1.73 (m, 2H), 1.83 (m, 4H), 1.94 (m, 2H), 2.99 (m, 2H), 3.32 (m, 4H), 3.43 (m, 2H), 3.85 (m, 1H), 7.11 (m, 2H), 7.55 (m, 2H), 8.68 (s, 1H), 9.45 (s, 1H).

Example 84

(S)-1-Ethyl-3-(1-(3-(trifluoromethyl)phenylsulfonyl)pyrrolidin-3-yloxy)urea

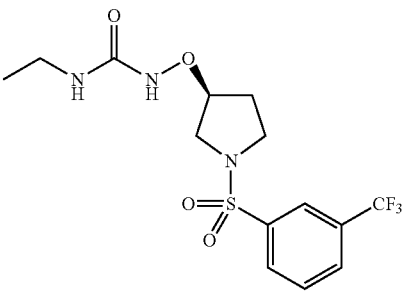 [SMILES: CCNC(=O)NO[C@H]1CCN(S(=O)(=O)c2cccc(C(F)(F)F)c2)C1]

a) Diethyl azodicarboxylate (17.4 g, 100 mmol) was added to a solution of (R)-tert-butyl-3-hydroxypyrrolidin-1-carboxylate (9.40 g, 50 mmol), 2-hydroxyisoindoline-1,3-dione (8.16 g, 50 mmol) and triphenylphosphine (26.2 g, 100 mmol) in tetrahydrofuran (100 ml) at 0° C. The reaction mixture was stirred at room temperature for 17 hours and concentrated in vacuo. The residue was purified by column chromatography (ethyl acetate/petroleum ether: 5/95 to 12.5/87.5) to give (S)-tert-butyl 3-(1,3-dioxoisoindolin-2-yloxy)pyrrolidin-1-carboxylate (6.74 g, 20%) as a white solid: LCMS: 277 [M−55]⁺ b) Trifluoroacetic acid (3.42 g, 30 mmol) was added at 0° C. to a solution of (S)-tert-butyl 3-(1,3-dioxoisoindolin-2-yloxy)pyrrolidin-1-carboxylate (3.32 g, 10 mmol) in CH₂Cl₂ (25 ml), and the whole was stirred at room temperature for 17 hours. The reaction was concentrated in vacuo and the residue was triturated with diethyl ether (100 ml) to give (S)-2-(pyrrolidin-3-yloxy)isoindoline-1,3-dione) trifluoroacetic acid salt (2.77 g, 80%) as a white solid.

c) 3-(Trifluoromethyl)benzene-1-sulyl chloride (1.96 g, 8 mmol) was added to a solution of (S)-2-(pyrrolidin-3-yloxy)isoindoline-1,3-dione)trifluoroacetic acid salt (2.77 g, 8 mmol) and N,N-diisopropylethylamine (3.10 g, 24 mmol) in CH₂Cl₂ (50 ml), and the whole was stirred at room temperature for 4 hours. The reaction mixture was washed with aqueous 1 N HCl solution (50 ml×2), H₂O (50 ml×3), brine (50 ml), dried over Na₂SO₄, filtered and concentrated in vacuo. The residue was purified by column chromatography (ethyl acetate/petroleum ether: 12.5/87.5 to 50/50) to give (S)-2-(1-(3-(trifluoromethyl)phenylsulfonyl)pyrrolidin-3-yloxy)isoindoline-1,3-dione (1.87 g, 53%) as a white solid.

d) A solution of (S)-2-(1-(3-(trifluoromethyl)phenylsulfonyl)pyrrolidin-3-yloxy)isoindoline-1,3-dione (3.74 g, 8.40 mmol) and hydrazine solution (0.373 g, 9.3 mmol) in ethanol (16 ml) was stirred at room temperature for 1 hour. The reaction mixture was concentrated in vacuo, the resulting solid was filtered off and washed with diethyl ether (30 ml), and the filtrate was concentrated in vacuo to give (S)—O-(1-(3-(trifluoromethyl)phenylsulfonyl)pyrrolidin-3-yl)hydroxylamine (2.37 g, 90%) as greenish oil.

e) Isocyanatoethane (36.0 mg, 0.5 mmol) was added to a solution of (S)—O-(1-(3-(trifluoromethyl)phenylsulfonyl)pyrrolidin-3-yl)hydroxyl amine (155 mg, 0.5 mmol) and pyridine (119 mg, 1.5 mmol) in CH₂Cl₂ (8 ml), and the whole was stirred at room temperature for 17 hours. The reaction mixture was washed with aqueous 0.1 N HCl solution (10 ml), H₂O (20 ml×3) and brine (20 ml), dried over Na₂SO₄, filtered and concentrated in vacuo. The residue was purified by column chromatography (ethyl acetate/petroleum ether: 60/40) to give (S)-1-ethyl-3-(1-(3-(trifluoromethyl)phenylsulfonyl)pyrrolidin-3-yloxy)urea (150 mg, 64%) as pale yellow oil: LCMS: 382 [M+1]$^+$. $^1$H NMR (DMSO-d$_6$) δ: 0.95-1.00 (3H, t), 1.74-1.84 (1H, M), 2.05-2.06 (1H, m), 2.99-3.04 (2H, m), 3.15-3.31 (3H, m), 3.50-3.54 (1H, d), 4.21 (1H, s), 6.66-6.70 (1H, t), 7.84-7.89 (1H, t), 8.01 (1H, s), 8.07-8.14 (1H, t), 8.92 (1H, s).

Example 85

(S)-1-(4-Fluorophenyl)-3-(1-(3-(trifluoromethyl)phenylsulfonyl)pyrrolidin-3-yloxy)urea was prepared as described in EXAMPLE 84

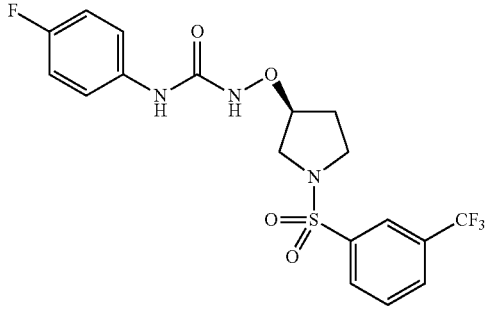 [SMILES: O=C(NO[C@H]1CCN(S(=O)(=O)c2cccc(C(F)(F)F)c2)C1)Nc1ccc(F)cc1]

white solid: LCMS: 448 [M+1]$^+$. $^1$H NMR (DMSO-d$_6$) δ: 1.81-1.88 (1H, m), 2.11-2.16 (1H, m), 3.20-3.36 (3H, m), 4.36 (1H, s), 7.06-7.12 (2H, t), 7.46-7.50 (2H, m), 7.83-7.88 (1H, t), 8.03-8.15 (3H, m), 8.63 (1H, s), 9.45 (1H, s).

Example 86

(S)-1-(3,5-Bis(trifluoromethyl)phenyl)-3-(1-(3-(trifluoromethyl)phenylsulfonyl)pyrrolidin-3-yloxy)urea was prepared as described in EXAMPLE 84

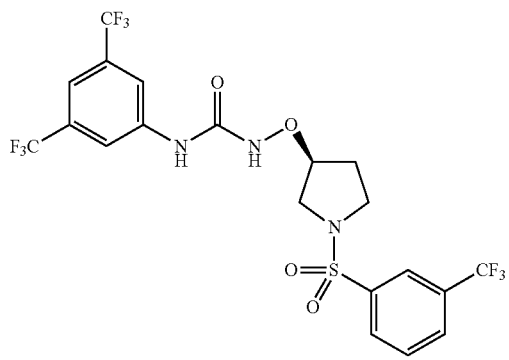 [SMILES: O=C(NO[C@H]1CCN(S(=O)(=O)c2cccc(C(F)(F)F)c2)C1)Nc1cc(C(F)(F)F)cc(C(F)(F)F)c1]

white solid: LCMS: 566 [M+1]$^+$. $^1$H NMR (DMSO-d$_6$) δ: 1.84-1.90 (1H, m), 2.12-2.16 (1H, m), 3.20-3.39 (3H, m), 3.62-3.67 (1H, d), 4.39-4.41 (1H, t), 7.67 (1H, s), 7.81-7.87 (1H, t), 8.02-8.04 (2H, t), 8.12-8.14 (1H, d), 8.26 (2H, s), 9.20 (1H, s).

Example 87

(S)-1-Phenyl-3-(1-(3-(trifluoromethyl)phenylsulfonyl)pyrrolidin-3-yloxy)urea was prepared as described in EXAMPLE 84

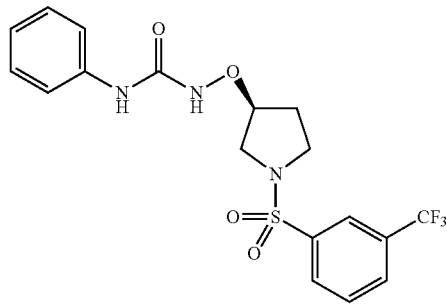 [SMILES: O=C(NO[C@H]1CCN(S(=O)(=O)c2cccc(C(F)(F)F)c2)C1)Nc1ccccc1]

white solid: LCMS: 430 [M+1]$^+$. $^1$H NMR (DMSO-d$_6$) δ: 1.82-1.88 (1H, m), 2.46-2.49 (1H, m), 3 (3H, m), 3.62-3.66 (1H, d), 4.37-4.39 (1H, t), 6.96-7.01 (1H, t), 7.22-7.27 (2H, t), 7.46-7.48 (2H, d), 7.83-7.88 (1H, t), 8.03-8.07 (2H, d), 8.12-8.15 (1H, d), 8.56 (1H, s), 9.42 (1H, s).

Example 88

(S)-1-Cyclohexyl-3-(1-(3-(trifluoromethyl)phenylsulfonyl)pyrrolidin-3-yloxy)urea was prepared as described in EXAMPLE 84

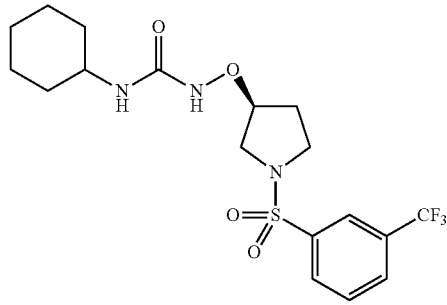 [SMILES: O=C(NO[C@H]1CCN(S(=O)(=O)c2cccc(C(F)(F)F)c2)C1)NC1CCCCC1]

white solid: LCMS: 436 [M+1]$^+$. $^1$H NMR (DMSO-d$_6$) δ: 1.07-1.22 (5H, m), 1.52-1.67 (5H, m), 1.76-1.82 (1H, m), 2.00-2.06 (1H, m), 3.16-3.28 (3H, m), 3.51-3.55 (1H, d), 4.21-4.24 (1H, t), 6.23-6.26 (1H, d), 7.84-7.89 (1H, t), 8.01 (1H, s), 8.08-8.14 (1H, t), 8.91 (1H, s).

Example 89

(S)-1-Propyl-3-(1-(3-(trifluoromethyl)phenylsulfonyl)pyrrolidin-3-yloxy)urea

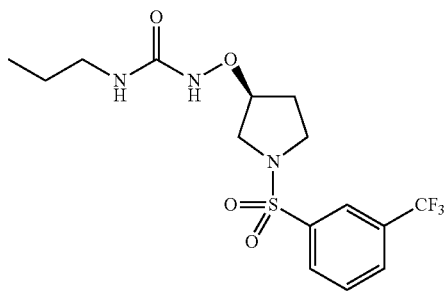 [SMILES: CCCNC(=O)NO[C@H]1CCN(S(=O)(=O)c2cccc(C(F)(F)F)c2)C1]

1,1'-Carbonyldiimidazole (162 mg, 1.00 mmol) was added to a solution of (S)—O-(1-(3-(trifluoromethyl)phenylsulfonyl)pyrrolidin-3-yl)hydroxyl amine (155 mg, 0.50 mmol) and triethylamine (101 mg, 1.00 mmol) in CH$_2$Cl$_2$ (15 ml) and stirred at room temperature for 24 hours. Propan-1-amine (35.0 mg, 0.60 mmol) was added to the reaction mixture and stirred at room temperature for another 17 hours. The reaction mixture was washed with aqueous 0.1 N HCl solution (15 ml), H$_2$O (20 ml×3) and brine (20 ml), dried over Na$_2$SO$_4$ filtered and concentrated in vacuo. The residue was purified by column chromatography (ethyl acetate/petroleum ether: 50/50) to give (S)-1-propyl-3-(1-(3-(trifluoromethyl)phenylsulfonyl)pyrrolidin-3-yloxy)urea (120 mg, 61%) as pale yellow oil: LCMS: 396 [M+1]$^+$. $^1$H NMR (DMSO-d$_6$) δ: 0.76-0.81 (3H, t), 1.34-1.41 (2H, m), 1.77-1.83 (1H, m), 2.01-2.06 (1H, m), 2.90-2.97 (2H, m), 3.16-3.28 (3H, m), 3.50-3.54 (1H, d), 4.22 (1H, s), 6.64-6.68 (1H, t), 7.83-7.89 (1H, t), 8.01 (1H, s), 8.07-8.13 (1H, t), 8.92 (1H, s).

Example 90

(S)-1-Butyl-3-(1-(3-(trifluoromethyl)phenylsulfonyl)pyrrolidin-3-yloxy)urea was prepared as described in EXAMPLE 84

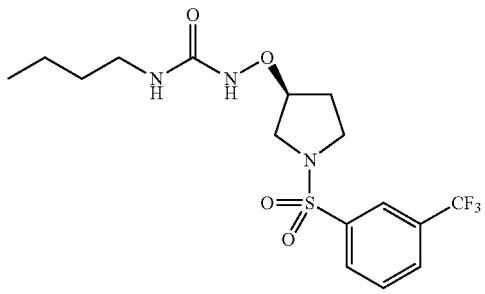 [SMILES: CCCCNC(=O)NO[C@H]1CCN(S(=O)(=O)c2cccc(C(F)(F)F)c2)C1]

white solid: LCMS: 410 [M+1]$^+$. $^1$H NMR (DMSO-d$_6$) δ: 0.82-0.87 (3H, t), 1.15-1.28 (2H, m), 1.30-1.40 (2H, m), 1.75-1.85 (1H, m), 2.01-2.08 (1H, m), 2.94-3.02 (2H, m), 3.12-3.29 (3H, m), 3.50-3.54 (1H, d), 4.19-4.23 (1H, t), 6.62-6.66 (1H, t), 7.84-7.89 (1H, t), 8.01 (1H, s), 8.07-8.14 (2H, t), 8.92 (1H, s).

Example 91

(S)-1-(4-Fluorobenzyl)-3-(1-(3-(trifluoromethyl)phenylsulfonyl)pyrrolidin-3-yloxy)urea was prepared as described in EXAMPLE 84

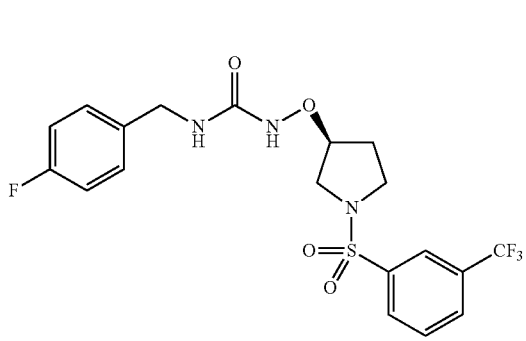 [SMILES: O=C(NCc1ccc(F)cc1)NO[C@H]1CCN(S(=O)(=O)c2cccc(C(F)(F)F)c2)C1]

white solid: LCMS: 462 [M+1]$^+$. $^1$H NMR (DMSO-d$_6$) δ: 1.76-1.84 (1H, m), 2.04-2.10 (1H, m), 3.13-3.22 (1H, m), 3.26-3.32 (2H, m), 3.52-3.56 (1H, d), 4.17-4.19 (2H, d), 4.24-4.27 (1H, t), 7.08-7.14 (2H, m), 7.22-7.27 (2H, m), 7.34-7.38 (1H, t), 7.82-7.87 (1H, t), 8.01 (1H, s), 8.07-8.13 (2H, t), 9.12 (1H, s).

Example 92

(R)-1-Ethyl-3-(1-(3-(trifluoromethyl)phenylsulfonyl)pyrrolidin-3-yloxy)urea was prepared as described in EXAMPLE 84

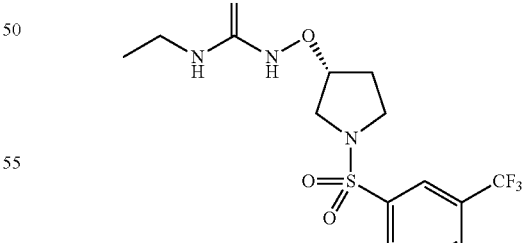

pale yellow oil: LCMS: 382 [M+1]$^+$. $^1$H NMR (DMSO-d$_6$) δ: 0.97 (t, 3H), 1.79 (m, 1H), 2.02 (m, 1H), 3.03 (t, 2H), 3.21 (m, 2H), 3.36 (m, 1H), 3.52 (d, 1H), 4.21 (s, 1H), 6.67 (t, 1H), 7.86 (t, 1H), 8.01 (s, 1H), 8.10 (t, 2H), 8.92 (s, 1H).

Example 93

(R)-1-(4-Fluorophenyl)-3-(1-(3-trifluoromethyl)phenylsulfonyl)pyrrolidin-3-yloxy)urea was prepared as described in EXAMPLE 84

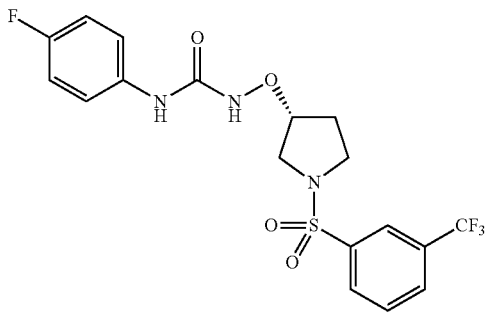 [SMILES: O=C(NO[C@@H]1CCN(S(=O)(=O)c2cccc(C(F)(F)F)c2)C1)Nc1ccc(F)cc1]

white solid: LC-MS: 448 [M+1]+. ¹H NMR (DMSO-d₆) δ: 1.85 (m, 1H), 2.14 (m, 1H), 3.23 (m, 2H), 3.34 (m, 1H), 3.63 (d, 1H), 4.36 (s, 1H), 7.08 (t, 2H), 7.47 (m, 2H), 7.88 (t, 1H), 8.07 (m, 3H), 8.62 (s, 1H), 9.44 (s, 1H).

Example 94

(R)-1-(3,5-Bis(trifluoromethyl)phenyl)-3-(1-(3-(trifluoromethyl)phenylsulfonyl)pyrrolidin-3-yloxy)urea was prepared as described in EXAMPLE 84

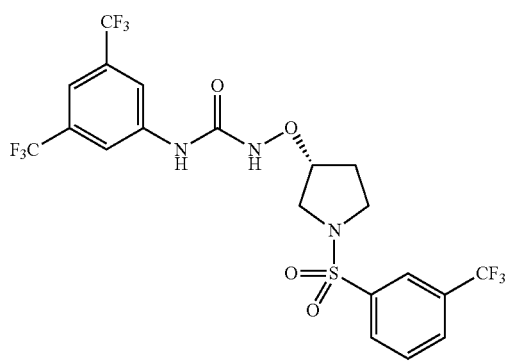 [SMILES: O=C(NO[C@@H]1CCN(S(=O)(=O)c2cccc(C(F)(F)F)c2)C1)Nc1cc(C(F)(F)F)cc(C(F)(F)F)c1]

white solid: LC-MS: 566 [M+1]+. ¹H NMR (DMSO-d₆) δ: 1.85 (m, 1H), 2.14 (m, 1H), 3.29 (m, 1H), 3.35 (m, 2H), 3.63 (d, 1H), 4.4 (s, 1H), 7.67 (s, 1H), 7.85 (m, 1H), 8.03 (s, 2H), 8.13 (d, 1H), 8.26 (s, 2H), 9.2 (s, 1H), 9.89 (s, 1H).

Example 95

(R)-1-Phenyl-3-(1-(3-(trifluoromethyl)phenylsulfonyl)pyrrolidin-3-yloxy)urea was prepared as described in EXAMPLE 84

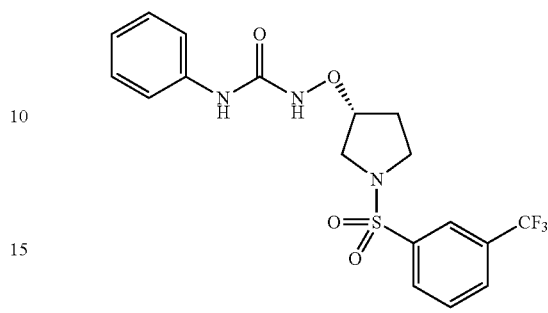

white solid: LC-MS: 430 [M+1]+. ¹H NMR (DMSO-d₆) δ: 1.86 (m, 1H), 2.11 (m, 1H), 3.23 (m, 2H), 3.35 (m, 1H), 3.63 (d, 1H), 4.36 (s, 1H), 6.98 (t, 1H), 7.22 (t, 2H), 7.48 (d, 2H), 7.85 (t, 1H), 8.05 (m, 3H), 8.55 (s, 1H), 9.41 (s, 1H).

Example 96

(R)-1-Cyclohexyl-3-(1-(3-(trifluoromethyl)phenylsulfonyl)pyrrolidin-3-yloxy)urea was prepared as described in EXAMPLE 84

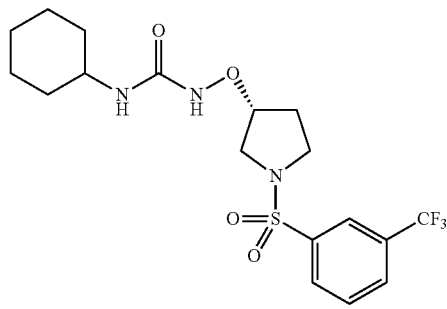 [SMILES: O=C(NO[C@@H]1CCN(S(=O)(=O)c2cccc(C(F)(F)F)c2)C1)NC1CCCCC1]

white solid: LC-MS: 436 [M+1]+. ¹H NMR (DMSO-d₆) δ: 1.03 (m, 1H), 1.21 (m, 4H), 1.59 (m, 1H), 1.72 (m, 4H), 1.81 (m, 1H), 2.02 (m, 1H), 3.22 (m, 3H), 3.35 (m, 1H), 3.52 (d, 1H), 4.22 (s, 1H), 6.25 (d, 1H), 7.86 (t, 1H), 8.0 (s, 1H), 8.11 (t, 2H), 8.91 (s, 1H).

Example 97

(R)-1-Propyl-3-(1-(3-(trifluoromethyl)phenylsulfonyl)pyrrolidin-3-yloxy)urea was prepared as described in EXAMPLE 89

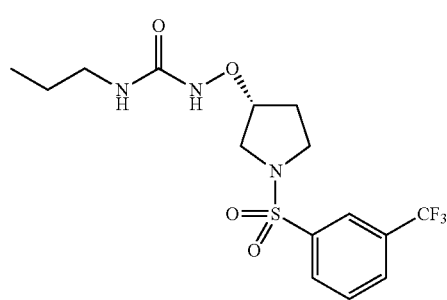 [SMILES: CCCNC(=O)NO[C@@H]1CCN(S(=O)(=O)c2cccc(C(F)(F)F)c2)C1]

colorless oil: LCMS: 396 [M+1]⁺. ¹H NMR (DMSO-d₆) δ: 0.78 (t, 3H), 1.38 (q, 2H), 1.79 (m, 1H), 2.06 (m, 1H), 2.93 (q, 2H), 3.21 (m, 3H), 3.51 (d, 1H), 4.20 (s, 1H), 6.67 (t, 1H), 7.86 (t, 1H), 8.0 (s, 1H), 8.07 (t, 2H), 8.92 (s, 1H).

Example 98

(R)-1-Butyl-3-(1-(3-(trifluoromethyl)phenylsulfonyl) pyrrolidin-3-yloxy)urea was prepared as described in EXAMPLE 89

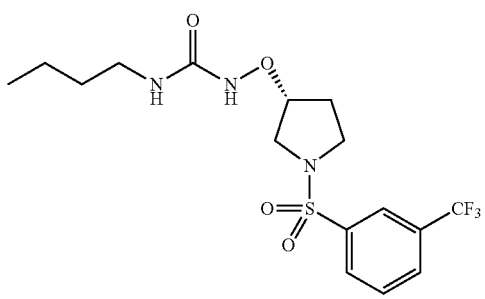 [SMILES: CCCCNC(=O)NO[C@@H]1CCN(S(=O)(=O)c2cccc(C(F)(F)F)c2)C1]

colorless oil: LC-MS: 410 [M+1]⁺. ¹H NMR (DMSO-₆) δ: 0.84 (t, 3H), 1.21 (q, 2H), 1.36 (q, 2H), 1.79 (m, 1H), 2.06 (m, 1H), 2.99 (q, 2H), 3.17 (m, 3H), 3.49 (d, 1H), 4.20 (s, 1H), 6.64 (t, 1H), 7.86 (t, 1H), 8.0 (s, 1H), 8.09 (t, 2H), 8.91 (s, 1H).

Example 99

(R)-1-(4-Fluorobenzyl)-3-(1-(3-(trifluoromethyl) phenylsulfonyl)pyrrolidin-3-yloxy)urea was prepared as described in EXAMPLE 89

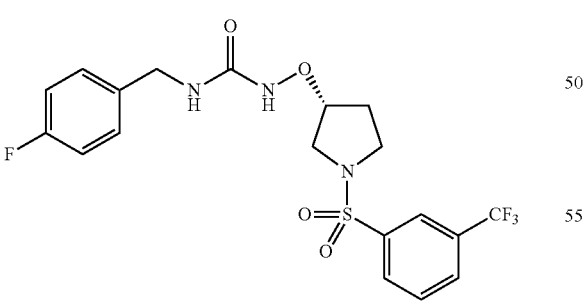

colorless oil: LC-MS: 462 [M+1]⁺. ¹H NMR (DMSO-d₆) δ: 1.81 (m, 1H), 2.06 (m, 1H), 3.25 (m, 2H), 3.32 (m, 1H), 3.53 (d, 1H), 4.17 (d, 2H), 4.25 (s, 1H), 7.10 (t, 2H), 7.23 (m, 2H), 7.35 (t, 1H), 7.85 (t, 1H), 8.0 (s, 1H), 8.10 (t, 2H), 9.12 (s, 1H).

Example 100

1-Cyclopropyl-3-(1-(3-(trifluoromethyl)phenylsulfonyl)pyrrolidin-3-yloxy)urea was prepared as described in EXAMPLE 99

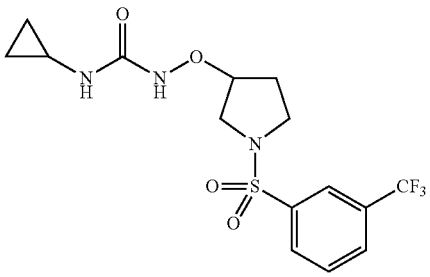 [SMILES: O=C(NOC1CCN(S(=O)(=O)c2cccc(C(F)(F)F)c2)C1)NC1CC1]

white solid: LCMS: 394 [M+1]⁺. ¹H NMR (DMSO-d₆) δ: 0.40 (m, 2H), 0.57 (m, 2H), 1.80 (m, 1H), 2.04 (m, 1H), 2.48 (m, 1H), 3.21 (m, 3H), 3.53 (d, 1H), 4.23 (m, 1H), 6.70 (d, 1H), 7.88 (t, 1H), 8.02 (d, 1H), 8.10 (m, 2H), 9.02 (s, 1H).

Example 101

(R)-1-Cyclopropyl-3-(1-(3-(trifluoromethyl)phenylsulfonyl)pyrrolidin-3-yloxy)urea was prepared as described in EXAMPLE 89

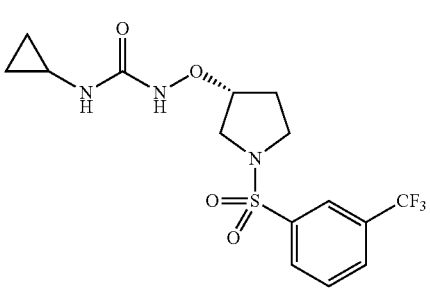 [SMILES: O=C(NO[C@@H]1CCN(S(=O)(=O)c2cccc(C(F)(F)F)c2)C1)NC1CC1]

white solid: LCMS: 394 [M+1]⁺. ¹H NMR (DMSO-d₆) δ: 0.40 (m, 2H), 0.57 (m, 2H), 1.80 (m, 1H), 2.04 (m, 1H), 2.48 (m, 1H), 3.21 (m, 3H), 3.53 (d, 1H), 4.23 (m, 1H), 6.70 (d, 1H), 7.88 (t, 1H), 8.02 (d, 1H), 8.10 (m, 2H), 9.02 (s, 1H).

Example 102

(S)-1-(4-Fluorophenyl)-3-(1-(4-(trifluoromethoxy)phenylsulfonyl)pyrrolidin-3-yloxy)urea

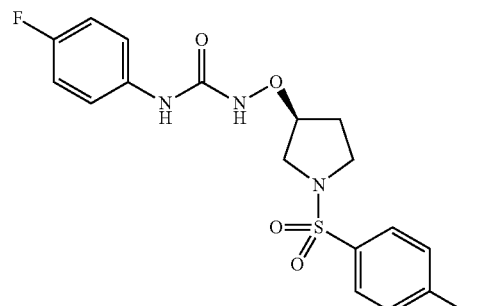

A solution of (S)—O-(1-(4-(trifluoromethoxy)phenylsulfonyl)pyrrolidin-3-yl)hydroxylamine (250 mg, 0.76 mmol) in tetrahydrofuran (10 ml) was added over 30 minutes to a suspension of trichloromethyl chloroformate (227 mg, 1.15 mmol) and activated charcoal (20 mg) in tetrahydrofuran (35 ml) at 0° C. over 30 minutes. After stirring at room temperature for 18 hours, the reaction mixture was filtered over silicagel and the filtrate was concentrated in vacuo. The residue was dissolved in tetrahydrofuran (15 ml), 4-fluoroaniline (93.6 mg, 0.84 mmol) and N,N-diisopropylethylamine (296 mg, 2.3 mmol) were added and the whole was stirred at room temperature for 18 hours. The reaction mixture was concentrated in vacuo and the residue was diluted with ethyl acetate (50 ml), washed with $H_2O$ (20 ml×2), brine (20 ml×2), dried over $Na_2SO_4$ and concentrated in vacuo. The residual solid was recrystallized from diethyl ether to give (S)-1-(4-fluorophenyl)-3-(1-(4-(trifluoromethoxy)phenylsulfonyl)pyrrolidin-3-yloxy)urea as a white solid (127 mg, 36%): LCMS: 464 [M+1]$^+$. $^1$H NMR (DMSO-$d_6$) δ: 1.85 (m, 1H), 2.09 (m, 1H), 3.25 (m, 3H), 3.53 (d, 1H), 4.36 (s, 1H), 7.07 (t, 2H), 7.47 (d, 2H), 7.56 (d, 2H), 7.92 (d, 2H), 8.63 (s, 1H), 9.45 (s, 1H).

Example 103

(S)-1-(4-Methoxyphenyl)-3-(1-(4-(trifluoromethoxy)phenylsulfonyl)pyrrolidin-3-yloxy)urea was prepared as described in EXAMPLE 102

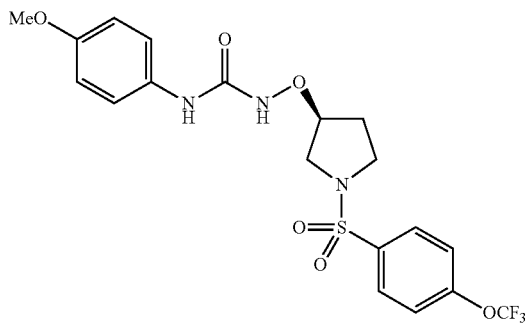 [SMILES: COc1ccc(NC(=O)NO[C@H]2CCN(S(=O)(=O)c3ccc(OC(F)(F)F)cc3)C2)cc1]

white solid: LCMS: 476 [M+1]$^+$. $^1$H NMR (DMSO-$d_6$) δ: 1.82 (m, 1H), 2.11 (m, 1H), 3.25 (m, 3H), 3.53 (d, 1H), 3.72 (s, 3H), 4.36 (s, 1H), 6.82 (d, 2H), 7.37 (t, 2H), 7.56 (d, 2H), 7.95 (t, 2H), 8.44 (s, 1H), 9.32 (s, 1H).

Example 104

(S)-1-(4-Fluorobenzyl)-3-(1-(4-(trifluoromethoxy)phenylsulfonyl)pyrrolidin-3-yloxy)urea was prepared as described in EXAMPLE 102

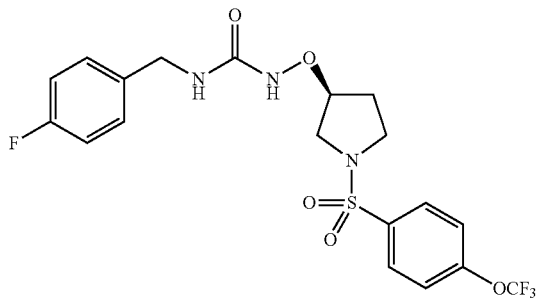 [SMILES: O=C(NCc1ccc(F)cc1)NO[C@H]1CCN(S(=O)(=O)c2ccc(OC(F)(F)F)cc2)C1]

white solid: LCMS: 478 [M+1]$^+$. $^1$H NMR (DMSO-$d_6$) δ: 1.77 (m, 1H), 2.03 (m, 1H), 3.21 (m, 3H), 3.35 (d, 1H), 4.19 (d, 2H), 4.25 (s, 1H), 7.08 (t, 2H), 7.24 (t, 2H), 7.38 (t, 1H), 7.54 (d, 2H), 7.95 (t, 2H), 9.12 (s, 1H).

Example 105

1-Cyclopropyl-3-(1-(4-(trifluoromethoxy)phenylsulfonyl)piperidin-4-yloxy)urea was prepared as described in EXAMPLE 67

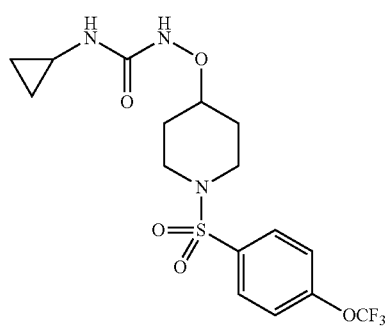 [SMILES: O=C(NOC1CCN(S(=O)(=O)c2ccc(OC(F)(F)F)cc2)CC1)NC1CC1]

white solid: LCMS: 424 [M+1]$^+$. $^1$H NMR (DMSO-$d_6$) δ: 0.41 (m, 2H), 0.55 (m, 2H), 1.71 (m, 2H), 1.84 (m, 2H), 2.48 (1H, m), 2.82 (m, 2H), 3.16 (m, 2H), 3.62 (m, 1H), 6.64 (d, 1H), 7.64 (d, 2H), 7.88 (d, 2H), 8.89 (s, 1H).

Example 106

1-(1-(Bis(4-fluorophenyl)methyl)piperidin-4-yloxy)-3-(4-fluorophenyl)urea

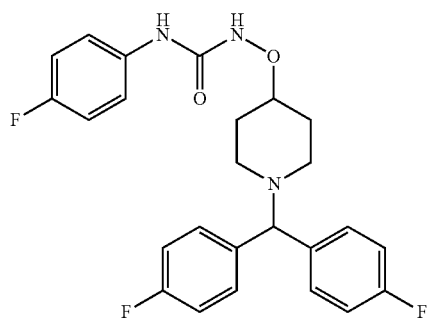 [SMILES: O=C(NOC1CCN(C(c2ccc(F)cc2)c2ccc(F)cc2)CC1)Nc1ccc(F)cc1]

a) A mixture of 2-(piperidin-4-yloxy)isoindoline-1,3-dione hydrochloride (282 mg, 0.997 mmol), $K_2CO_3$ (303 mg, 2.19 mmol) and KI (17 mg, 0.10 mmol) in acetonitrile (5 ml) was stirred under reflux for 6 hours. The reaction was quenched with $H_2O$ (20 ml), extracted with chloroform (30 ml×2), dried over $MgSO_4$ and concentrated in vacuo. The residue was purified by column chromatography (ethyl acetate/hexane: 15/85 to 35/65) to give 2-(1-(bis(4-fluorophenyl)methyl)piperidin-4-yloxy)isoindoline-1,3-dione (193 mg, 41%) as pale yellow oil.

b) Hydrazine monohydrate (0.059 ml, 1.2 mmol) was added to a solution of 2-(1-(bis(4-fluorophenyl)methyl)piperidin-4-yloxy)isoindoline-1,3-dione (193 mg, 0.406 mmol) in $CH_2Cl_2$ (5 ml) and stirred at room temperature for 15 hours. The resulting solid was filtered off and the filtrate was concentrated in vacuo. The residue was dissolved in tetrahydrofuran (5 ml), 4-fluorophenyl isocyanate (0.023 ml, 0.20 mmol) was added and the whole was stirred at room temperature for 15 hours. The reaction mixture was concentrated in vacuo, the residue was purified by column chromatography (ethyl acetate/hexane: 25/75 to 45/55) and the resulting solid was recrystallized from ethyl acetate/hexane to give 1-(1-(bis(4-fluorophenyl)methyl)piperidin-4-yloxy)-3-(4-fluorophenyl)urea (120 mg, 65%) as a white solid: LCMS: 456 [M+1]$^+$. $^1$H NMR (DMSO-$d_6$) δ: 1.68 (m, 2H), 1.90-2.02 (m, 4H), 2.62 (m, 2H), 3.70 (m, 1H), 4.40 (s, 1H), 7.10 (m, 6H), 7.43 (m, 4H), 7.55 (m, 2H), 8.61 (s, 1H), 9.38 (s, 1H).

Example 107

1-(4-Fluorophenyl)-3-(1-(4-(trifluoromethoxy)benzyl)piperidin-4-yloxy)urea was prepared as described in EXAMPLE 106

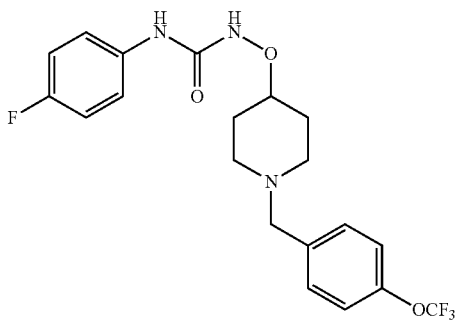 [SMILES: O=C(NOC1CCN(Cc2ccc(OC(F)(F)F)cc2)CC1)Nc1ccc(F)cc1]

white solid: LCMS: 428 [M+1]$^+$. $^1$H NMR (DMSO-$_6$) δ: 1.70 (m, 2H), 1.95 (m, 2H), 2.11 (m, 2H), 2.74 (m, 2H), 3.51 (s, 2H), 3.74 (m, 1H), 4.40 (s, 1H), 7.08 (m, 2H), 7.34 (m, 2H), 7.46 (m, 1H), 7.56 (m, 2H), 8.66 (s, 1H), 9.43 (s, 1H).

Example 108

1-(4-Fluorophenyl)-3-(1-(1-(4-(trifluoromethoxy)phenyl)ethyl)piperidin-4-yloxy)urea was prepared as described in EXAMPLE 106

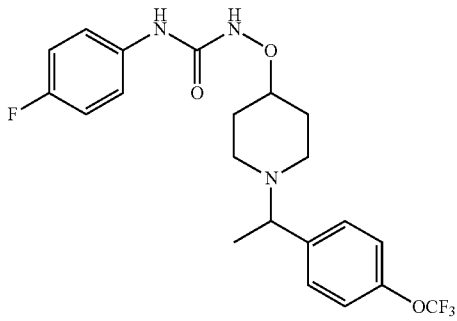 [SMILES: CC(c1ccc(OC(F)(F)F)cc1)N1CCC(ONC(=O)Nc2ccc(F)cc2)CC1]

white solid: LCMS: 442 [M+1]$^+$. $^1$H NMR (DMSO-$d_6$) δ: 1.28 (d, 3H), 1.63 (m, 2H), 1.91 (m, 2H), 2.24 (m, 2H), 2.64 (m, 1H), 2.80 (m, 1H), 3.52 (m, 1H), 3.63 (m, 1H), 4.40 (s, 1H), 7.10 (m, 2H), 7.32 (m, 2H), 7.43 (m, 2H), 7.55 (m, 2H), 8.59 (s, 1H), 9.37 (s, 1H).

Example 109

1-(1-(Cyano(4-(trifluoromethoxy)phenyl)methyl)piperidin-4-yloxy)-3-(4-fluorophenyl)urea

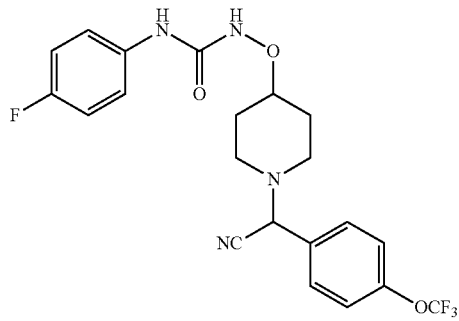 [SMILES: N#CC(c1ccc(OC(F)(F)F)cc1)N1CCC(ONC(=O)Nc2ccc(F)cc2)CC1]

a) 4-(Trifluoromethoxy)benzaldehyde (0.342 ml, 2.39 mmol) was added to a solution of diethyl phosphorocyanidate (0.363 ml, 2.39 mmol) in tetrahydrofuran (12 ml) and stirred at room temperature for 10 minutes. A suspension of 2-(piperidin-4-yloxy)isoindoline-1,3-dione hydrochloride (564 mg, 2.00 mmol) and triethylamine (0.332 ml, 2.39 mmol) in tetrahydrofuran (6 ml) was added to the reaction mixture, and the whole was stirred at room temperature for 24 hours and at 60° C. for 17 hours. The reaction mixture was concentrated in vacuo and the residue was purified by column chromatography (ethyl acetate/hexane: 5/95 to 25/75) to give 2-(4-(1,3-dioxoisoindolin-2-yloxy)piperidin-1-yl)-2-(4-(trifluoromethoxy)phenyl)acetonitrile (261 mg, 22%).

b) Hydrazine monohydrate (0.063 ml, 1.303 mmol) was added to a solution of 2-(4-(1,3-dioxoisoindolin-2-yloxy)piperidin-1-yl)-2-(4-(trifluoromethoxy)phenyl)acetonitrile (258 mg, 0.434 mmol) in $CH_2Cl_2$ (5 ml) and the whole was stirred at room temperature for 16 hours. The resulting solid was filtered off and the filtrate was concentrated in vacuo. The residue was dissolved in tetrahydrofuran (5 ml), treated with 4-fluorophenyl isocyanate (0.023 ml, 0.200 mmol) and stirred at room temperature for 14 hours. The reaction mixture was concentrated in vauo and the residue was purified by column chromatography (ethyl acetate/hexane: 50/50 to 0/100) and the resulting solid was triturated with ethyl acetate/hexane to give 1-(1-(cyano(4-(trifluoromethoxy)phenyl)methyl)piperidin-4-yloxy)-3-(4-fluorophenyl)urea (110 mg, 56%) as a white solid: LCMS: 442 [M+1]$^+$. $^1$H NMR (DMSO-$d_6$) δ: 1.67 (m, 1H), 1.81 (m, 1H), 1.94 (m, 2H), 2.33 (m, 2H), 2.58 (m, 1H), 2.88 (m, 1H), 3.76 (m, 1H), 5.47 (s, 1H), 7.10 (m, 2H), 7.46-7.60 (m, 6H), 8.62 (s, 1H), 9.43 (s, 1H).

Example 110

1-(4-Fluorophenyl)-3-(1-(1-(4-(trifluoromethoxy)phenyl)cyclopropyl)piperidin-4-yloxy)urea

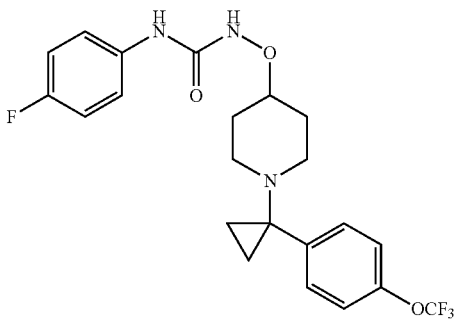 [SMILES: O=C(NOC1CCN(C2(c3ccc(OC(F)(F)F)cc3)CC2)CC1)Nc1ccc(F)cc1]

a) Ethylmagnesium bromide (3.0 M in diethyl ether, 7.33 ml, 22.0 mmol) was added over 50 minutes to a solution of 4-(trifluoromethoxy)benzonitrile (1.87 g, 10.0 mmol) and tetraisopropoxytitanium (3.22 ml, 11.0 mmol) in diethyl ether (50 ml) at −70° C., and the whole was stirred at room temperature for 1 hour. Boranetrifluoride diethyl ether complex (2.53 ml, 20.0 mmol) was added over 15 minutes to the reaction mixture and the whole was stirred at room temperature for 3 hours. 1N aqueous HCl solution (30 ml) and diethyl ether (90 ml) were added to the reaction mixture, and the whole was poured into aqueous 10% NaOH solution (100 ml), extracted with diethyl ether (150 ml×2), dried over $Na_2SO_4$, filtered and concentrated in vacuo. The residue was purified by column chromatography (ethyl acetate/hexane: 55/45 to 75/25) to give 1-(4-(trifluoromethoxy)phenyl)cyclopropanamine (1.38 g, 63%).

b) A solution of 1-benzyl-1-methyl-4-oxopiperidinium iodide (2.69 g, 8.13 mmol) in ethanol-$H_2O$ (2:1, 30 ml) was added to the solution of 1-(4-(trifluoromethoxy)phenyl)cyclopropanamine (1.37 g, 6.26 mmol) and $K_2CO_3$ (86 mg, 0.626 mmol) in ethanol (20 ml) at 80° C. and stirred for 4 hours. The reaction was quenched with $H_2O$ (100 ml), extracted with diethyl ether (100 ml×2), dried over $Na_2SO_4$, filtered and concentrated in vacuo. The residue was purified by column chromatography (ethyl acetate/hexane: 25/75 to 45/55) to give (trifluoromethoxy)phenyl)cyclopropyl)piperidin-4-one (1.43 g, 76%) as a pale yellow solid.

c) $NaBH_4$ (95 mg, 2.5 mmol) was added to a solution of (trifluoromethoxy)phenyl)cyclopropyl)piperidin-4-one (750 mg, 2.51 mmol) in methanol (25 ml) and stirred at room temperature for 1 hour. The reaction mixture was concentrated in vacuo, diluted with ethyl acetate (50 ml), washed with aqueous $NaHCO_3$ solution (30 ml) and brine, dried over $Na_2SO_4$, filtered and concentrated in vacuo to give 1-(1-(4-(trifluoromethoxy)phenyl)cyclopropyl)piperidin-4-ol (754 mg, 98%) as pale-yellow oil.

d) Diethyl azodicarboxylate (1.23 ml, 2.70 mmol) was added dropwise to a solution of 1-(1-(4-(trifluoromethoxy)phenyl)cyclopropyl)piperidin-4-ol (750 mg, 2.45 mmol), 2-hydroxyisoindoline-1,3-dione (400 mg, 2.45 mmol) and triphenylphosphine (707 mg, 2.70 mmol) in tetrahydrofuran (15 ml) at 0° C. and the whole was stirred at room temperature for 18 hours. The reaction mixture was concentrated in vacuo and the residue was purified by column chromatography (ethyl acetate/hexane: 25/75 to 45/55) to give 2-(1-(1-(4-(trifluoromethoxy)phenyl)cyclopropyl)piperidin-4-yloxy)isoindoline-1,3-dione (1.00 g, 85%) as pale yellow amourphous.

e) The mixture of 2-(1-(1-(4-(trifluoromethoxy)phenyl)cyclopropyl)piperidin-4-yloxy)isoindoline-1,3-dione (995 mg, 2.08 mmol) and hydrazine monohydrate (0.304 ml, 6.25 mmol) in $CH_2Cl_2$ (10 ml) was stirred at room temperature for 3 hours. The resulting solid was filtered off and the filtrate was concentrated in vacuo. The residue was purified by column chromatography (ethyl acetate/hexane: 45/55 to 75/25) to give O-(1-(1-(4-(trifluoromethoxy)phenyl)cyclopropyl)piperidin-4-yl)hydroxylamine (580 mg, 88%) as pale yellow oil.

f) 4-Fluorophenyl isocyanate (0.062 ml, 0.546 mmol) was added to a solution of O-(1-(1-(4-(trifluoromethoxy)phenyl)cyclopropyl)piperidin-4-yl)hydroxylamine (157 mg, 0.496 mmol) in tetrahydrofuran (5 ml) and the whole was stirred at room temperature for 12 hours. The reaction mixture was concentrated in vacuo and the residue was purified by column chromatography (ethyl acetate/hexane: 25/75 to 45/55) to give 1-(4-fluorophenyl)-3-(1-(1-(4-(trifluoromethoxy)phenyl)cyclopropyl)piperidin-4-yloxy)urea (221 mg, 98%) as a white solid: LCMS: 454 $[M+1]^+$. $^1H$ NMR (DMSO-$d_6$) δ: 0.76 (s, 2H), 0.88 (s, 2H), 1.59 (m, 2H), 1.84 (m, 2H), 2.08 (m, 2H), 2.81 (m, 2H), 3.48 (m, 1H), 5.47 (s, 1H), 7.08 (m, 2H), 7.30 (m, 2H), 7.38 (m, 2H), 7.51 (m, 2H), 8.49 (s, 1H), 9.30 (s, 1H).

Example 111

1-(1-Methylcyclopropyl)-3-(1-(4-(trifluoromethoxy)phenylsulfonyl)piperidin-4-yloxy)urea was prepared as described in EXAMPLE 67

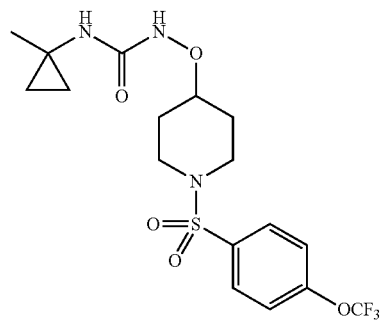 [SMILES: CC1(NC(=O)NOC2CCN(S(=O)(=O)c3ccc(OC(F)(F)F)cc3)CC2)CC1]

white solid: LCMS: 438 $[M+1]^+$. $^1H$ NMR (DMSO-$d_6$) δ: 0.48 (m, 2H), 0.58 (m, 2H), 1.22 (s, 3H), 1.70 (m, 2H), 1.83 (m, 2H), 2.82 (m, 2H), 3.14 (m, 2H), 3.60 (m, 1H), 6.84 (s, 1H), 7.64 (m, 2H), 7.88 (m, 2H), 8.78 (s, 1H).

Example 112

1-(1-(4-(Trifluoromethoxy)phenylsulfonyl)piperidin-4-yloxy)-3-(1-(trifluoromethyl)cyclobutyl)urea was prepared as described in EXAMPLE 67

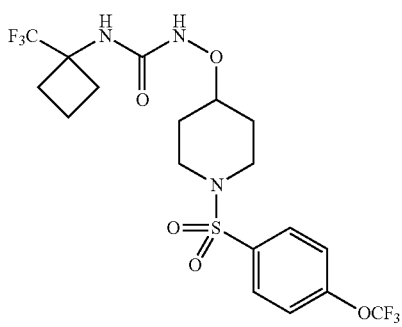 [SMILES: O=C(NOC1CCN(S(=O)(=O)c2ccc(OC(F)(F)F)cc2)CC1)NC1(C(F)(F)F)CCC1]

white solid: LCMS: 506 [M+1]$^+$. $^1$H NMR (DMSO-d$_6$) δ: 1.74-1.91 (m, 6H), 2.35-2.50 (m, 4H), 2.81 (m, 2H), 3.21 (m, 2H), 3.67 (m, 1H), 7.01 (s, 1H), 7.64 (m, 2H), 7.89 (m, 2H), 9.06 (s, 1H).

Example 113

1-(1-(4-(Trifluoromethoxy)phenylsulfonyl)piperidin-4-yloxy)-3-(1-(trifluoromethyl)cyclopropyl)urea was prepared as described in EXAMPLE 67

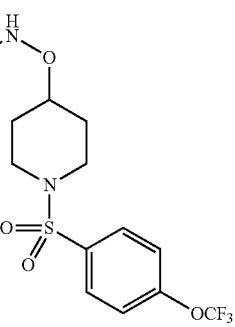

white solid: LCMS: 492 [M+1]$^+$. $^1$H NMR (DMSO-d$_6$) δ: 1.02 (m, 2H), 1.19 (m, 2H), 1.74 (m, 2H), 1.85 (m, 2H), 2.80 (m, 2H), 3.19 (m, 2H), 3.63 (m, 1H), 7.49 (s, 1H), 7.65 (m, 2H), 7.89 (m, 2H), 9.15 (s, 1H).

Compounds of the invention have been tested in the calcium mobilization and/or electrophysiological assay for N-type calcium channel blocking activity, which are described in detail above. Some compounds described have also been tested in the calcium mobilization assay for L-type calcium channel blocking activity, which is described in detail above. Representative values are presented in TABLE 2.

TABLE 2

Evaluation of the tested compounds as N-type calcium channel (NTCC) blockers and L-type calcium channel (LTCC) blockers after a calcium mobilization in vitro assay

| EXAMPLE | NTCC (nM) | LTCC (nM) |
|---|---|---|
| 5 | 102 | |
| 7 | 575 | 20000 |
| 9 | 218 | |
| 16 | 1218 | |
| 31 | 154 | 20000 |
| 32 | 560 | 20000 |
| 55 | 290 | |
| 67 | 1486 | 20000 |
| 86 | 705 | 20000 |
| 106 | 2584 | |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

The invention claimed is:
1. A compound having Formula I:

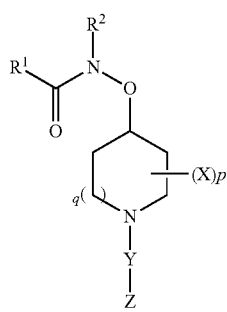

I or a pharmaceutically acceptable salt thereof, wherein:
$R^1$ is optionally substituted alkyl, optionally substituted alkenyl, optionally substituted alkynyl, optionally substituted amino, optionally substituted carbamoyl, optionally substituted cycloalkyl, optionally substituted aryl or optionally substituted heterocyclyl,
$R^2$ is hydrogen or optionally substituted alkyl, or $R^1$ and $R^2$ can be taken together with the adjacent atoms to form a ring;

Y is $CR^3R^4$ or $SO_m$;

$R^3$ and $R^4$ are each independently hydrogen, cyano, optionally substituted alkyl, optionally substituted alkenyl, optionally substituted alkynyl, optionally substituted cycloalkyl, optionally substituted aryl or optionally substituted heterocyclyl, or $R^3$ and $R^4$ can be taken together with the neighboring carbon atom to form a ring;

Z is optionally substituted alkyl, optionally substituted alkenyl, optionally substituted alkynyl, optionally substituted cycloalkyl, optionally substituted aryl, optionally substituted heterocyclyl, $NR^5R^6$, $COR^5$ or $CONR^5R^6$;

each X is independently =O, optionally substituted alkyl, optionally substituted alkenyl, optionally substituted alkynyl, halogen, cyano, nitro, $NR^5R^6$, $OR^5$, $SR^5$, $COR^5$, $COOR^5$, $CONR^5R^6$, $NR^5COR^6$, $OCOR^5$, $SOR^5$, $SO_2R^5$, $SO_3R^5$, $SONR^5R^6$, $SO_2NR^5R^6$, $NR^5SOR^6$, or $NR^5SO_2R^6$;

$R^5$ and $R^6$ are each independently hydrogen, optionally substituted alkyl, optionally substituted alkenyl, optionally substituted alkynyl, optionally substituted cycloalkyl, optionally substituted aryl or optionally substituted heterocyclyl;
m is 1 or 2;
p is 0, 1 or 2; and
q is 0 or 1;
and provided that
when q is 0, X is not OH or COOR⁵.

2. The compound of claim 1, wherein Y is CR³R⁴ or SO₂; and
R³ and R⁴ are each independently hydrogen, cyano, optionally substituted alkyl or optionally substituted aryl.

3. The compound of claim 1, wherein Z is optionally substituted aryl or optionally substituted heterocyclyl.

4. The compound of claim 1, wherein Z is optionally substituted phenyl.

5. The compound of claim 1, wherein R¹ is optionally substituted alkyl, optionally substituted alkenyl, optionally substituted amino, optionally substituted carbamoyl, optionally substituted cycloalkyl, optionally substituted aryl or optionally substituted heterocyclyl; or
R¹ and R² can be taken together with the neighboring nitrogen atom to form a ring.

6. The compound of claim 1, wherein:
R¹ is optionally substituted alkyl, optionally substituted alkenyl, optionally substituted carbamoyl, optionally substituted cycloalkyl, optionally substituted aryl or optionally substituted heterocyclyl,
R² is hydrogen, or
R¹ and R² can be taken together with the neighboring nitrogen atom to form a ring,
Y is SO₂; and
Z is optionally substituted aryl.

7. A compound having Formula I:

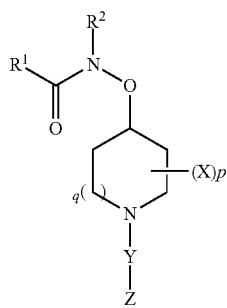

or a pharmaceutically acceptable salt thereof, wherein:
R¹ is optionally substituted amino,
R² is hydrogen or optionally substituted alkyl,
Y is CR³R⁴ or SO_m;
R³ and R⁴ are each independently hydrogen, cyano, optionally substituted alkyl, optionally substituted alkenyl, optionally substituted alkynyl, optionally substituted cycloalkyl, optionally substituted aryl or optionally substituted heterocyclyl, or
R³ and R⁴ can be taken together with the neighboring carbon atom to form a ring;
Z is optionally substituted alkyl, optionally substituted alkenyl, optionally substituted alkynyl, optionally substituted cycloalkyl, optionally substituted aryl, optionally substituted heterocyclyl, NR⁵R⁶, COR⁵ or CONR⁵R⁶;

each X is independently =O, optionally substituted alkyl, optionally substituted alkenyl, optionally substituted alkynyl, halogen, cyano, nitro, NR⁵R⁶, OR⁵, SR⁵, COR⁵, COOR⁵, CONR⁵R⁶, NR⁵COR⁶, OCOR⁵, SOR⁵, SO₂R⁵, SO₃R⁵, SONR⁵R⁶, SO₂NR⁵R⁶, NR⁵SOR⁶, or NR⁵SO₂R⁶;
R⁵ and R⁶ are each independently hydrogen, optionally substituted alkyl, optionally substituted alkenyl, optionally substituted alkynyl, optionally substituted cycloalkyl, optionally substituted aryl or optionally substituted heterocyclyl;
m is 1 or 2;
p is 0, 1 or 2; and
q is 0 or 1.

8. A pharmaceutical composition, comprising the compound of claim 1 or 7 and a pharmaceutically acceptable carrier.

9. The compound having Formula I as claimed in claims 1 or 7, wherein the compound is ³H, ¹¹C, or ¹⁴C radiolabeled.

10. A pharmaceutical composition for modulating calcium channels in a mammal, comprising the compound having Formula I:

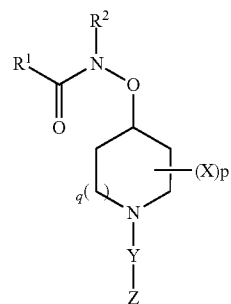

or a pharmaceutically acceptable salt thereof, wherein:
R¹ is optionally substituted alkyl, optionally substituted alkenyl, optionally substituted alkynyl, optionally substituted amino, optionally substituted carbamoyl, optionally substituted cycloalkyl, optionally substituted aryl or optionally substituted heterocyclyl,
R² is hydrogen or optionally substituted alkyl, or
R¹ and R² can be taken together with the adjacent atoms to form a ring;
Y is CR³R⁴ or SO_m;
R³ and R⁴ are each independently hydrogen, cyano, optionally substituted alkyl, optionally substituted alkenyl, optionally substituted alkynyl, optionally substituted cycloalkyl, optionally substituted aryl or optionally substituted heterocyclyl, or
R³ and R⁴ can be taken together with the neighboring carbon atom to form a ring;
Z is optionally substituted alkyl, optionally substituted alkenyl, optionally substituted alkynyl, optionally substituted cycloalkyl, optionally substituted aryl, optionally substituted heterocyclyl, NR⁵R⁶, COR⁵ or CONR⁵R⁶;
each X is independently =O, optionally substituted alkyl, optionally substituted alkenyl, optionally substituted alkynyl, halogen, cyano, nitro, NR⁵R⁶, OR⁵, SR⁵, COR⁵, COOR⁵, CONR⁵R⁶, NR⁵COR⁶, OCOR⁵, SOR⁵, SO₂R⁵, SO₃R⁵, SONR⁵R⁶, SO₂NR⁵R⁶, NR⁵SOR⁶, or NR⁵SO₂R⁶;

$R^5$ and $R^6$ are each independently hydrogen, optionally substituted alkyl, optionally substituted alkenyl, optionally substituted alkynyl, optionally substituted cycloalkyl, optionally substituted aryl or optionally substituted heterocyclyl;

m is 1 or 2;

p is 0, 1 or 2; and q is 0 or 1;

and a pharmaceutically acceptable carrier.

* * * * *

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
caccatggtc cgcttcgggg ac    22

<210> SEQ ID NO 2
<211> LENGTH: 19

```
<212> TYPE: DNA
<213> ORGANISM: Artificial Sequence
<220> FEATURE:
<223> OTHER INFORMATION: Primer

<400> SEQUENCE: 2
ccgttcagtg gcctcctcc                                                    19

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ctagcaccag tgatcctggt ctg                                               23

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
agtgcgttgt gagcgcagta                                                   20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
caccatggtc cagaagagcg g                                                 21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
tctcagcgga tgtagacgcc t                                                 21

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
caccatgtat gacgactcct ac                                                22

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
ggtggtcagt agctgtcctt agg                                               23
```

```
<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
caccatggct gctggctgcc t                                    21

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
agagggtcac catagatagt gtctg                                25

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
caccatgatt cgggccttcg ct                                   22

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
agcctgcgga ctacaggttg ctgac                                25
```